US008632997B2

(12) United States Patent
Tuschl et al.

(10) Patent No.: US 8,632,997 B2
(45) Date of Patent: *Jan. 21, 2014

(54) RNA SEQUENCE-SPECIFIC MEDIATORS OF RNA INTERFERENCE

(75) Inventors: Thomas Tuschl, Goettingen (DE); Phillip D. Zamore, Northborough, MA (US); Phillip A. Sharp, Newton, MA (US); David P. Bartel, Brookline, MA (US)

(73) Assignees: University of Massachusetts, Boston, MA (US); Whitehead Institute for Biomedical Research, Cambridge, MA (US); Massachusetts Institute of Technology, Cambridge, MA (US); Max-Planck-Gesellschaft zur Förderung der Wissenschaften E.V., Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/897,749

(22) Filed: Oct. 4, 2010

(65) Prior Publication Data

US 2011/0244446 A1    Oct. 6, 2011

Related U.S. Application Data

(60) Continuation of application No. 11/474,930, filed on Jun. 26, 2006, now abandoned, which is a division of application No. 09/821,832, filed on Mar. 30, 2001, now abandoned.

(60) Provisional application No. 60/193,594, filed on Mar. 30, 2000, provisional application No. 60/265,232, filed on Jan. 31, 2001.

(30) Foreign Application Priority Data

Dec. 1, 2000  (EP) .................... 00126325

(51) Int. Cl.
C12P 19/34    (2006.01)
C12Q 1/68    (2006.01)
A61K 48/00    (2006.01)
C07H 21/02    (2006.01)

(52) U.S. Cl.
USPC ............... 435/91.1; 435/6; 514/44; 536/23.1; 536/24.5

(58) Field of Classification Search
None
See application file for complete search history.

(56) References Cited

U.S. PATENT DOCUMENTS

| | | |
|---|---|---|
| 4,469,863 A | 9/1984 | Ts'o et al. |
| 5,208,149 A | 5/1993 | Inouye |
| 5,457,189 A | 10/1995 | Crooke et al. |
| 5,514,577 A | 5/1996 | Draper et al. |
| 5,576,208 A | 11/1996 | Monia et al. |
| 5,578,716 A | 11/1996 | Szyf et al. |
| 5,580,859 A | 12/1996 | Felgner et al. |
| 5,594,122 A | 1/1997 | Friesen |
| 5,624,803 A | 4/1997 | Noonberg et al. |
| 5,624,808 A | 4/1997 | Thompson et al. |
| 5,670,633 A | 9/1997 | Cook et al. |
| 5,672,695 A | 9/1997 | Eckstein et al. |
| 5,674,683 A | 10/1997 | Kool |
| 5,712,257 A | 1/1998 | Carter |
| 5,719,271 A | 2/1998 | Cook et al. |
| 5,770,580 A | 6/1998 | Ledley et al. |
| 5,795,715 A | 8/1998 | Livache et al. |
| 5,801,154 A | 9/1998 | Baracchini et al. |
| 5,814,500 A | 9/1998 | Dietz |
| 5,898,031 A | 4/1999 | Crooke |
| 5,908,779 A | 6/1999 | Carmichael et al. |
| 5,919,772 A | 7/1999 | Szyf et al. |
| 5,972,704 A | 10/1999 | Draper et al. |
| 5,998,203 A | 12/1999 | Matulic-Adamic et al. |
| 6,001,990 A | 12/1999 | Wands et al. |

(Continued)

FOREIGN PATENT DOCUMENTS

| | | |
|---|---|---|
| CA | 2359180 A1 | 8/2000 |
| CA | 2432341 A1 | 7/2002 |

(Continued)

OTHER PUBLICATIONS

Monia et al., "Sequence-specific antitumor activity of a phosphorothioate oligodeoxyribonucleotide targeted to human C-raf kinase suports an antisense mechanism of action in vivo", Proc. Natl. Acad. Sci. USA., Dec. 24, 1996, vol. 93, No. 26, pp. 15481-15484.

(Continued)

Primary Examiner — Amy Bowman
(74) Attorney, Agent, or Firm — Lando & Anastasi, LLP

(57) ABSTRACT

The present invention relates to a *Drosophila* in vitro system which was used to demonstrate that dsRNA is processed to RNA segments 21-23 nucleotides (nt) in length. Furthermore, when these 21-23 nt fragments are purified and added back to *Drosophila* extracts, they mediate RNA interference in the absence of long dsRNA. Thus, these 21-23 nt fragments are the sequence-specific mediators of RNA degradation. A molecular signal, which may be their specific length, must be present in these 21-23 nt fragments to recruit cellular factors involved in RNAi. This present invention encompasses these 21-23 nt fragments and their use for specifically inactivating gene function. The use of these fragments (or chemically synthesized oligonucleotides of the same or similar nature) enables the targeting of specific mRNAs for degradation in mammalian cells, where the use of long dsRNAs to elicit RNAi is usually not practical, presumably because of the deleterious effects of the interferon response. This specific targeting of a particular gene function is useful in functional genomic and therapeutic applications.

63 Claims, 15 Drawing Sheets

(56) References Cited

U.S. PATENT DOCUMENTS

| | | |
|---|---|---|
| 6,057,153 A | 5/2000 | George et al. |
| 6,107,094 A | 8/2000 | Crooke |
| 6,218,142 B1 | 4/2001 | Wassenegger et al. |
| 6,225,290 B1 | 5/2001 | German et al. |
| 6,475,726 B1 | 11/2002 | Tally et al. |
| 6,476,205 B1 | 11/2002 | Buhr et al. |
| 6,506,559 B1 | 1/2003 | Fire et al. |
| 6,531,647 B1 | 3/2003 | Baulcombe et al. |
| 6,573,099 B2 | 6/2003 | Graham |
| 6,635,805 B1 | 10/2003 | Baulcombe et al. |
| 6,753,139 B1 | 6/2004 | Baulcombe et al. |
| 6,939,712 B1 | 9/2005 | Bahramian et al. |
| 7,056,704 B2 | 6/2006 | Tuschl et al. |
| 7,078,196 B2 | 7/2006 | Tuschl et al. |
| 7,232,806 B2 | 6/2007 | Tuschl et al. |
| 8,097,710 B2 | 1/2012 | Baulcombe et al. |
| 8,101,584 B2 | 1/2012 | Kreutzer et al. |
| 2002/0086356 A1 | 7/2002 | Tuschl et al. |
| 2002/0114784 A1 | 8/2002 | Li et al. |
| 2002/0132257 A1 | 9/2002 | Giordano et al. |
| 2002/0137210 A1 | 9/2002 | Churikov |
| 2002/0160393 A1 | 10/2002 | Symonds et al. |
| 2002/0162126 A1 | 10/2002 | Beach et al. |
| 2003/0051263 A1 | 3/2003 | Fire et al. |
| 2003/0055020 A1 | 3/2003 | Fire et al. |
| 2003/0056235 A1 | 3/2003 | Fire et al. |
| 2003/0064945 A1 | 4/2003 | Akhtar et al. |
| 2003/0068301 A1 | 4/2003 | Draper et al. |
| 2003/0084471 A1 | 5/2003 | Beach et al. |
| 2003/0108923 A1 | 6/2003 | Tuschl et al. |
| 2003/0140362 A1 | 7/2003 | Macejak et al. |
| 2003/0148985 A1 | 8/2003 | Morrissey et al. |
| 2003/0153521 A1 | 8/2003 | McSwiggen |
| 2003/0171311 A1 | 9/2003 | Blatt et al. |
| 2003/0180756 A1 | 9/2003 | Shi et al. |
| 2003/0190654 A1 | 10/2003 | Heidenreich et al. |
| 2003/0206887 A1 | 11/2003 | Morrissey et al. |
| 2004/0001811 A1 | 1/2004 | Kreutzer et al. |
| 2004/0002153 A1 | 1/2004 | Monia et al. |
| 2004/0005593 A1 | 1/2004 | Lorens |
| 2004/0006035 A1 | 1/2004 | Macejak et al. |
| 2004/0018999 A1 | 1/2004 | Beach et al. |
| 2004/0019001 A1 | 1/2004 | McSwiggen |
| 2004/0038921 A1 | 2/2004 | Kreutzer et al. |
| 2004/0053875 A1 | 3/2004 | Kreutzer et al. |
| 2004/0053876 A1 | 3/2004 | Turner et al. |
| 2004/0054156 A1 | 3/2004 | Draper et al. |
| 2004/0072779 A1 | 4/2004 | Kreutzer et al. |
| 2004/0086884 A1 | 5/2004 | Beach et al. |
| 2004/0096843 A1 | 5/2004 | Rossi et al. |
| 2004/0102408 A1 | 5/2004 | Kreutzer et al. |
| 2004/0121348 A1 | 6/2004 | Kreutzer et al. |
| 2004/0126791 A1 | 7/2004 | Wajant et al. |
| 2004/0137471 A1 | 7/2004 | Vickers et al. |
| 2004/0175703 A1 | 9/2004 | Kreutzer et al. |
| 2004/0191905 A1 | 9/2004 | Stevenson et al. |
| 2004/0192626 A1 | 9/2004 | McSwiggen et al. |
| 2004/0203145 A1 | 10/2004 | Zamore et al. |
| 2004/0214330 A1 | 10/2004 | Waterhouse et al. |
| 2004/0221337 A1 | 11/2004 | Baulcombe et al. |
| 2004/0224328 A1 | 11/2004 | Prydz et al. |
| 2004/0229266 A1 | 11/2004 | Tuschl et al. |
| 2004/0231016 A1 | 11/2004 | Wang et al. |
| 2004/0241854 A1 | 12/2004 | Davidson et al. |
| 2004/0248296 A1 | 12/2004 | Beresford et al. |
| 2004/0248835 A1 | 12/2004 | Krebs et al. |
| 2004/0259247 A1 | 12/2004 | Tuschl et al. |
| 2004/0259248 A1 | 12/2004 | Tuschl et al. |
| 2005/0026278 A1 | 2/2005 | Tuschl et al. |
| 2005/0100907 A1 | 5/2005 | Kreutzer et al. |
| 2005/0234006 A1 | 10/2005 | Tuschl et al. |
| 2005/0234007 A1 | 10/2005 | Tuschl et al. |
| 2005/0282764 A1 | 12/2005 | Bahramian et al. |
| 2005/0282765 A1 | 12/2005 | Hart |
| 2006/0084621 A1 | 4/2006 | Vornlocher |
| 2006/0258608 A1 | 11/2006 | Meyers |
| 2007/0003960 A1 | 1/2007 | Tuschl et al. |
| 2007/0003961 A1 | 1/2007 | Tuschl et al. |
| 2007/0003962 A1 | 1/2007 | Tuschl et al. |
| 2007/0003963 A1 | 1/2007 | Tuschl et al. |
| 2007/0093445 A1 | 4/2007 | Tuschl et al. |
| 2008/0132461 A1 | 6/2008 | Tuschl et al. |
| 2008/0269147 A1 | 10/2008 | Tuschl et al. |
| 2009/0155174 A1 | 6/2009 | Tuschl et al. |
| 2009/0186843 A1 | 7/2009 | Tuschl et al. |
| 2010/0010207 A1 | 1/2010 | Tuschl et al. |
| 2010/0292456 A1 | 11/2010 | Tuschl et al. |
| 2010/0316703 A1 | 12/2010 | Tuschl et al. |
| 2011/0014123 A1 | 1/2011 | Tuschl et al. |
| 2011/0020234 A1 | 1/2011 | Tuschl et al. |
| 2011/0027883 A1 | 2/2011 | Tuschl et al. |
| 2011/0054159 A1 | 3/2011 | Tuschl et al. |
| 2011/0065109 A1 | 3/2011 | Tuschl et al. |
| 2011/0065773 A1 | 3/2011 | Tuschl et al. |
| 2011/0070162 A1 | 3/2011 | Tuschl et al. |
| 2011/0112283 A1 | 5/2011 | Tuschl et al. |
| 2011/0244446 A1 | 10/2011 | Tuschl et al. |
| 2011/0244568 A1 | 10/2011 | Tuschl et al. |
| 2011/0245318 A1 | 10/2011 | Tuschl et al. |
| 2011/0281931 A1 | 11/2011 | Tuschl et al. |
| 2011/0289611 A1 | 11/2011 | Tuschl et al. |
| 2011/0306651 A1 | 12/2011 | Tuschl et al. |
| 2012/0015042 A1 | 1/2012 | Tuschl et al. |
| 2012/0029061 A1 | 2/2012 | Tuschl et al. |
| 2012/0122111 A1 | 5/2012 | Tuschl et al. |
| 2013/0125259 A1 | 5/2013 | Tuschl et al. |
| 2013/0198875 A1 | 8/2013 | Tuschl et al. |

FOREIGN PATENT DOCUMENTS

| | | |
|---|---|---|
| CA | 2432350 A1 | 7/2002 |
| DE | 19956568 A1 | 8/2000 |
| DE | 10160151.4 A1 | 12/2001 |
| DE | 10100586 C1 | 4/2002 |
| DE | 20023125 U1 | 5/2003 |
| DE | 10160151 A1 | 6/2003 |
| EP | 303516 B1 | 2/1989 |
| EP | 0649467 A1 | 4/1995 |
| EP | 0650493 A1 | 5/1995 |
| EP | 0649467 B1 | 9/1998 |
| EP | 0983370 B1 | 3/2000 |
| EP | 0126325.0 | 12/2000 |
| EP | 1144623 B1 | 10/2001 |
| EP | 1214945 A2 | 6/2002 |
| EP | 1309726 B1 | 5/2003 |
| EP | 1352061 A2 | 10/2003 |
| EP | 1407044 B1 | 4/2004 |
| EP | 1230375 B1 | 7/2005 |
| EP | 2348133 A1 | 7/2011 |
| EP | 2348134 A1 | 7/2011 |
| EP | 2351852 A1 | 8/2011 |
| GB | 9827152.1 | 12/1998 |
| GB | 2349885 A | 11/2000 |
| GB | 2353282 A | 2/2001 |
| GB | 2362885 A | 12/2001 |
| GB | 2370275 A | 6/2002 |
| RU | 2322500 C2 | 4/2008 |
| WO | 9110671 A1 | 7/1991 |
| WO | 9219732 A1 | 11/1992 |
| WO | 9401550 A1 | 1/1994 |
| WO | 9415645 A1 | 7/1994 |
| WO | 9421767 A1 | 9/1994 |
| WO | 9507981 A1 | 3/1995 |
| WO | 9640964 A2 | 12/1996 |
| WO | 9711170 A1 | 3/1997 |
| WO | 9743431 A1 | 11/1997 |
| WO | 9746570 A1 | 12/1997 |
| WO | 9805770 A2 | 2/1998 |
| WO | 9853083 A1 | 11/1998 |
| WO | 9914226 A2 | 3/1999 |
| WO | 9915682 A2 | 4/1999 |
| WO | 9932619 A1 | 7/1999 |
| WO | 9949029 A1 | 9/1999 |
| WO | 9953050 A1 | 10/1999 |

(56) References Cited

FOREIGN PATENT DOCUMENTS

| WO | 9954459 | A2 | 10/1999 |
|---|---|---|---|
| WO | 9961631 | A1 | 12/1999 |
| WO | 0001846 | A2 | 1/2000 |
| WO | 0031271 | A1 | 6/2000 |
| WO | 0032619 | A1 | 6/2000 |
| WO | 0044895 | A1 | 8/2000 |
| WO | 0044914 | A1 | 8/2000 |
| WO | 0063364 | A2 | 10/2000 |
| WO | 0063364 | A3 | 10/2000 |
| WO | 0136646 | A1 | 5/2001 |
| WO | 0168826 | A2 | 9/2001 |
| WO | 0168836 | A2 | 9/2001 |
| WO | 0175164 | A2 | 10/2001 |
| WO | 0192513 | A1 | 12/2001 |
| WO | 0244321 | A2 | 6/2002 |
| WO | 02055692 | A2 | 7/2002 |
| WO | 02055692 | A3 | 7/2002 |
| WO | 02055693 | A2 | 7/2002 |
| WO | 02059300 | A2 | 8/2002 |
| WO | 02059300 | A3 | 8/2002 |
| WO | 02061034 | A2 | 8/2002 |
| WO | 03029459 | A2 | 4/2003 |
| WO | 03033700 | A1 | 4/2003 |
| WO | 03035869 | A1 | 5/2003 |
| WO | 03062394 | A2 | 7/2003 |
| WO | 03064621 | A2 | 8/2003 |
| WO | 03099298 | A1 | 12/2003 |
| WO | 03103600 | A2 | 12/2003 |
| WO | 03106630 | A2 | 12/2003 |
| WO | 03106631 | A2 | 12/2003 |
| WO | 2004007718 | A2 | 1/2004 |
| WO | 2004014933 | A1 | 2/2004 |
| WO | 2004015107 | A2 | 2/2004 |
| WO | 2004027030 | A2 | 4/2004 |
| WO | 2004029212 | A2 | 4/2004 |
| WO | 2004042029 | A2 | 5/2004 |
| WO | 2004044131 | A2 | 5/2004 |
| WO | 2004045543 | A2 | 6/2004 |
| WO | 2004046324 | A2 | 6/2004 |
| WO | 2004063375 | A1 | 7/2004 |
| WO | 2004065600 | A2 | 8/2004 |
| WO | 2004065613 | A2 | 8/2004 |
| WO | 2004076622 | A2 | 9/2004 |
| WO | 2004111191 | A2 | 12/2004 |

OTHER PUBLICATIONS

Montgomery et al., "Double-stranded RNA as a mediator in sequence-specific genetic silencing and co-suppression", TIG, Jul. 1998, vol. 14, No. 7, pp. 255-258.

Montgomery et al., "RNA as a target of double-stranded RNA-mediated genetic interferece in Caenorhabditis elegans", Proc. Natl. Acad. Sci. USA, 1998, vol. 95, pp. 15502-15507.

Morita et al., "Antisense oligonucleotides targeting c-fos mRNA inhibit rheumatoid synovial fibroblast proliferation", Ann. Rheum. Dis., 1998, vol. 57, pp. 122-124.

Morita et al., "RNAi provides a new tool for functional analyses of mammalian genes", Proteins, Nucleic Acids and Enzymes, 2002, vol. 47, No. 14, pp. 1939-1945.

Moss et al., "MicroRNAs: something new under the sun", Current Biology., 2002, vol. 12, pp. R688-R690.

Moss, "Non-coding RNAs: Lightning strikes twice", Current Biology, 2000, vol. 10, pp. R436-R439.

Moss, E. G. et al: "The Cold Shock Domain Protein LIN-28 Controls Developmental Timing in C. elegans and Is Regulated by the lin-4 RNA", Cell, vol. 88, Mar. 7, 1997, 637-646.

Mourelatos et al., "miRNPs: a novel class of ribmucleoproteins containing numerous microRNAs", Gene and Develpoment, 2002, vol. 16, pp. 720-728.

Mourrain et al., "Arabidopsis SGS2 and SGS3 genes required for posttranscriptional gene silencing and natural virus resistance", Cell, 2000, vol. 101, pp. 533-542.

Myers et al., "Recombinant dicer efficiently converts large dsRNAs into siRNAs suitable for gene silencing", Nature Biotechnology, 2003, vol. 21, pp. 324-328.

Nakamura, H. et al.: "How does RNase H recognize a DNA-RNA hybrid", Proc. Natl. Acad. (1991), vol. 88, pp. 11535-11539.

Nakano et al., "RNA interference for the organizer-specific gene Xlim-1 in Xenopus embryos", Biochem. Biophys. Res. Commun., 2000, vol. 274, pp. 434-439.

Nanduri, S. et al.: "Structure of the double-stranded RNA-binding domain of the protein kinase PKR reveals the molecular basis of its dsRNA-mediated activation", The EMBO Journal, vol. 17, No. 18, pp. 5458-5465 (1998).

Napoli, C. et al.: "Introduction of a Chimeric Chalcone Synthase Gene into Petunia Results in Reversible Co-Suppression of Homologous Genes in trans", The Plant Cell, vol. 2, Apr. 1990, pp. 279-289.

Ngo et al., "Double-stranded RNA induces mRNA degradation in Trypanosoma brucei", Proc. Natl. Acad. Sci. USA, Dec. 1998, vol. 95, pp. 14687-14692.

Nguyen et al., "RNAi therapeutics: an update on delivery", Curr. Opin. Mol. Ther., Apr. 2008, vol. 10, No. 2, pp. 158-167, Review.

Nicholson, "Function, mechanism and regulation of bacterial ribonucleases", FEMS Microbiology Reviews, 1999, vol. 23, pp. 371-390.

Nielsen P. et al: "A novel class of conformationally restricted oligonucleotide analogues: synthesis of 2',3'-bridged monomers and RNA-selective hybridisation", J. Chem. Commun. 1997; pp. 825-826.

Nikiforov, T. T. and B. A. Connolly: "Oligodeoxynucleotides containing 4-thiothymidine and 6-thiodeoxyguanosine as affinity labels for the Eco RV restriction endonuclease and modification methylase", Nucleic Acids Res, Mar. 25, 1992, vol. 20, No. 6, pp. 1209-1214.

Nishikura, "A short primer on RNAi: RNA-directed RNA polymerase acts as a key catalyst", Cell, 2001, vol. 107, pp. 415-418.

Nishina et al., "Efficient in vivo delivery of siRNA to the liver by conjugation of a-tocopherol", Mol. Ther., Apr. 2008, vol. 16, No. 4, pp. 734-740, Epub Feb. 12, 2008.

Notice of Opposition to European Patent No. EP 1 144 623 and Opposition papers filed in EPO by Atugen AG on May 28, 2003.

Notice of Opposition to European Patent No. EP 1 144 623 and Opposition papers filed in EPO by Janssen Pharmaceutica N.W. on May 28, 2003.

Novina et al., "The RNAi revolution", Nature, Jul. 8, 2004, vol. 430, No. 6996, pp. 161-164.

Nykanen et al., "ATP requirements and small interfering RNA structure in the RNA interference pathway", Cell, Nov. 2, 2001, vol. 107, No. 3, pp. 309-321.

Oates, A. C. et al.: Too Much Interference: Injection of Double-Stranded RNA Has Nonspecific Effects in the Zebrafish embryo, Developmental Biology, vol. 224, 2000, pp. 20-28.

Oelgeschlager et al., "The evolutionarily conserved BMP-binding protein twisted gastrulation promotes BMP signalling", Nature, 2000, vol. 405, pp. 757-763.

Opposition Document Reason for Filing—Japanese Patent Application 2001-573036.

Opposition paper submitted by BASF (Opponent 3) in EP1309726, dated Sep. 2, 2010.

Opposition paper submitted by BASF SE (Opponent 4) in EP 1407044 dated Jun. 19, 2008.

Opposition paper submitted by Pfizer (Opponent 2) in EP 1407044, dated Jun. 19, 2008.

Opposition paper submitted by Sanofi-Aventis (Opponent 1) in EP1309726, Sep. 2, 2010.

Opposition paper submitted by Sarah E. Rogues (Opponent 3) in EP1407044 dated Jun. 18, 2008.

Opposition paper submitted by Silence Therapeutics (Opponent 2) in EP1309726, dated Sep. 2, 2010.

Opposition paper submitted by Silence Therapeutics (Opponent 5) in EP1407044 dated Jun. 19, 2008.

Opposition paper submitted by Sirna Therapeutics (Opponent 1) in EP 1407044, dated Jun. 10, 2008.

(56) References Cited

OTHER PUBLICATIONS

Opposition submission dated Nov. 10, 2010 regarding European Patent No. 1 407 044 (Application No. 01985833.1), opposed by Sirna Therapeutics, Inc. (Opponent 1), 7 pages.
Opposition submission dated Sep. 29, 2010 regarding European Patent No. 1 407 044 (Application No. 01985833.1), opposed by Pfizer Inc. (Opponent 2), 47 pages.
Paddison et al., "Short hairpin RNAs (shRNAs) induced sequence-specific silencing in mammalian cells", Genes & Development, vol. 16, pp. 948-958.
Paddison et al., "Stable suppression of gene expression by RNAi in mammalian cells", PNAS, 2002 vol. 99, No. 3, pp. 1443-1448.
Pal-Bhadra et al., "Cosuppression of nonhomologous transfenes in *Drosophila* Involves mutually related endogenous sequences", Cell, Oct. 1999, vol. 99, pp. 35-46.
Pan et al., "In vitro selection of RNAs that undergo autolytic cleavage with Pb2+", Biochemistry, 1992, vol. 31, No. 16, pp. 3887-3895.
Papers filed in EPO in opposition to European Patent No. EP 1 144 623 by Aventis Pharma Deustschland GmbH on May 28, 2003.
Papers filed in EPO in opposition to European Patent No. EP 1 144 623 by Dr. Martin Grund on May 28, 2003.
Papers filed in EPO in opposition to European Patent No. EP 1 144 623 by SiRNA Therapeutics Inc. on May 19, 2003.
Park et al., "Double-stranded siRNA targeted to the huntingtin gene does not induce DNA methylation", 2004, Biochemical and Biophysical Research Communications, vol. 323, pp. 275-280.
Parker et al., "Structural insights into mRNA recognition from a PIWI domain-siRNA guide complex", Nature, Mar. 31, 2005, vol. 434, No. 7033, pp. 663-666.
Parrish et al., "Distinct roles for RDE-1 and RDE-4 during RNA interference in *Caenorhabditis elegans*", RNAa, 2001, vol. 7, pp. 1397-1402.
Parrish et al., "Functional anatomy of a dsRNA trigger: differential requirement for the two trigger strands in RNA interference", Mol. Cell, 2000, vol. 6, pp. 1077-1087.
Partial English translation of the Written Demand for Invalidation Trial against Japanese Patent No. 4095895, dated Jul. 8, 2011.
Partial European Search Report mailed Sep. 27, 2007 for Application No. 07014533.
Pasquinelli et al., "Conservation of the sequence and temporal expression of let-7 heterochronic regulatory RNA", Nature, Nov. 2, 2000, vol. 408, pp. 86-89.
Patentee's main request and counterargument to the opponents objections in EP1407044, dated Mar. 26, 2009.
Patentee's submission regarding opposition for EP 1407044 (01985833.1) dated Oct. 1, 2010, 85 pages.
Paul et al., "Effective expression of small interfering RNA in human cells", Nature Biotechnology, May 2002, vol. 29, pp. 505-508.
Pegram, M. D. et al.: "Phase II Study of Receptor-Enhanced Chemosensitivity Using Recombinant Humanized Anti-p185HER2/neu Monoclonal Antibody Plus Cisplatin in Patients With HER2-neu Overexpressing Metastasic Breast Cancer Refractory to Chemotherapy Treatment", J. Clin. Oncol. Aug. 1998, vol. 16, No. 8, pp. 2659-2671.
Pei, Y. and T. Tuschl: "On the art of identifying effective and specific siRNAs", Nature Methods, vol. 3, No. 9, Sep. 2006, pp. 670-676.
Pelissier et al., "A DNA target of 30 by is sufficient for RNA-directed methylation", RNA, 2000, vol. 6, pp. 55-65.
Pellino et al., "ATP modulates siRNA interactions with an endogenous human Dicer comples", RNA, 2005, vol. 11, pp. 1719-1724.
Perler, F. B.: "InBase: the Intein Database", New England Biolabs Inc., Nucleic Acids Research 2002, vol. 30, No. 1, 383-384.
Persengiev et al., "Nonspecific, concentration-dependent stimulation and repression of mammalian gene expression by small interfering RNAs (siRNAs)", RNA, 2004, vol. 10, pp. 12-18.
Pfeffer et al., "RNA silencing," B.I.F. Fugura, 2005, vol. 20, pp. 83-91.
Phillips, "Antisense inhibition and adeno-associated viral vector delivery for reducing hypertension", Hypertension, Jan. 1997, vol. 29 (Part 1, Part 2), pp. 177-187.
Pillai et al., "Repression of protein synthesis by miRNAs: how many mechanisms?", Trends in Cell Biology, vol. 17, No. 3, pp. 118-126.
Plaintiffs' Complaint. Civil Action No. 09-2654. *Max-Planck-Gesellschaft zur Forderung der Wissenschaften e.V. v. Wolf Greenfield & Sacks, PC*. Dated Jun. 26, 2009.
Plaintiffs' Ex Parte Motion for a Short Order of Notice. Civil Action No. 09-2674-BLS. *Max Planck-Gesellschaft zur Forderung der Wissenschaften Ev. v. Whitehead Institute for Biomedical Research, et al*. Dated Jun. 30, 2009.
Plaintiffs' Motion for Preliminary Injunction. Civil Action No. 09-2674-BLS. *Max-Planck Gesellschaft zur Forderung der Wissenschaften e.V. v. Whitehead Institute for Biomedical Research, et al*. Dated Jun. 30, 2009.
Plantiffs' Ex Parte Motion for Temporary Restraining Order. Civil Action No. 09-2674-BLS. *Max Planck-Gesellschaft zur Forderung der Wissenschaften e.V. v. Whitehead Institute for Biomedical Research, et al*. Dated Jun. 30, 2009.
Plasterk et al., "The silences of the genes", Curr. Opin. Genet., Dev., 2000, vol. 10, pp. 562-567.
Plasterk, "RNA silencing: the genome's immune system", Science, May 17, 2002, vol. 296, pp. 1263-1265.
Preliminary and non-binding opinion issued by Opposition Division regarding EP1407044, dated May 6, 2010.
Press Release, Nov. 15, 2001, "AGY Therapeutics Announces Study Demonstrating Utility of RNA Interference in Mammalian Cells for CNS Drug Discovery".
Case 1:09-cv-11116-PBS. Transcript of Hearing on Jul. 1, 2009.
Ratcliff et al., "Gene silencing without DNA. RNA-mediated cross-protection between viruses", Plant Cell, 1999, vol. 11, pp. 1207-1216.
Razin, "CpG methylation, chromatic structure and gene silencing—a three-way connection", EMBO Journal, 1998, vol. 17, No. 17, pp. 4905-4908.
Register extract for WO 01/75164 (printed Feb. 18, 2008).
Reich et al., "Small interfering RNA (siRNA) targeting VEGF effectively inhibits ocular neovascularization in a mouse model", Molecular Vision, 2003, vol. 9, pp. 210-216.
Reinhart et al., "The 21-nucleotide let-7 RNA regulates developmental timing in *Caenorhabditis elegans*", Nature, Feb. 24, 2000, vol. 403, pp. 901-906.
Reply Brief filed by the patentee to dismiss the Appeals in the opposition proceedings in EP1407044, dated Nov. 10, 2011.
Reprint of Thomas Tuschl's email dated Apr. 5, 2000 (printed Jan. 11, 2010).
Response to Notice of Opposition against EP1309726, filed by patentee, dated Jul. 4, 2011.
Robertson, "*Escherichia coli* ribonuclease III cleavage sites", Cell, 1982, vol. 30, pp. 669-672.
Robertson, "*Escherichia coli* ribonuclease III", Methods Enzymol., 1990, vol. 181, pp. 189-202.
Robinson, "RNAi therapeutics: how likely, how soon?", Plas Biology, Jan. 2004, vol. 2, No. 1, pp. 18-20.
Roitt et al., Immunology, Third Edition, 1993, p. 15.8.
Romaniuk et al., "The effect of acceptor oligoribonucleotide sequence on the T4 RNA ligase reaction", Eur. J. Biochem., 1982, vol. 125, pp. 639-643.
Roshak et al, "Manipulation of distinct NFKB proteins alters interleukin-113-induced human rheumatoid synoval fibroblast prostaglandin E2 formation", J. Biological Chemistry, 1996, vol. 271, No. 49, pp. 31496-31501.
Rossi et al., "RNAi and the P-body connection", Nat. Cell Biol., Jul. 2005, vol. 7, No. 7, pp. 643-644.
Rotondo et al., "Substrate structure requirements of the PAC1 rebonuclease from *Schizosaccharomyces pombe*", RNA, 1997, vol. 3, pp. 1182-1193.
Rouget, "Nominations", Mar. 26, 2009, pp. 792-795.
Ruvkun, "Glimpses of a tiny RNA world", Science, 2001, vol. 294, pp. 797-799.
Samarsky et al., "RNAi in drug development: Practical considerations", RNA Interference Technology, 2005, pp. 384-395.

(56) References Cited

OTHER PUBLICATIONS

Sanchez-Alvarado et al., "Double-stranded RNA specifically disrupts gene expression during planarian regeneration", Proc. Natl. Acad. Sci. USA, 1999, vol. 96, pp. 5049-5054.
Schaefer, "Revolutions in rapid amplification of cDNA ends: new strategies for polymerase chain reaction cloning of full-length cDNA ends", Analytical Biochemistry, 1996, vol. 227, pp. 255-273.
Scherer et al., "Approaches for the sequence-specific knockdown of mRNA", Nat. Biotechnol., 2003, vol. 21, No. 12, pp. 1457-1465.
Schiebel et al., "Isolation of an RNA-directed RNA polymerase-specific cDNA clone from tomato", Plant Cell, 1998, vol. 10, pp. 2087-2101.
Schmidt, "Negotiating the RNAi patent thicket", Nat. Biotechnol., Mar. 2007, vol. 25, No. 3, pp. 273-275, Epub Mar. 1, 2007.
Schmitter et al., "Effects of dicer and argonaute down-regulation on mRNA levels in human HEK293 cells", Nucleic Acids Research, 2006, vol. 34, No. 17, pp. 4801-4815.
Schmitz et al., "Effect of 2'-0-methyl antisense ORNs on expression of thymidylate synthase in human colon cancer RKO cells", Nucleic Acids Research, 2001, vol. 29, No. 2, pp. 415-422.
Schramke et al., "Those interfering little RNAs! Silencing and eliminating chromatin", Curr. Opin. Genet. Dev., Apr. 2004, vol. 14, No. 2, pp. 174-180.
Schwartz et al., "Why do miRNAs live in the miRNP?", Genes Dev., May 1, 2002, vol. 16, No. 9, pp. 1025-1031.
Schwarz et al, "Evidence that siRNAs function as guides, not primers, in the *Drosophila* and human RNAi pathways", Molecular Cell, 2002, vol. 10, pp. 537-548.
Schwarz et al., "Asymmetry in the assembly of the RNAi enzyme complex", Cell, 2003, vol. 115, pp. 199-208.
Schweizer et al., "Double-stranded RNA interferes with gene function at the single-cell level in cereals," The Plant Journal, 2000, vol. 24, No. 6, pp. 895-903.
Sharp et al., "RNA interference", Science, Mar. 2000, vol. 287, pp. 2431-2433.
Sharp, "RNA interference-2001", Genes and Development, 2001, vol. 15, pp. 485-490.
Sharp, "RNAi and double-strand RNA", Genes & Development, Jan. 15, 1999, vol. 13, No. 2, pp. 139-140.
Shi Y. and C. Mello: "A CBP/p300 homolog specifies multiple different pathways in *Caenorhabditis elegans*", Genes & Development, vol. 12, No. 7, pp. 943-955, Apr. 1, 1998.
Shi, "Mammalian RNAi for the masses", Trends in Genetics, 2003, vol. 19, No. 1, pp. 9-12.
Shiota et al., "I want to know the RNAi protocol of that animal!—effective RNAi in mammal cells", Cell Engineering, 2003, vol. 22, No. 3, pp. 310-315.
Sijen et al., "Post-transcriptional gene-silencing: RNAs on the attack or on the defense", BioEssays, 2000, vol. 22, pp. 520-531.
Sijen, et al., "On the role of RNA amplification in dsRNA-triggered gene silencing", Cell, Nov. 16, 2001, vol. 107, pp. 465-476.
Simeoni et al., "Peptide-based strategy for siRNA delivery into mammalian cells", Methods in Molecular Biology, 2005, vol. 309, pp. 251-260.
Siomi et al., "RNA interference: a new mechanism by which FMRP acts in the normal brain? What can *Drosophila* teach us?", Ment. Retard Dev. Disabil. Res. Rev., 2004, vol. 10, No. 1, pp. 68-74.
Sioud et al., "High-throughput analysis of microRNA gene espression using sensitive probes", RNA Silencing: Methods and Protocols, 2005, vol. 309, pp. 311-320, Humana Press.
Sioud et al., "Therapeutic siRNAs", Trends Pharmacol. Sci., Jan. 2004, vol. 25, No. 1, pp. 22-28.
Sioud in RNA Silencing, Methods and Protocols, (Humana Press, 2005).
Sioud, "siRNA delivery in vivo", Methods in Molecular Biology, 2005, vol. 309, pp. 237-249.
Skipper et al., "Elegant tour de force", Nature Reviews Genetics, 2003, vol. 4, pp. 79-80.
Skipper et al., "Have our dreams been shattered?", Nature Reviews Genetics, 2003, vol. 4, pp. 671.
Skripkin, E. et al.: "Psoralen crosslinking between human immunodeficiency virus type 1 RNA and primer tRNA3Lys", Nucleic Acids Research, 1996, vol. 24, No. 3, pp. 509-514.
Skyba et al., "Direct in vivo visualization of intravascular destruction of microbubbles by ultrasound and its local effects on tissue", Circulation, 1998, vol. 98, pp. 290-293.
Slack et al., "The lin-41 RBCC gene acts in the *C.elegans* heterochronic pathway between the let-7 regulatory RNA and the LIN-29 transcription factor", Mol. Cell, Apr. 2000, vol. 5, No. 4, pp. 659-669.
Sledz, C. A. et al.: "Activation of the interferon system by short-interfering RNAs", Nature Cell Biology, vol. 5, No. 9, pp. 834-839, Sep. 2003.
Smardon et al., "EGO-1 is related to RNA-directed RNA polymerase and functions in germ-line development and RNA interference in *C. elegans*", Current Biology, Feb. 2000, vol. 10, No. 4, pp. 169-178.
Smith et al., "Total silencing by intron-spliced hairpin RNAs", Nature, 2000, vol. 407, pp. 319-320.
Smyth et al., "Gene silencing: cosuppression at a distance", Curr. Biol., Dec. 1, 1997, vol. 7, No. 12, pp. R793-R795.
Song et al., "RNA interference targeting Fas protects mice from fulminant hepatitis", Nature Medicine, 2003, vol. 9, No. 3, pp. 347-351.
Sontheimer et al., "Assembly and function of RNA silencing complexes", Nat. Rev. Mol. Cell Biol., Feb. 2005, vol. 6, No. 2, pp. 127-138.
Soutschek et al., "Therapeutic silencing of an endogenous gene by systemic administration of modified siRNAs", Nature, 2004, vol. 432, pp. 173-178.
Soutschek, J. et al.: "Therapeutic silencing of an endogenous gene by systemic administration of modified siRNAs", Nature, Nov. 11, 2004, vol. 432, pp. 173-178.
Stark et al., "How cells respond to interferons", Anne. Rev. Biochem., 1998, vol. 67, pp. 227-264.
Steinberg, "MicroRNA shows macro potential", The Scientist, Jun. 16, 2003, vol. 17, No. (12, 22), pp. 1-9.
Stipp, "Biotech's billion dollar breakthrough", Fortune, retrieved online http://money.cnn.com/magazines/fortune/fortune_archive/2003/05/23/343099/, 2002.
Storz, "An expanding universe of noncoding RNAs", Science, May 17, 2002, vol. 296, pp. 1260-1262.
Stratagene pBluescript II Phagemid Vectors Instruction Manual for Catalog # 212207, downloaded from the Stratagene, Inc. website on Jan. 11, 2007.
Strauss, "Candidate 'gene silencers' found", Science, Oct. 29, 1999, vol. 286, pp. 886.
Stäeuber et al., "Bluetongue virus VP6 protein binds ATP and exhibits an RNA-dependent ATPase function and a helicase activity that catalyze the unwinding of double-stranded RNA substates", Journal of Virology, Oct. 1997, pp. 7220-7226.
Sui et al., "A DNA vector-based RNAi technology to suppress gene expression in mammalian cells", Apr. 16, 2002, vol. 99, No. 8, pp. 5515-5520.
Svoboda et al., "Lack of homologous sequence-specific DNA methylation in response to stable dsRNA expression in mouse oocytes", Nucleic Acid Reseach, 2004, vol. 32, No. 12, pp. 3601-3606.
Svoboda et al., "Selective reduction of dormant maternal mRNAs in mouse oocytes by RNA interference", Development, 2000, vol. 127, pp. 4147-4156.
Szweykowska-Kulihska et al., "RNA interference and its role in the regulation of eucaryotic gene expression", Acta Biochimica Polonica, 2003, vol. 50, No. 1, pp. 217-229.
Tabara et al., "RNAi in *C. elegans*: soaking in the genome sequence", Science, Oct. 16, 1998, vol. 282, pp. 430-431.
Tabara et al., "The dsRNA binding protein RDE-4 interacts with RDe-1, DCR-1, and a DExH-Box helicase to direct RNAi in *C. elegans*", Cell, 2002, vol. 109, pp. 861-871.
Tabara et al., "The rde-1 gene, RNA interference, and transposon silencing in *C. elegans*", Cell, Oct. 1999, vol. 99, pp. 123-132.
Case 1:11-cv-10484-PBS *The University of Utah v. Max-Planck-Gesellschaft zur Forderung der Wissenschaften E.V.*—Document 1—Plaintiff's complaint filed Mar. 22, 2011.

(56) References Cited

OTHER PUBLICATIONS

Case1:11-cv-10484-PBS—Document 1-1—Exhibit 1 associated with plaintiff's complaint, filed Mar. 22, 2011.
Case1:11-cv-10484-PBS—Document 1-10—Exhibit 10 associated with plaintiff's complaint, filed Mar. 22, 2011.
Case1:11-cv-10484-PBS—Document 1-11—Exhibit 11 associated with plaintiff's complaint, filed Mar. 22, 2011.
Case1:11-cv-10484-PBS—Document 1-12—Exhibit 12 associated with plaintiff's complaint, filed Mar. 22, 2011.
Case1:11-cv-10484-PBS—Document 1-13—Exhibit 13 associated with plaintiff's complaint, filed Mar. 22, 2011.
Case1:11-cv-10484-PBS—Document 1-14—Exhibit 14 associated with plaintiff's complaint, filed Mar. 22, 2011.
Case1:11-cv-10484-PBS—Document 1-15—Exhibit 15 associated with plaintiff's complaint, filed Mar. 22, 2011.
Case1:11-cv-10484-PBS—Document 1-16—Exhibit 16 associated with plaintiff's complaint, filed Mar. 22, 2011.
Case1:11-cv-10484-PBS—Document 1-17—Exhibit 17 associated with plaintiff's complaint, filed Mar. 22, 2011.
Case1:11-cv-10484-PBS—Document 1-18—Exhibit 18 associated with plaintiff's complaint, filed Mar. 22, 2011.
Case1:11-cv-10484-PBS—Document 1-19—Exhibit 19 associated with plaintiff's complaint, filed Mar. 22, 2011.
Case1:11-cv-10484-PBS—Document 1-2—Exhibit 2 associated with plaintiff's complaint, filed Mar. 22, 2011.
Case1:11-cv-10484-PBS—Document 1-20—Exhibit 20 associated with plaintiff's complaint, filed Mar. 22, 2011.
Case1:11-cv-10484-PBS—Document 1-21—Exhibit 21 associated with plaintiff's complaint, filed Mar. 22, 2011.
Case1:11-cv-10484-PBS—Document 1-22—Exhibit 22 associated with plaintiff's complaint, filed Mar. 22, 2011.
Case1:11-cv-10484-PBS—Document 1-23—Exhibit 23 associated with plaintiff's complaint, filed Mar. 22, 2011.
Case1:11-cv-10484-PBS—Document 1-24—Exhibit 24 associated with plaintiff's complaint, filed Mar. 22, 2011.
Case1:11-cv-10484-PBS—Document 1-25—Exhibit 25 associated with plaintiff's complaint, filed Mar. 22, 2011.
Case1:11-cv-10484-PBS—Document 1-26—Exhibit 26 associated with plaintiff's complaint, filed Mar. 22, 2011.
Case1:11-cv-10484-PBS—Document 1-27—Exhibit 27 associated with plaintiff's complaint, filed Mar. 22, 2011.
Case1:11-cv-10484-PBS—Document 1-28—Exhibit 28 associated with plaintiff's complaint, filed Mar. 22, 2011.
Case1:11-cv-10484-PBS—Document 1-29—Exhibit 29 associated with plaintiff's complaint, filed Mar. 22, 2011.
Case1:11-cv-10484-PBS—Document 1-3—Exhibit 3 associated with plaintiff's complaint, filed Mar. 22, 2011.
Case1:11-cv-10484-PBS—Document 1-30—Exhibit 30 associated with plaintiff's complaint, filed Mar. 22, 2011.
Case1:11-cv-10484-PBS—Document 1-31—Exhibit 31 associated with plaintiff's complaint, filed Mar. 22, 2011.
Case1:11-cv-10484-PBS—Document 1-4—Exhibit 4 associated with plaintiff's complaint, filed Mar. 22, 2011.
Case1:11-cv-10484-PBS—Document 1-5—Exhibit 5 associated with plaintiff's complaint, filed Mar. 22, 2011.
Case1:11-cv-10484-PBS—Document 1-6—Exhibit 6 associated with plaintiff's complaint, filed Mar. 22, 2011.
Case1:11-cv-10484-PBS—Document 1-7—Exhibit 7 associated with plaintiff's complaint, filed Mar. 22, 2011.
Case1:11-cv-10484-PBS—Document 1-8—Exhibit 8 associated with plaintiff's complaint, filed Mar. 22, 2011.
Case1:11-cv-10484-PBS—Document 1-9—Exhibit 9 associated with plaintiff's complaint, filed Mar. 22, 2011.
Case1:11-cv-10484-PBS—Document 30. Defendants' Motion to Dismiss the University of Utah's First Amended Complaint. Filed Oct. 31, 2011.
Case1:11-cv-10484-PBS—Document 31. Memorandum in Support of Defendants' Motion to Dismiss the University of Utah's First Amended Complaint. Filed Oct. 31, 2011.
Case1:11-cv-10484-PBS—Document 32. Declaration of Alan J. Heinrich with Exhibits 1-3. Filed Oct. 31, 2011.
Case1:11-cv-10484-PBS—Document 33. University of Massachusetts' Motion to Dismiss University of Utah's First Amended Complaint. Filed Oct. 31, 2011.
Case1:11-cv-10484-PBS—Document 34. Memorandum in Support of University of Massachusetts' Motion to Dismiss University of Utah's First Amended Complaint. Filed Oct. 31, 2011.
Case1:11-cv-10484-PBS—Document 41. Plaintiff's Unopposed Motion for Leave to Amend Complaint. Filed Dec. 22, 2011.
Case1:11-cv-10484-PBS—Document 42. Second Amended Complaint. Filed Dec. 27, 2011.
Case1:11-cv-10484-PBS—Document 54. Defendants' Motion to Dismiss the University of Utah's Second Amended Complaint. Filed Feb. 10, 2012.
Case1:11-cv-10484-PBS—Document 55. Memorandum in Support of Defendants' Motion to Dismiss the University of Utah's Second Amended Complaint. Filed Feb. 10, 2012.
Case1:11-cv-10484-PBS—Document 56. Declaration of Alan J. Heinrich with Exhibits 1-3. Filed Feb. 10, 2012.
Case1:11-cv-10484-PBS—Document 8. First Amended Complaint. Filed Jul. 6, 2011.
Castanotto et al., "Functional siRNA expression from transfected PCR products", RNA, 2002, vol. 8, pp. 1454-1460.
Catalanotto et al., "Gene silencing in worms and fungi", Nature, Mar. 16, 2000, vol. 404, pp. 245.
Celotto et al., "Exon-specific RNAi: A tool for dissecting the functional relevance of alternative spleing", RNA, 2002, vol. 8, pp. 718-724.
Cerutti et al., "Domains in gene silencing and cell differentiation proteins: the novel PAZ domain and redefinition of the PiWi domain", TIBS, Oct. 25, 2000, pp. 481-482.
Chanfreau et al., "Recognition of a conserved class of RNA tetraloops by *Saccharomyces cerevisiae* RNase III", Proc. Natl. Acad. Sci. USA, 1997, vol. 97, pp. 3143-3147.
Check et al., "Gene regulation: RNA to the rescue?", Nature, Sep. 4, 2003, vol. 425, No. 6953, pp. 10-12.
Chen, M. et al.: "A universal plasmid library encoding all permutations of small interfering RNA", PNAS, 2005, vol. 102, pp. 2356-2361.
Elela et al., "Depletion of yeast Rnase III blocks correct U2 3' end formation and results in polydenylated but functional U2 snRNA", The EMBO Journal, 1998, vol. 17, No. 13, pp. 3738-3746.
Elmen et al., "Locked nucleic acids (LNA) mediated improvements in siRNA stability and functionality", Nucleic Acids Research, 2005, vol. 33, No. 1, pp. 439-447.
Escobar et al., "RNAi-mediated oncogene silencing confers resistance to crown gall tumorigenesis", PNAS, Nov. 6, 2001, vol. 98, No. 23, pp. 13437-13442.
Essner et al, "Conserved function for embryonic nodal cilia", Nature, 2002, vol. 418, pp. 37-38.
Etemad-Moghadam et al., "Asymmetrically distributed PAR-3 protein contributes to cell polarity and spindle alignment in early *C. elegans* embryos", Cell, Dec. 1, 1995, vol. 83, No. 5, pp. 743-752.
European Patent Application No. 126325.0, filed Dec. 1, 2000.
European Search Report issued Jul. 22, 2011 in EP 10184660.8.
Case 1:09-cv-11116-PBS Document 500-20. Exhibit 20 Filed Oct. 18, 2010, 5 pages.
Extended European Search Report dated May 26, 2011 for Application No. 10179947.6.
Extended European Search Report dated May 27, 2011 for Application No. 10179952.6.
Extended European Search Report dated May 27, 2011 for Application No. 10180025.8.
Feix et al., "Replication of viral RNA, XIII. The early product of phage RNA synthesis in vitro", Proc. Natl. Acad. Sci. USA, May 1967, vol. 57, No. 5, pp. 1401-1408.
Filipowicz et al., "Biogenesis of small nucleolar ribonucleoproteins", Current Opinion in Cell Biology, 2002, vol. 14, pp. 319-327.
Filipowicz et al., "Post-transcriptional gene silencing by siRNAs and miRNAs", Current Opinion in Structrural Biology, 2005, vol. 15, pp. 331-334.

(56) References Cited

OTHER PUBLICATIONS

Filipowicz et al., "RNAi: the nuts and bolts of the RISC machine", Cell, Jul. 15, 2005, vol. 122, No. 1, pp. 17-20.
Filipowicz, "Imprinted expression of small nucleolar RNAs in brain: Time for Rnomics", PNAS, Dec. 19, 2000, vol. 97, No. 26, pp. 14035-14037.
Filippov et al., "A novel type of RNase III family proteins in eukaryotes", Gene, 2000, vol. 245, pp. 213-221.
Finnegan et al., "Gene silencing: fleshing out the bones", Current Biol., 2001, vol. 11, No. 3, pp. R99-R102.
Fire et al., "Potent and specific genetic interference by double-stranded RNA in *Caenorhabditis elegans*", Nature, Feb. 16, 1998, vol. 391, pp. 806-811.
Fire, "Gene Silencing by Double Stranded RNA," Nobel Lecture, Dec. 8, 2006.
Fire, "RNA-triggered gene silencing", Trends in Genetics, 1999, vol. 15, pp. 358-363.
Flintoft et al., "Virus alert", Nature Reviews Drug Discovery, 2003, vol. 2, pp. 512.
Fraser et al., "Functional genomic analysis of *C. elegans* chromosome I by systematic RNA interference", Nature, 2000, vol. 408, pp. 325-330.
Freitag et al., "Controlling DNA methylation: many roads to one modification", Curr. Opin. Genet. Dev., Apr. 2005, vol. 15, No. 2, pp. 191-199.
Further arguments submitted by BASF SE (Opponent 4) in opposition to EP1407044, dated Sep. 10, 2009.
Further arguments submitted by BASF SE (Opponent 4) in Opposition to EP1407044, dated Sep. 30, 2010.
Further arguments submitted by patentee in EP1407044, dated Oct. 1, 2010.
Further arguments submitted by Sarah E. Rogues (Opponent 3) in opposition to EP1407044, dated Oct. 1, 2010.
Further arguments submitted by Silence Therapeutics (Opponent 5) in opposition to EP1407044, dated Oct. 1, 2010.
Further arguments submitted by Sirna Therapeutics (Opponent 1) in opposition to EP1407044, dated Sep. 29, 2010.
Further submission by patentee in EP1407044, dated Nov. 12, 2010.
Further submission by Sirna Therapeutics (Opponent 1) in opposition to EP1407044, dated Nov. 10, 2010.
Further submission by Sirna Therapeutics (Opponent 1) in opposition to EP1407044, dated Nov. 3, 2010.
Garber, "Prescription RNA," Technology Review, retrieved online at:http://www.technologyreview.com/BioTech/wtr_13020,259,pl. html (2002).
Gebauer et al. "Translation control of dosage compensation in *Drosophila* by sex-lethal: cooperative silencing via the 5' and 3' UTRs of msl-2 mRNA is endependent of the Poly(A) tail", The EMBO Journal, 1999, vol. 18, No. 21, pp. 6146-6154.
Gewirtz et al., "Nucleic acid therapeutics: state of the art and future prospects", Blood, Aug. 1, 1998, vol. 92, No. 3, pp. 712-736.
Gitlin et al., "Nucleic acid-based immune system: the antiviral potential of mammalian RNA silencing", J. Virol., Jul. 2003, vol. 77, No. 13, pp. 7159-7165.
Gitlin et al., "Short interfering RNA confers intracellular antiviral immunity in human cells", Nature, 2002, vol. 418, pp. 430-434.
Gokhale et al., "Antisense raf oligodeoxyribonucleotide is protected by liposomal encapsulation and inhibits Raf-1 protein expression in vitro and in vivo: implication for gene therapy of radioresistant cancer", Gene Ther., Dec. 1997, vol. 4, No. 12, pp. 1289-1299.
Gonczy et al., "Functional genomic analysis of cell division in *C. elegans* using RNAi of genes on chromosome III", Nature, Nov. 16, 2000, vol. 408, pp. 331-336.
Grant et al., "Dissecting the mechanisms of posttranscriptional gene silencing: divide and conquer", Cell, Feb. 5, 1999, vol. 96, pp. 303-306.
Grasby, J. A. et al.: "Purine Functional Groups in Essential Residues of the Hairpin Ribozyme Required for Catalytic Cleavage of RNA", Biochemistry, Mar. 28, 1995, vol. 34, No. 12, pp. 4068-4076.
Greenwood et al., "Ever-decreasing effects", Nature Reviews Cancer, 2003,vol. 3, pp. 236.
Griffey, R. H. et al.: 2'-O-Aminopropyl Ribonucleotides: A Zwitterionic Modification That Enhances the Exonuclease Resistance and Biological Activity of Antisense Oligonucleotides, J Med Chem, Dec. 20, 1996, vol. 39, No. 26, pp. 5100-5109.
Grishok et al., "Genes and mechanisms related to RNA interference regulate expression of the small temporal RNAs that control elegans development timing", Cell, Jul. 13, 2001, vol. 106, pp. 23-34.
Grishok et al., "Genetic requirements for inheritance of RNAi in *C. elegans*", Science, Mar. 2000, vol. 287, pp. 2494-2497.
Grishok et al., "RNAi (Nematodes:*Caenorhabditis elegans*) advances in genetics", 2002, vol. 46, pp. 339-360.
Grishok et al., "Target dependent accumulation of small RNAs during RNAi in *C. Elegans*", International *C. Elegans* Meeting, 2001, pp. 307.
Grishok et al., "Target dependent accumulation of small RNAs during RNAi in *C. elegans*," retrieved online a http://www.wormbase.org/db/misc/paper?name=°/05Bwm2001p307%5D;class=Paper, (2001).
Case 1:09-cv-11116-PBS. Document 131. Plaintiffs' Rule 26(a)(3) Disclosures. Filed Jan. 8, 2010.
Case 1:09-cv-11116-PBS. Document 132. Defendants' Joint Preliminary Witness List. Filed Jan. 8, 2010.
Case 1:09-cv-11116-PBS. Document 133. Plaintiffs' Motion to Seal Document. Filed Jan. 12, 2010.
Case 1:09-cv-11116-PBS. Document 29. Opposition of Defendant Board of Trustees of the University of Massachesetts to Plaintiffs' Motion for Preliminary Judgment. Filed Jul. 14, 2009.
Case 1:09-cv-11116-PBS. Document 30. Defendant Whitehead Institute for Biomedical Research's Opposition to Max Planck's and Alnylam's Motion for Temporary Restraining Order and Preliminary Injunction. Filed Jul. 14, 2009.
Case 1:09-cv-11116-PBS. Document 33. Massachusetts Institute of Technology's Opposition to Plaintiffs' Motion for Preliminary Injunction. Filed Jul. 14, 2009.
Case 1:09-cv-11116-PBS. Document 46. Memorandum in Support of Plaintiffs' Motion to Strike Portions of the Affidavit of Kenneth J. Burchfiel. Filed Jul. 21, 2009.
Case 1:09-cv-11116-PBS. Document 47. Reply Memorandum of Plaintiffs in Support of Motion for Preliminary Injunction. Filed Jul. 21, 2009.
Case 1:09-cv-11116-PBS. Document 48. Supplemental Declaration of Wolfgang Weiss, Ph.D. Filed Jul. 21, 2009.
Case 1:09-cv-11116-PBS. Document 49. Supplemental Declaration of Nancy J. Linck. Filed Jul. 21, 2009.
Case 1:09-cv-11116-PBS. Document 50. Supplemental Declaration of Sandra L. Haberny and Exhibits. Filed Jul. 21, 2009.
Case 1:09-cv-11116-PBS. Document 51. Declaration of Thomas Tuschl and Exhibits. Filed Jul. 21, 2009.
Case 1:09-cv-11116-PBS. Document 80. Defendant Whitehead Answer and Counterclaims to the Complaint. Filed Aug. 25, 2009.
Case 1:09-cv-11116-PBS. Document 81. Defendant Massachusetts Institute of Technology's Answer to the Complaint. Filed Aug. 25, 2009, 17 pages.
Case 1:09-cv-11116-PBS. Document 82. Answer to Complaint and Counterclaim of the University of Massachusetts. Filed Aug. 25, 2009 (21 pages).
Case 1:09-cv-11116-PBS. Document 83. Memorandum and Order by Judge Saris. Dated Sep. 1, 2009 (22 pages).
Case 1:09-cv-11116-PBS. Document 84. Joint Motion for Extension of Time. Filed Sep. 2, 2009.
Case 1:09-cv-11116-PBS. Document 85. Letter/request (non-motion) filed by David Gindler. Filed Sep. 9, 2009.
Case 1:09-cv-11116-PBS. Document 86. Plaintiffs' Reply to Whitehead's Counterclaims. Filed Sep. 17, 2009.
Case 1:09-cv-11116-PBS. Document 87. Plaintiffs' Reply to University of Massachusetts' Counterclaims. Filed Sep. 17, 2009.
Case 1:09-cv-11116-PBS. Document 88. Plaintiffs' Reply to Massachusetts Institute of Technology's Counterclaims. Filed Sep. 17, 2009.
Case 1:09-cv-11116-PBS. Document 89. Joint Motion for Entry of Stipulated Protective Order. Filed Sep. 21, 2009.

(56) References Cited

OTHER PUBLICATIONS

Case 1:09-cv-11116-PBS. Document 90. Stipulated Protective Order. Filed Sep. 24, 2009.
Case 1:09-cv-11116-PBS. Document 91. Motion for Leave to Appear Pro Hac Vice (Michael J. Shuster, Ph.D.). Filed Oct. 12, 2009.
Case 1:09-cv-11116-PBS. Document 92. Motion for Leave to Appear Pro Hac Vice (James L. Tuxbury). Filed Oct. 13, 2009.
Case 1:09-cv-11116-PBS. Document 93. Motion for Leave to Appear Pro Hac Vice (Brett R. Tobin). Filed Oct. 13, 2009.
Case 1:09-cv-11116-PBS. Document 94. Motion for Leave to Appear Pro Hac Vice (Marco J. Quina). Filed Oct. 16, 2009.
Case 1:09-cv-11116-PBS. Document 95. Motion for Leave to Appear Pro Hac Vice (Jeremiah S. Helm). Filed Nov. 3, 2009.
Case 1:09-cv-11116-PBS. Document 96. Motion for Leave to Appear Pro Hac Vice (Alan J. Heinrich). Filed Nov. 3, 2009.
Case 1-09-cv-11116-PBS. Document 97. Non-Party Unopposed Motion for Extension of Time to Complete Fact—Discovery. Filed Nov. 5, 2009.
Case 1:09-cv-11116-PBS. Document 98. Stipulation re: Expert Discovery. Filed Nov. 9, 2009.
Case 1:09-cv-11116-PBS. Document 99. Certificate of Service. Filed Nov. 10, 2009.
Case 1:09-cv-11116-PBS. Document 79. Fourth Supplemental Declaration of Sandra L. Haberny and Exhibits. Filed Aug. 10, 2009 (20 pages).
Case 1:09-cv-11116-PBS. Document 78. Letter to Judge Saris signed by David Gindler. Mailed Aug. 10, 2009 (4 pages).
Case 1:09-cv-11116-PBS. Document 66. Plaintiffs' letter to Judge Saris signed by Morgan Chu. Mailed Aug. 3, 2009 (5 pages).
Case 1:09-cv-11116-PBS. Document 63. Replacement Exhibit 10 to Declaration of Martin Mullins. Filed Jul. 28, 2009.
Case 1:09-cv-11116-PBS. Document 54. Second Supplemental Declaration of Sandra L. Haberny and Exhibits. Filed Jul. 24, 2009.
Case 1:09-cv-11116-PBS. Document 61. Supplemental Declaration of Kenneth J. Burchfiel. Dated Jul. 27, 2009. Filed Jul. 28, 2009.
Case 1:09-cv-11116-PBS. Document 60. Supplemental Declaration of Patricia Granahan and Exhibits. Filed Jul. 28, 2009.
Case 1:09-cv-11116-PBS. Document 67. Third Supplementary Declaration of Sandra L. Haberny and Exhibits. Filed Aug. 3, 2009 (36 pages).
Case 1:09-cv-11116-PBS. Document 56. Whitehead's Opposition to Plaintiffs' Motion to Strike Portions of the Affidavit of Kenneth J. Burchfiel. Filed Jul. 28, 2009.
Case 1:09-cv-11116-PBS. Document 80. Defendant Whitehead Institute for Biomedical Research's Answer and Counterclaims to the Complaint. Filed [RD] Aug. 25, 2009. (24 pages).
Case 1:09-cv-11116-PBS. Document 58. Defendant Whitehead Institute for Biomedical Research's Sur-Reply to the Reply Memorandum of Plaintiffs in Support of Motion for Preliminary Injunction. Filed Jul. 28, 2009.
Case 1:09-cv-11168-PBS. Affidavit of Helen C. Lockhart, Esq. and Exhibits. Filed Jul. 13, 2009.
Case 1:09-cv-11168-PBS. Document 3. Plaintiffs' Motion for Remand and Request for Immediate Hearing. Filed Jul. 10, 2009.
Case 1:09-cv-11168-PBS. Document 9. Plaintiffs' Reply in Support of Motion to Remand. Filed Jul. 22, 2009.
Case 1:09-cv-11168-PBS. Opposition to Plaintiffs' Motion for Remand and Request for Immediate Hearing. Filed Jul. 13, 2009.
Case 1:09-cv-11168-PBS. Transcript of Jul. 30, 2009 motion hearing (30 pages).
Case 1:09-cv-11168-PBS. Wolf Greenfield & Sacks PC's Amended Answer to Plaintiffs' First Amended Complaint. Filed Aug. 11, 2009 (8 pages).
Case 1:09-cv-11168-PBS. Wolf Greenfield & Sacks PC's Sur-Reply in Support of its Opposition to Plaintiffs' Motion for Remand. Filed Jul. 27, 2009.
Jeffrey et al., "Nuclear localization of the interferon-inducible protein kinase PKR in human cells and transfected mouse cells", Experimental Cell Research, 1995, vol. 218, pp. 17-27.
Jen et al., "Suppression of gene expression by targeted disruption of messenger RNA: available options and current strategies", Stem Cells, 2000, vol. 18, pp. 307-319.
Jensen et al., "Taming of transposable elements by homology-dependent gene silencing", Nat. Genet., 1999, vol. 21, pp. 209-212.
Ji, "The mechanism of RNase III action: how dicer dices", Current Topics in Microbiology and Immunology, 2008, vol. 320, pp. 99-116.
Judge, A. D. et al.: "Sequence-dependent stimulation of the mammalian innate immune response by synthetic siRNA", Nature Biotechnology, vol. 23, No. 4, pp. 457-462, Apr. 2005.
Kabanov et al., "DNA complexes with polycations for the delivery of genetic material into cells", Bioconjugate Chem., 1995, vol. 6, pp. 7-20.
Kass et al., "How does RNA methylation repress transcription?", TIG, Nov. 1997, vol. 13, No. 11, pp. 444-449.
Kaufman, R. J., PNAS, Oct. 12, 1999, vol. 96, No. 21, pp. 11693-11695.
Kawasaki et al., "VI. Manipulation of gene manifestation, in vitro dicing and optimized express vectors for siRNA in mammalian cells", Proteins, Nucleic Acids and Enzymes, 2003, vol. 48, No. 11, pp. 1638-1645.
Kehlenbach et al., "Nucleocytoplasmic shuttling factors including Ran and CRM1 mediate nuclear export of NFAT in vitro", J. Cell Biol., May 18, 1998, vol. 141, No. 4, pp. 863-874.
Kennerdell et al., "Hertiable gene silencing in *Drosophilia* using double-stranded RNA", 2000, Nature Biotechnology, vol. 17, pp. 896-898.
Kennerdell et al., "Use of dsRNA-mediated genetic interference to demonstrate that frizzled and frizzled 2 act in the wingless pathway", Cell, Dec. 23, 1998, vol. 95, pp. 1017-1026.
Ketting et al., "A genetic link between co-suppression and RNA interference in *C. elegans*", Nature, Mar. 16, 2000, vol. 404, pp. 296-298.
Ketting et al., "Dicer functions in RNA interference and in synthesis of small RNA involved in developmental timing in *C. elegans*", Gene Dev., Oct. 15, 2001, vol. 15, No. 20, pp. 2654-2659.
Ketting et al., "mut-7 of *C. elegans*, required for transposon silencing and RNA interference, is a homolog of Werner syndrome helicase and RNaseD", Cell, Oct. 1999, vol. 99, pp. 133-141.
Khvorova et al., "Functional siRNAs and miRNAs exhibit strand bias", Cell, 2003, vol. 115, pp. 209-216.
Kidner et al., "Macro effects of microRNAs in plants", Trends Genet., Jan. 2003, vol. 19, No. 1, pp. 13-16.
Kim et al., "Conversion of pre-RISC to holo-RISC by Ago2 during assembly of RNAi complexes", RNA, vol. 13, pp. 22-29.
Kitabwalla M., Ruprecht R.: "RNA Interference—A New Weapon Against HIV and Beyond", N. Engl. J. Med., vol. 347, No. 17, pp. 1364-1367.
Klahre et al., "High molecular weight RNAs and small interefering RNAs induce systemic posttranscriptional gene silencing in plants", PNAS, 2002, vol. 99, No. 18, pp. 11981-11986.
Knight et al., "A role for the RNase III enzyme DCR-1 in RNA interference and germ line develpment in *Caenohabditis elegans*", Science, 2001, vol. 293, pp. 2269-2271.
Koshikin et al., "LNA (Locked Nucleic Acid): An RNA mimic forming exceedingly stable LNA:LNA duplexes", J. Am. Chem. Soc., 1998, vol. 120, pp. 13252-13253.
Kostich et al., "Identification and molecular-genetic characterization of a LAMP/CD68-like protein from *Caenorhabditis elegans*", Journal of Cell Science, 2000, vol. 133, pp. 2595-2606.
Krinke and Wulff, "The cleavage specificity of RNase III," Nucleic Acids Research, vol. 18, pp. 4809-4815 (1990).
Kumar et al., "Antisense RNA: function and fate of duplex RNA in cells of higher eukaryotes", Microbiol. and Molec. Biol. Reviews, Dec. 1998, vol. 62, No. 4, pp. 1415-1434.
Kuwabara et al., "RNAi—prospects for a general technique for determining gene function", Parasitology Today, 2000, vol. 16, pp. 347-349.
Lai, "MicroRNAs: runts of the genome assert themselves", Curr. Biol., Dec. 2, 2003, vol. 13, No. 23, pp. R925-R936, Review.
Lam et al., "Inducible expression of double-stranded RNA directs specific genetic interference in *Drosophila*", Curr. Biol., 2000, vol. 10, pp. 957-963.

(56) References Cited

OTHER PUBLICATIONS

Lamontagne et al., "The RNase III family: a conserved structure and expanding functions in eukaryotic dsRNA metabolism", Curr. Issues Mol. Biol., 2001, vol. 3, No. 4, pp. 71.

Lau et al., "An abundant class of tiny RNAs with probable regulator roles in *Caenorhabditis elegans*", Science, Oct. 26, 2001, vol. 294, No. 5543, pp. 858-862.

Lee et al., "An extensive class of small RNAs in Caenorhabditis elegans", Science, 2001, vol. 294, pp. 862-864.

Lee et al., "Distinct roles for *Drosophila* dicer-1 and dicer-2 in the siRNA/miRNA silencing pathways", Cell, 2004, vol. 117, pp. 69-81.

Lee et al., "Expression of small intefering RNAs targeted against HIV-1 rev transcripts in human cells", Nature Biotechnology, May 2002, vol. 19, pp. 500-505.

Lee et al., "The *C. elegans* heterochroic gene lin-4 encodes small RNAs with antisense complementarity to lin-14", Cell, 1993, vol. 75, pp. 843-854.

Lehmann et al., "The Importance of Internal Loops within RNA Substrates of ADAR1," Journal of Molecular Biology, 291: 1-13 (1999).

Letter from Vossius & Partner dated Jun. 25, 2007 (Patentee's response).

Levin et al., "Methods of double-stranded RNA-mediated gene inactivation in Arabidopsis and their use to define an essential gene in methionine biosynthesis", Plant Molecular Biology, 2000, vol. 44, pp. 759-775.

Lewis et al., "Efficient delivery of siRNA for inhibition of gene expression in postnatal mice", Nature Genetics, 2002, vol. 32, pp. 107-108.

Li et al., "Double-stranded RNA injection produces null phenotypes in *zebrafish*", Dev. Biol., 2000, vol. 217, No. 2, pp. 394-405.

Li et al., "Induction and suppression of RNA silencing by an animal virus", Science, May 17, 2002, vol. 296, pp. 1319-1321.

Li et al., "Using siRNA in pophylactic and therapeutic regimens against SARS coronavirus in *Rhesus macaque*", Nature Medicine, 2005, vol. 11, No. 9, pp. 944-951.

Li et al.: "Double-stranded RNA injection produces null phenotypes in *zebrafish*," Dev. Biology Volume, vol. 210, p. 238, Jun. 1, 1999.

Libonati et al., "Revisiting the action of bovine ribonuclease A and pancreatic-type ribonucleases on double-stranded RNA", Mol. Cell. Biochem., 1992, vol. 117, No. 2, pp. 139-151.

Lima et al., "Cleavage of single strand RNA adjacent to RNA-DNA duplex regions by *Escherichia coli* RNase HI", J. Biol. Chem., Oct. 31, 1997, vol. 272, No. 44, pp. 27513-27516.

Lima et al., "Human RNase H1 uses one tryptophan and two lysines to position the enzyme at the 3'-DNA/5' RNA terminus of the heteroduplex substrate", The Journal of Biological Chemistry, vol. 278, No. 50, pp. 49860-49867.

Lima et al., "The influence of antisense oligonucleotide-induced RNA structure on *Escherichia coli* RNase HI activity", J. Biol. Chem., Jul. 18, 1997, vol. 272, No. 29, pp. 18191-18199.

Lin et al., "Policing rogue genes", Nature, Nov. 11, 1999, vol. 402, pp. 128-129.

Lingel et al. "Nucleic acid 3'-end recognition by the Argonaute2 PAZ domain". Nature Structural & Molecular Biology. vol. 11. No. 6. Jun. 2004.

Lingor et al., "Targeting neurological disease with RNAi", Mol. Biosyst., Nov. 2007, vol. 3, No. 11, pp. 773-780, Epub Aug 29, 2007.

Lipardi et al., "RNAi as random degradative PCR: siRNA primers convert mRNA into dsRNAs that are degraded to generate new siRNAs", Cell, Nov. 2, 2001, vol. 107, No. 3, pp. 297-307.

Abu_Shakra et al., "Cancer and autoimmunity: autoimmune and rheumatic features in patients with malignancies", Annals of the Rheumatic Diseases, 2001, vol. 60, pp. 433-440.

Affidavit of David I. Gindler. Civil Action No. 09-2674-BLS. *Max-Planck-Gesellschaft zur Forderung der Wissenschaften e.V.* v. *Whitehead Institute for Biomedical Research, et al.* Dated Jun. 29, 2009.

Affidavit of Joern Erselius. Civil Action No. 09-2674-BLS. *Max-Planck-Gesellschaft zur Forderung der Wissenschaften e.V.* v. *Whitehead Institute for Biomedical Research, et al.* Dated Jun. 30, 2009.

Affidavit of Nancy J. Linck, Ph.D. Civil Action No. 09-2674-BLS. *Max-Planck-Gesellschaft zur Forderung der Wissenschaften e.V.* v. *Whitehead Institute for Biomedical Research, et al.* Dated Jun. 30, 2009.

Affidavit of Sandra L. Haberny. Civil Action No. 09-2674-BLS. *Max-Planck-Gesellschaft zur Forderung der Wissenschaften e.V.* v. *Whitehead Institute for Biomedical Research, et al.* Dated Jun. 30, 2009.

Affidavit of Wolfgang Weiss. Civil Action No. Sep. 2674-BLS. *Max-Planck-Gesellschaft zur Forderung der Wissenschaften e.V.* v. *Whitehead Institute for Biomedical Research, et al.* Dated Jun. 30, 2009.

Agrawal et al., "RNA interference: biology, mechanism, and applications", Microbiology and Molecular Biology Reviews, 2003, vol. 67, No. 4, pp. 657-685.

Agrawal, "Antisense oligonucleotides: towards clinical trials", Oct. 1996, vol. 4, pp. 376-387.

Agy Therapeutics announces study demonstrating utility of RNA interference in mammalian cells for CNS drug discovery, Press release, Nov. 2001.

Ahlquist, "RNA-dependent RNA polymerases, viruses, and RNA silencing", Science, May 17, 2002, vol. 296, pp. 1270-1273.

Alexeev et al., "Localized in vivo genotypic and phenotypic correction of the albino mutation in skin by RNA-DNA oligonucleotide", Nat. Biotechnol., Jan. 2000, vol. 18, No. 1, pp. 43-7.

Alfonzo et al., "The mechanism of U insertion/deletion RNA editing in kinetoplastid mitochondria", 1997, Nucleic Acids Research, vol. 25, No. 19, pp. 3751-3759.

Ali et al., "Who discovered (or invented 'The art' of double-stranded) RNA interference?", Letter of Ali., May 6, 2005.

Allerson et al., "Fully 2'-modified oligonucleotide duplexes with improved in vitro potency and stability compared to unmodified small interfering RNA", J. Med. Chem., 2005, vol. 48, pp. 901-904.

Amarzguioui et al., "Tolerance for mutations and chemical modifications in a siRNA", Nucleic Acids Research, 2003, vol. 31, No. 2, pp. 589-595.

Ambros, "microRNAs: Tiny regulators with great potential", Cell, 2001, vol. 107, pp. 823-826.

Ambros, "The evolution of our thinking about microRNAs", Nature Medicine, Oct. 2008, vol. 14, No. 10, pp. 1036-1040.

Anderson, "Human gene therapy", Nature, Apr. 30, 1996, vol. 394, pp. 25-31.

Aoki et al., "Inhibition of the p53 tumor suppressor gene results in growth of human aortic vascular smooth muscle cells", Hypertension, 1999, vol. 34, No. 2, pp. 192-200.

Appeal brief submitted by BASF SE (Opponent 4) in opposition to EP1407044, dated Jun. 15, 2011.

Appeal brief submitted by Pfizer (Opponent 2) in opposition to EP1407044, dated Jun. 24, 2011.

Appeal brief submitted by Sarah E. Rogues (Opponent 3) in opposition to EP1407044, dated Jun. 23, 2011.

Appeal brief submitted by Silence Therapeutics (Opponent 5) in opposition by EP1407044, dated Jun. 27, 2011.

Appeal brief submitted by Sirna Therapeutics (Opponent 1) in opposition to EP1407044, dated Jun. 20, 2011.

Applicant's EPO letter opposition to EP1309726, dated Aug. 24, 2006.

Auxiliary request for dismissal of appeals in the opposition proceeding against European Patent No. 1 407 044 (Application No. 01 985 833.1), submitted by patentee, dated Nov. 10, 2011, 12 pages.

Baev et al., "Stress-induced membrane association of the *Streptococcus mutans* GTP-binding protein, an essential G protein, and investigation of its physiological role by utilizing an antisense RNA strategy", Infection and Immunity, 1999, vol. 67, pp. 4510-4516.

Bahramian et al., "Transcriptional and posttranscriptional silencing of rodent a1 (I) collagen by a homologous transcriptionally self-silenced transgene", Molecular and Cellular Biology, Jan. 1999, vol. 19, No. 1, pp. 274-283.

(56) References Cited

OTHER PUBLICATIONS

Barawkar D. A. and T. C. Bruice: "Synthesis, biophysical properties, and nuclease resistance properties of mixed backbone oligonucleotides containing cationic internucleoside guanidinium linkages: Desoxynucleic guanidine/DNA chimeras", Proc. Natl. Acad. Sci. Chemistry, Biochemistry, USA, Sep. 1998, vol. 95, pp. 11047-11052.
Barber G. N. et al.: "Mutants of the RNA-Dependent Protein Kinase (PKR) Lacking Double-Stranded RNA Binding Domain I Can Act as Transdominant Inhibitors and Induce Malignant Transformation", Mol. and Cell. Biol., vol. 15, No. 6, pp. 3138-3146, Jun. 1995.
Bardwell et al., "Autoregulation of RNase III operon by mRNA processing," The EMBO Journal, vol. 8, pp. 3401-3407 (1989).
Barlow et al., "Interferon synthesis in the early post-implantation mouse embryo," Differentiation, vol. 27, pp. 229-235, 1984.
Bartel et al., "Micromanagers of gene expression: the potentially widespread influence of matazoan microRNAs", Nature Review Genetics, 2004, vol. 5, pp. 369-400.
Bartel et al., "MicroRNAs: genomics, biogenesis, mechanism, and function", Cell, Jan. 23, 2004, vol. 116, No. 2, pp. 281-297.
Basic Local Alignment Search Tool (BLAST) analysis, available through NCBI, of nucleic acid sequence "cccggtacccagcttttgttccc" completed on Jan. 11, 2007.
Bass, "RNA editing and hypermutation by adenosine deamination", TIBS, 1997, vol. 22, pp. 157-162.
Bass, "The short answer", Nature, 2001, vol. 411, pp. 428-429.
Baulcombe et al., "Gene silencing: RNA makes RNA makes no protein", Curr Biol., Aug. 26, 1999, vol. 9, No. 16, pp. R599-R601.
Bellon et al., "4'-Thio-oligo-b-D-ribonucleotides: synthesis of b-4'-thio-oligouridylates, nuclease resistance, base pairing properties, and interaction with HIV-1 reverse transcriptase", Nucleic Acids Res., Apr. 11, 1993, vol. 21, No. 7, pp. 1587-1593.
Bernstein et al., "Role for a bidentate ribonuclease in the initiation step of RNA interference", Nature, Jan. 18, 2001, vol. 409, pp. 363-366.
Bernstein et al., "The rest is silence", RNA, 2001, vol. 7, pp. 1509-1521.
Bevilacqua et al.,"Minor-groove recognition of double-stranded RNA by the double-stranded RNA-binding domain from the RNA-activated protein kinase PKR", Biochemistry, 1996, vol. 35, pp. 9983-9994.
Bhan, P. et al.: "2',5'-linked oligo-3'-desoxyribonucleoside phosphorothioate chimeras: thermal stability and antisense inhibition of gene expression", Nucleic Acid Research, vol. 25, 1997, pp. 3310-3317.
Billy et al., "Specific interference with gene expression induced by long, double-stranded RNA in mouse embryonal teratocarcinoma cell lines", PNAS, Dec. 4, 2001, vol. 98, No. 5, pp. 14428-14433.
Borst et al., "Replication of viral RNA, VIII. Studies on the enzymatic mechanism of replication of MS2 RNA", Proc. Natl. Acad. Sci. USA, Sep. 1965, vol. 54, No. 3, pp. 982-987.
Bosher et al., "RNA interference can target pre-mRNA: consequences for gene expression in a Caenorhabditis elegans operon", Genetics, Nov. 1999, vol. 153, No. 3, pp. 1245-1256.
Bosher et al., "RNA interference: genetic wand and genetic watchdog", Nature Cell Biology, Feb. 2000, vol. 2, pp. E31-E36.
Boutla et al., "Developmental defects by antisense-mediated inactivation of micro-RNAs 2 and 13 in Drosophila and the identification of putative target genes", Nucleic Mils Research, 2003, vol. 31, No. 17, pp. 4973-4980.
Boutla et al., "Short 5'-phosphorylated double-stranded RNAs induce RNA interference in Drosophila", Current Biology, 2001, vol. 11, pp. 1776-1780.
Braasch et al., "RNA interference in mammalian cells by chemically-modified RNA", Biochemistry, 2003, vol. 42, pp. 7967-7975.
Tahbaz et al., "Characterization of the interactions between mammalian PAZ PIWI domain proteins and dicer", Embo Reports, 2004, vol. 5, No. 2, pp. 189-194.
Takeshita et al., "Homodimeric structure and double-stranded RNA cleavage activity of the C-terminal RNase III domain of human dicer", J. Mol. Biol., 2007, vol. 374, pp. 106-120.
Takeshita et al., "Increased gene expression after liposome-mediated arterial gene transfer associated with intimal smooth muscle cell proliferation. In vitro and in vivo findings in a rabbit model of vascular injury", J. Clin. Invest., Feb. 1994, vol. 93, No. 2, pp. 652-661.
Tan et al., "Gene knockdown with intrathecal siRNA of NMDA receptor NR2B subunit reduces formalin-induced nociception in the aat", Gene Therapy, 2005, vol. 12, pp. 59-66.
Tang et al., "A biochemical framework for RNA silencing in plants", Genes & Development, 2003, vol. 17, pp. 49-63.
Tao et al., "Drug target validation: Lethal infection blocked by inducible peptide", PNAS, 2000, vol. 97, No. 2, pp. 783-786.
Tenllado et al., "Double-stranded RNA-mediated interference with plant virus infection", Journal of Virology, Dec. 2001, vol. 75, No. 24, pp. 12288-12297.
Thakker et al., "Neurochemical and behavioral consequences of widespred gene knockdown in the adult mouse brain by using nonviral interference", PNAS, 2004, vol. 101, No. 49, pp. 17270-17275.
The Nobel Prize in Physiology or Medicine, 2006, pp. 1-3.
Tijsterman et al, "RNA helicase MUT-14-dependent gene silencing triggered in C. elegans by short antisense RNAs", Science, 2002, vol. 295, pp. 694-697.
Tijsterman et al., "PPW-1, a PAZ/PIWI protein required for difficient germline RNAi, is defective in a natural isolate of C. elegans", Current Biology, 2002, vol. 12, pp. 1535-1540.
Tijsterman et al., "The genetics of RNA silencing", Annu. Rev. Genet., 2002, vol. 36, pp. 489-519.
Timmons et al., "Ingestion of bacterially expressed dsRNAs can produce specific and potent genetic interference in Caenorhabditis elegans", Genem, 2001, vol. 263, pp. 103-112.
Timmons et al., "Specific interference by ingested dsRNA", Nature, Oct. 29, 1998, vol. 395, pp. 854.
Tracewell et al., "In vivo modulation of the rat cytochrome P450 1A1 by double-stranded phosphorothioate oligodeoxynucleotides", Toxicology and Applied Pharmacology, 1995, vol. 135, pp. 179-184.
TranSilent siRNA Vector Mix, Product User Manual, release Sep. 24, 2003.
Tuschl et al., "Functional genomics: RNA sets the standard", Nature, Jan. 16, 2003, vol. 421, No. 6920, pp. 220-221.
Tuschl et al., "Importance of exocyclic base functional groups of central core guanosines for hammerhead ribozyme activity", Biochemistry, 1993, vol. 32, pp. 11658-11668.
Tuschl et al., "Selection in vitro of novel ribozymes from a partially randomized U2 and U6 snRNA library", Embo. J., 1998, vol. 17, pp. 2637-2650.
Tuschl et al., "Targeted mRNA degradation by double-stranded RNA in vitro", Genes & Development, 1999, vol. 13, pp. 3191-3197.
Tuschl, "Expanding small RNA interference", Nature Biotechnology, 2002, vol. 20, pp. 446-448.
Tuschl, "Mammalian RNA interference", RNAi: A Guide to Gene Silencing, 2003, Chapt. 13, pp. 265-295.
Tuschl, "RNA interference and small interfering RNAs", Chem Biochem, 2001, vol. 2, pp. 239-245.
Tuschl, "Small interfering RNAs: a revolutionary tool for the analysis of gene function and gene therapy", Molecular Interventions, 2002, vol. 2, No. 3, pp. 158-167.
U.S. Appl. No. 60/193,594, filed Mar. 30, 2000.
U.S. Appl. No. 60/265,232, filed Jan. 31, 2001.
U.S. Appl. No. 60/189,739, filed Mar. 16, 2000.
U.S. Appl. No. 60/243,097, filed Oct. 24, 2000.
Ueda et al., "Phosphorothioate-containing RNAs show mRNA activity in the prokaryotic translation systems in vitro", Nucleic Acids Research, 1991, vol. 19, No. 3, pp. 547-552.
Uhlmann, E. et al.: "Antisense Oligonucleotides: A new therapeutic principle", Chemical Reviews, US, American Chemical Society, Easton, vol. 90, No. 4, Jun. 1, 1990, pp. 543-584, XP000141412, ISSN: 0009-2665.

(56) References Cited

OTHER PUBLICATIONS

Ui-Tei et al., "Sensitive assay of RNA interference in *Drosophila* and Chinese hamster cultured cells using firefly luciferase gene as target", FEBS Letters, 2000, vol. 479, pp. 79-82.
Vaucheret et al., "Transgene-induced gene silencing in plants", Plant J., Dec. 1998, vol. 16, No. 6, pp. 651-659.
Verma et al., "Gene therapy promises, problems and prospects", Nature, Sep. 18, 1997, vol. 389, pp. 239-242.
Verma et al., "Modified oligonucleotides: synthesis and strategy for users", Annu. Rev. Biochem., 1998, vol. 67, pp. 99-134.
Vickers et al., "Efficient reduction of target RNAs by small interfering RNA and RNase H-dependent antisense agents", The Journal of Biological Chemistry, 2003, vol. 278, No. 9, pp. 7108-7118.
Vinayak et al., "Chemical synthesis of RNA using fast oligonucleotide deprotection chemistry", Nucleic Acids Research, 1992, vol. 20, No. 6, pp. 1265-1269.
Voinnet et al., "A viral movement protein prevents spread of the gene silencing signal in *Nicotiana benthamiana*", Cell, 2000, vol. 103, pp. 157-167.
Voinnet, O. and D. C. Baulcombe: "Systemic signalling in gene silencing", Nature, vol. 389, p. 553, Oct. 9, 1997.
Wagner et al., "Functional genomics double-stranded RNA poses puzzle", Nature, Feb. 1998, vol. 391, pp. 744-745.
Wahls, "RNA associated with a heterodimeric protein that activates a meiotic homologous recombination hot spot: RL/RT/PCR strategy for cloning any unknown RNA or DNA", PCR Methods and Applications, 1994, vol. 3, pp. 272-277.
Wall et al., "Small RNA: can RNA interference be exploited for therapy?", The Lancet, 2003, vol. 362, pp. 1401-1403.
Wang et al., "Delivery of antisense oligodeoxyribonucleotides against the human epidermal growth factor receptor into cultured KB cells with liposomes conjugated to folate via polyethylene glycol", Proc. Natl. Acad. Sci., Apr. 1995, vol. 92, pp. 3318-3322.
Wang et al., "Inhibition of *Trypanosoma brucei* gene expression by RNA interference using an integratable vector with opposing T7 promoters", The Journal of Biological Chemistry, Dec. 22, 2000, vol. 275, No. 51, pp. 40174-40179.
Wang et al., "Relative stabilities of triple helices composed of combinations of DNA, RNA and 2'-O-methyl-RNA backbones: chimeric circular oligonucleotides as probes", Nuc. Acids Res., 1995, vol. 23, No. 7, pp. 1157-1164.
Wang et al., "Replicating satellite RNA induces sequence-specific DNA methylation and truncated transcripts in plants", RNA, Jan. 2001, vol. 7, No. 1, pp. 16-28.
Wargelius et al., "Double-stranded RNA induces specific developmental defects in *Zebrafish embryos*", Biochem. Biophys. Res. Commun., Sep. 16, 1999, vol. 263, No. 1, pp. 156-161.
Wassenbegger, "RNA—directed DNA methylation", Plant Molec. Biol., 2000, vol. 43, pp. 203-220.
Waterhouse et al., "Exploring plant genomes by RNA-induced gene silencing", Nature Reviews Genetics, 2002, vol. 4, pp. 29-38.
Waterhouse et al., "Virus resistance and gene silencing in plants can be induced by simultaneous expression of sense and antisense RNA", Proc. Nat'l. Acad. Sci., Nov. 1998, vol. 95, pp. 13959-13964.
Grishok et al., VI. RNAi and Development References, Abstract, pp. 340-360.
Gryaznov S. M. and R. L. Letsinger: "Template controlled coupling and recombination ofoligonucleotide blocks containing thiophosphoryl groups", Nucleic Acids Res, Mar. 25, 1993, vol. 21, No. 6, pp. 1403-1408.
Grzelinski et al., "RNA interference-mediated gene silencing of pleiotrophin through polyethylenimine complexed small interfering RNAs in vivo exerts antitumoral effects in glioblastoma xenografts", Human Gene Therapy, 2006, vol. 17, pp. 751-766.
Guo et al., "par-1, a gene required for establishing polarity in *C. elegans* embryos, encodes a putative Ser/Thr kinase that is asymmetrically distributed", Cell, 1995, vol. 81, pp. 611-620.
Ha, I. et al.: "A bulged lin-4/lin-14 RNA duplex is sufficient for *Caenorhabditis elegans* lin-14 temporal gradient formation", Genes Development, Dec. 1, 1996; vol. 10, No. 23, pp. 3041-3050.

Haase et al., "TRBP, a regulator of cellular PKR and HIV-1 virus expression, interacts with Dicer and functions in RNA silencing", EMBO Reports, 2005, vol. 6, No. 10, pp. 961-967.
Haley et al., "In vitro analysis of RNA interference in *Drosophila melanogaster*", Methods, 2003, vol. 30, pp. 330-336.
Hamada et al., "Effects of RNA interference in gene expression (RNAi) in cultured mammalian cells of mismatches and the introduction of chemical modifications at the 3'-ends of siRNAs", Antisense and Nucleic Acid and Drug Development, 2002, vol. 12, pp. 301-309.
Hamilton et al., "A novel humanised antibody against Prostate Specific Membrane Antigen (PSMA) for in vivo targeting and therapy", Proceedings of the American Association for Cancer Research, 1998, Poster Presentation No. 2997.
Hamilton et al., "A species of small antisense RNA in post-transcriptional gene silencing in plants", Science, Oct. 1999, vol. 286, pp. 950-952.
Hamilton et al., "Two classes of short interfering RNA in RNA silencing", The EMBO Journal, 2002, vol. 21, No. 17, pp. 4671-4679.
Hammond et al., "An RNA-directed nuclease mediates post-transcriptional gene silencing in *Drosophila* cells", Nature, Mar. 16, 2000, vol. 404, pp. 293-296.
Hammond et al., "Argonaute2, a link between genetic and biochemical analyses of RNAi", Science, Aug. 10, 2001, vol. 293, pp. 1146-1150.
Hammond et al., "Post-transcriptional gene silencing by double-stranded RNA", Nature, Feb. 2001, vol. 2, pp. 110-119, Reviews/Genetics.
Hannon, "RNA interference", Nature, 2002, vol. 418, pp. 244-251.
Harada et al., "Absence of the Type I IFN System in EC Cells: Transcriptional Activator (IRF-1) and Repressor (IRF-2) Genes are Developmentally Regulated," Cell, vol. 83, pp. 303-312, 1990.
Harborth et al., J. Cell Science 114: 4457-4565.
Hedges S. B., "The Origin and Evolution of Model Organisms", Nature, vol. 3; Nov. 2002.
Heinrichs et al., "Chop, chop", Nature Reviews Molecular Cell Biology, 2003, vol. 4, pp. 829.
Heinrichs et al., "Down a hairpin", Nature Reviews Molecular Cell Biology, 2003, vol. 4, pp. 173.
Heinrichs et al., "Spreading silence", Nature Reviews Molecular Cell Biology, 2003, vol. 4, pp. 823.
Ho et al., "Potent antisense oligonucleotides to the human multidrug resistance-1 mRNA are rationally selected by mapping RNA-accessible sites with oligonucleotide libraries", Nucleic Acids Research, 1996, vol. 24, No. 10, pp. 1901-1907.
Hohjoh, "RNA interference (RNAi) induction with various types of synthetic oligorucleotide duplexes in cultured human cells", FEBS Letters, 2002, vol. 521, pp. 195-199.
Hoke, G. D. et al.: Effects ofphosphorothioate capping on antisense oligonucleotide stability, hybridization and antiviral efficacy versus herpes simplex virus infection, Nucleic Acids Res, Oct. 25, 1991, vol. 19, No. 20, pp. 5743-5748.
Holen et al., "Positional effects of short interfering RNAs targeting the human coagulation trigger Tissue Factor", Nucleic Acids Research, 2002, vol. 30, No. 8, pp. 1757-1766.
Holen et al., "Similar behaviour of single-strand and double-strand siRNAs suggests they act through a common RNAi pathway", Nucleic Acids Research, 2003, vol. 31, No. 9, pp. 2401-2407.
Hope, "RNAi surges on: application to cultured mammalian cells", Trends Genet., Aug. 2001, vol. 17, No. 8, pp. 440.
Horn, T. et al.: "Chemical synthesis and characterization of branched oligodesoxyribonucleotides (bDNA) for use as signal amplifiers in nucleic acid quantification assays", Nucleic Acids Research, 1997, vol. 25, No. 23, pp. 4842-4849.
Hornung, V. et al.: "Sequence-specific potent induction of IFN-Alfa by short interfering RNA in plasmacytoid dendritic cells trough TLR7", Nature Medicine, vol. 11, No. 3, pp. 263-270, Mar. 2005.
Hossbach et al., "Gene silencing with siRNA duplexes composed of target-mRNA-complementary and partially palindromic or partially complementary single-stranded siRNAs", RNA Biology, 2006, vol. 3, No. 2, pp. 82-89.
Hough et al., "Why RNAi makes sense", Nature Biotechnology, 2003, vol. 21, No. 7, pp. 731-732.

(56) References Cited

OTHER PUBLICATIONS

Hsieh et al., "Recognition and Silencing of Repeated DNA", Annu. Rev. Genet., 2000, vol. 34, pp. 187-204.
Hsieh et al., "The Ring finger/B-Box factor TAM-1 and a retinoblastoma-like protein Lin-35 modulate context-dependent gene silencing in *Caenorhabditis elegans*", Genes & Development, 1999, vol. 13, pp. 2958-2970.
Hu-Lieskovan et al., "Sequence-specific knockdown of EWS-FLI1 by targeted, nonviral delivery of small interfering RNA inhibits tumor growth in a murine model of metastatic Ewing's sarcoma", Cancer Research, 2005, vol. 65, No. 19, pp. 8984-8992.
Hunter et al., "Missing Links: miRNAs and plant development", Current Opinion in Genetics & Development, 2002, vol. 13, pp. 372-378.
Hunter T. et al.: "The Characteristics of Inhibition of Protein Synthesis by Double-Stranded Ribonucleic Acid in Reticulocyte Lysates", The Journal of Biological Chemistry, vol. 250, No. 2, pp. 409-417, Jan. 25, 1975.
Hunter, "Gene silencing: shrinking the black box of RNAi", Current Biol., 2000, vol. 10, No. 4, pp. R137-R140.
Hunter, "Genetics: a touch of elegance with RNAi", Current Biol., 1999, vol. 9, No. 12, pp. R440-R442.
Hutvagner et al., "A cellular function for the RNA-interference enzyme dicer in the maturation of the let-7 small temporal RNA", Science, Aug. 3, 2001, vol. 293, pp. 834-838.
Hutvagner et al., "Detailed characterization of the posttranscriptional gene-silencing-related small RNA in a GUS gene-silenced tobacco", RNA, 2000, vol. 6, pp. 1445-1454.
Hutvagner et al., "In vitro processing of pre-let-7 RNA", Department of Biochemistry & Molecular Pharmacology.
Hutvagner et al., "Intersection of the RNA interference and small temporal RNA pathways", Eukaryotic mRNA Processing.
Hutvagner et al., "RNAi: nature abhors a double-strand", Curr. Opin. Genet. Dev., Apr. 2002, vol. 12, No. 2, pp. 225-232.
Interlocutory decision issued by Opposition Division in opposition proceedings to EP1407044, dated Feb. 15, 2011.
International Search Report for PCT/DE00/00244 dated Jun. 20, 2000.
International Search Report for PCT/EP01/13968, mailed Jul. 29, 2003.
Jackson et al., "Expression profiling reveals off-target gene regulation by RNAi", Nature Biotechnology, 2003, vol. 21, pp. 635-637.
Jacobs et al., "When two strands are better than one: the mediators and modulators of the cellular responses to double-stranded RNA", Virology, 1996, vol. 219, No. 2, pp. 339-349, Review.
Jacobsen et al., "Disruption of an RNA helicase/RNase III gene in *Arabidopsis* causes unregulated cell division in floral meristems", Development, 1999, vol. 126, pp. 5231-5243.
Jarvis, "Optimize transfection of siRNAs for RNA ", TechNotes, 9:6, 2002.
Braich, R. S. and M. 1. Damha: "Regiospecific Solid-Phase Synthesis of Branched Oligonucleotides. Effect of Vicinal 2',5'-(or 2',3'-) and 3',5'-Phosphodiester Linkages on the Formation of Hairpin DNA", Bioconjugate Chem.; May-Jun. 1997; vol. 8, No. 3, pp. 370-377.
Branch, "A good antisense molecule is hard to find", TIBS, Feb. 1998, vol. 23, pp. 45-50.
Brantl, "Antisense-RNA regulation and RNA interference", Biochimica et Biophysica Acta, 2002, vol. 1575, pp. 15-25.
Braun et al., "Oligonucleotide and plasmid DNA packaging into polyoma VPI virus-like particles expressed in *Escherichia coli*", Biotechnol. App. Biochem., 1999, vol. 29, pp. 31-34.
Brennicke, A. et al.: "RNA editing", FEMS Microbiology Reviews 23, pp. 297-316.
Bridge et al., "Induction of an inteferon response by RNAi vectors in mammalian cells", Nature Genetics, 2003, vol. 34, No. 3, pp. 263-264.
Brummelkamp et al., "A system for stable expression of short interfering RNAs in mammalian cells", Science Express, Mar. 21, 2002, pp. 1-6.
Brummelkamp et al., "New tools for functional mammalian cancer genetics", Nat. Rev. Cancer, Oct. 2003, vol. 3, No. 10, pp. 781-789.
Bumcrot et al., "RNAi therapeutics: a potential new class of pharmaceutical drugs," Nature Chemical Biology, vol. 2, No. 12: 711-719 (2006).
Burke et al., "Appearance of Interferon Inducibility and Sensitivity during Differentiation of Murine Teratocarcinoma Cells in Vitro," Cell, vol. 13, pp. 243-248, 1978.
Byrom et al., "Inducing RNAi with siRNA cocktails generated by RNase III", TechNotes, vol. 10, pp. 1, Ambion (2004).
Cameron et al., "Inhibition of gene expression by a short sense fragment", Nucleic Acids Res., Feb. 11, 1991, vol. 19, No. 3, pp. 469-475.
Caplen et al., "dsRNA-mediated gene silencing in cultured *Drosophila* cells: a tissue culture model for the analysis of RNA interference", Gene, 2000, vol. 252, pp. 95-105.
Caplen et al., "Specific inhibition of gene expression by small double-stranded RNAs in invertebrate and vertebrate systems", PNAS, Aug. 14, 2001, vol. 98, No. 17, pp. 9742-9747.
Caplen, "RNAi as a gene therapy approach", Expert Opin. Biol. Ther., 2003, vol. 3, No. 4, pp. 575-586.
Carmell et al., "The Argonaute family: tentacles that reach into RNAi, developmental control, stem cell maintenance, and tumorigenesis", Genes & Development, vol. 16, pp. 2733-2742.
Carrington et al., "Role of microRNAs in plant and animal development", Science, Jul. 18, 2003, vol. 301, No. 5631, pp. 336-338.
Carthew et al., "Gene silencing by double-stranded RNA", Curr Opin Cell Biol., 2001, vol. 2, pp. 244-248.
Case 1:09-cv-11116-PBS. Document 31. Declaration of Helen Lockhart and Exhibits. Filed Jul. 14, 2009.
Case 1:09-cv-11116-PBS. Document 62. Declaration of Kendra P. Robins. Dated Jul. 27, 2009. Filed Jul. 28, 2009.
Case 1:09-cv-11116-PBS. Document 35. Declaration of Kenneth J. Burchfiel and Exhibits. Filed Jul. 14, 2009.
Case 1:09-cv-11116-PBS. Document 34. Declaration of Martin Mullins and Exhibits. Filed Jul. 14, 2009.
Case 1:09-cv-11116-PBS. Document 36. Declaration of Patricia Granahan and Exhibits. Filed Jul. 14, 2009.
Case 1:09-cv-11116-PBS. Document 59. Declaration of Timothy W. Nilsen and Exhibits. Dated Jul. 24, 2009. Filed Jul. 28, 2009.
Case 1:09-cv-11116-PBS. Document 100. Joint Motion for Amendments to the Stipulated Protective Orders. Filed Nov. 17, 2009.
Case 1:09-cv-11116-PBS. Document 101. Amendments to Stipulated Protective Orders. Filed Nov. 18, 2009.
Case 1:09-cv-11116-PBS. Document 102. Emergency Motion for Relief from Defendants' Misuse of the Protective Order to block Plaintiffs' In-House Counsel from Attending Inventor Depositions. Filed Nov. 23, 2009.
Case 1:09-cv-11116-PBS. Document 103. Memorandum of Law in Support of Plaintiffs' Emergency Motion for Relief from Defendants' Misuse of the Protective Order to block Plaintiffs' In-House Counsel from Attending Inventor Depositions. Filed Nov. 23, 2009.
Case 1:09-cv-11116-PBS. Document 104. Declaration of Michael J. Strub, Jr. Filed Nov. 23, 2009.
Case 1:09-cv-11116-PBS. Document 105. Motion for Protective Order Respecting Documents Produced by Dr. Brenda Bass. Filed Dec. 7, 2009.
Case 1:09-cv-11116-PBS. Document 106. Protective Order. Filed Dec. 8, 2009.
Case 1:09-cv-11116-PBS. Document 107. Motion for Reconsideration of Order that Documents Produced by Dr. Brenda Bass be Governed by an Amended Protective Order that Would Deprive Plaintiffs' Counsel of the Ability to Effectively Analyze the Documents. Filed Dec. 10, 2009.
Case 1:09-cv-11116-PBS. Document 108. Declaration of Michael H. Strub, Jr. Filed Dec. 10, 2009.
Case 1:09-cv-11116-PBS. Document 109. Defendants' Motion to Strike Plaintiffs' Jury Demand. Filed Dec. 14, 2009.
Case 1:09-cv-11116-PBS. Document 110. Defendants' Assented to Motion to Impound. Filed Dec. 14, 2009.
Case 1:09-cv-11116-PBS. Document 111. Opposition to Motion for Reconsideration. Filed Dec. 17, 2009.

(56) References Cited

OTHER PUBLICATIONS

Case 1:09-cv-11116-PBS. Document 112. Reply to Motion for Reconsideration. Filed Dec. 18, 2009.
Case 1:09-cv-11116-PBS. Document 113. Joint Motion to Modify Certain Pretrial Dates in Scheduling Order. Filed Dec. 21, 2009.
Case 1:09-cv-11116-PBS. Document 114. Defendants' Second Assented to Motion to Seal. Filed Dec. 21, 2009.
Case 1:09-cv-11116-PBS. Document 115. Memorandum in Support of Defendants' Motion to Strike Plaintiffs' Jury Demand. Filed Dec. 22, 2009.
Case 1:09-cv-11116-PBS. Document 117. Plaintiffs' Motion to Seal. Filed Dec. 28, 2009.
Case 1:09-cv-11116-PBS. Document 118. Opposition of Plaintiffs to Defendants' Motion to Strike Jury Demand. Filed Dec. 28, 2009.
Case 1:09-cv-11116-PBS. Document 121. Letter/request (non-motion) by Thomas F. Maffei, P.C. Filed Dec. 30, 2009.
Case 1:09-cv-11116-PBS. Document 122. Plaintiffs' Motion for Leave to File First Amended Complaint. Filed Jan. 4, 2010.
Case 1:09-cv-11116-PBS. Document 123. Plaintiffs' Assented to Motion to Seal. Filed Jan. 4, 2010.
Case 1:09-cv-11116-PBS. Document 124. Defendants' Motion for Leave to File Reply Brief in Support of Motion to Strike Jury Demand. Filed Jan. 4, 2010.
Case 1:09-cv-11116-PBS. Document 125. Defendants' Assented to Motion to Seal. Filed Jan. 5, 2010.
Case 1:09-cv-11116-PBS. Document 126. Reply Brief in Support of Defendants' Motion to Strike Plaintiffs' Jury Demand. Filed Jan. 6, 2010.
Case 1:09-cv-11116-PBS. Document 129. Defendants' Joint Preliminary Exhibit List. Filed Jan. 8, 2010.
Case 1:09-cv-11116-PBS. Document 130. Defendants' Joint Preliminary Exhibit List. Filed Jan. 8, 2010.
Cheng et al., "RNA interference and human disease", Mol. Genet. Metab., Sep.-Oct. 2003, vol. 80, No. (1-2), pp. 121-128.
Chi et al., "Genomewide view of gene silencing by small interfering RNAs", PNAS, 2003, vol. 100, No. 11, pp. 6343-6346.
Chien P. Y. et al.: "Novel cationic cardiolipin analogue-based liposome for efficient DNA and small interfering RNA delivery in vitro and in vivo", Cancer Gene Therapy, Nature Publishing Group, 2004, pp. 1-8.
Chiu et al., "RNAi in human cells: basic structural and functional features of small interfering RNA", Molecular Cell, Sep. 2002, vol. 10, pp. 549-561.
Chiu et al., "siRNA function in RNAi: A chemical modification analysis", RNA, 2003, vol. 9, pp. 1034-1048.
Civil Action No. 09-02654-BLS. Affidavit of Joern Erselius and Exhibits. Filed Jul. 9, 2009.
Civil Action No. 09-02654-BLS. Memorandum in Support of Plaintiffs Emergency Motion for a Temporary Restraining Order Against Wolf Greenfield & Sacks, PC. Filed Jul. 10, 2009.
Civil Action No. 09-02654-BLS. Plaintiffs Emergency Motion for a Temporary Restraining Order Against Wolf Greefield & Sacks, PC. Filed Jul. 10, 2009.
Clemens et al., "Inhibition of cell-free protein synthesis by pppA2'p5'A2'p5' A: a novel oligonucleotide synthesized by interferon treated L cell extracts", Cell, Mar. 1978, vol. 13, pp. 565-572.
Clemens et al., "The double-stranded RNA-dependent protein kinase PKR: structure and function", Journal of Inteferon and Cytokine Research, 1997, vol. 17, pp. 503-524.
Clemens et al., "Use of double-stranded RNA interference in *Drosophila* cell lines to dissect signal transduction pathways", PNAS, Jun. 6, 2000, vol. 97, No. 12, pp. 6499-6503.
Clemens, "PKR—a protein kinase regulated by double-stranded RNA", Int. J. Biochem., Cell Biol., 1997, vol. 29, No. 7, pp. 945-949.
Cogoni et al., "Gene silencing in neurospora crassa requires a protein homologous to RNA-dependent RNA polymerase", Nature, May 1999, vol. 399, pp. 166-169.
Cogoni et al., "Homology-dependent gene silencing in plants and fungi: a number of variations on the same theme", Curr. Opin. Microbiol., 1999, vol. 2, pp. 657-662.
Cogoni et al., "Posttranscriptional gene silencing in neurospora by a RecQ DNA helicase", Science, Dec. 17, 1999, vol. 286, pp. 2342-2344.
Complaint. Civil Action No. Sep. 2674. *Max-Planck-Gesellschaft zur Forderung der Wissenschaften e.V.v. Whitehead Institute for Biomedical Research, et al.* Dated Jun. 26, 2009.
Conte et al., "RNA interference in Caenorhabditis elegans", Current Protocols in Molecular Biology, 2003, Unit 26.3, Supplement 62, pp. 26.3.1-26.3.20.
Corsi et al., "*Caenorhabditis elegans* Twist plays an essential role in non-striated muscle development", Development, 2000, vol. 127, pp. 2041-2051.
Couzin et al., "Molecular biology. RNAi shows cracks in its armor", Science, Nov. 12, 2004, vol. 306, No. 5699, pp. 1124-1125.
Couzin, J., "Breakthrough: Small RNAs Make Big Splash", Science, vol. 298, pp. 2296-2297, Dec. 2002.
Crooke et al., "Kinetic characteristics of *Escherichia coli* RNase HI: cleavage of various antisense oligonucleotide-RNA duplexes", Biochem J., Dec. 1, 1995, vol. 312, Pt 2, pp. 599-608.
Cullen, "Derivation and function of small interfering RNAs and microRNAs", Virus Research, 2004, vol. 102, pp. 3-9.
Cullen, "RNA interference: antiviral defense and genetic tool", Nature Immunology, 2002, vol. 3, No. 7, pp. 597-599.
Cullen, "RNAi the natural way", Nature Genetics, 2005, vol. 37, No. 11, pp. 1163-1165.
Cummins et al., "Characterization of fully 2'-modified oligoribonucleotide hetero- and homoduplex hybridization and nuclease sensitivity", Nucleic Acids Res., Jun. 11, 1995, vol. 23, No. 11, pp. 2019-2024.
Czauderna et al., "Structural variations and stabilising modifications of synthetic siRNAs in mammalian cells", Nucleic Acids Research, 2003, vol. 31, No. 11, pp. 2705-2716.
Dalmay et al., "An RNA-dependent RNA polymerase gene in Arabidopsis in required for posttranscriptional gene silencing mediated by a transgene but not by a virus", Cell, 2000, vol. 101, pp. 543-553.
De Fougerolles et al., "siRNA and the lung: research tool or therapeutic drug?", Current Opinion in Pharmacology, 2008, vol. 8, pp. 280-285.
De Mesmaeker et al., "Backbone modifications in oligonucleotides and peptide nucleic acid systems", Curr. Opin. Stud. Biol., Jun. 1995, vol. 5, No. 3, pp. 343-355.
Declaration of Rachel Meyers, Ph.D. Under 35 U.S.C. §1.132, dated Jul. 24, 2009.
Declaration of Thomas Tuschl Under 35 U.S.C. §1.132, dated Jan. 21, 2009.
Declaration of Witold Filipowicz, M.D., Ph.D., Under 35 U.S.C. §1.132, dated Jan. 12, 2009.
Definitions "Compact Oxford English Dictionary" (printed Jan. 28, 2008).
Depalma et al., "Making Sense of RNA Interference Methods", retrieved online http://www.adepalmacom/genomics/0303/Genomics%20and%20Proteomics%20-%20Making%20Sense%20ofY02ORNA%20Interference%20Methods.htm (2003).
Dernburg et al., "Transgene-mediated cosuppression in the *C. elegans* germ line", Genes & Dev., 2000, vol. 14, pp. 1578-1583.
Devroe et al., "Retrovirus-delivered siRNA", BMC Biotechnology, 2002, vol. 2, pp. 1-5.
Devroe et al., "Therapeutic potential of retroviral RNAi vectors", Expert Opin. Biol. Ther., Mar. 2004, vol. 4, No. 3, pp. 319-327.
Diagram indicating the melting curve of a 19 base pair double stranded molecule submitted by Appellant II in the appeal proceedings against EP 1 144 623 on Feb. 5, 2007.
Diagram indicating the melting curve of two 23 base pair double stranded molecules submitted by Appellant II in the appeal proceedings against EP 1 144 623 on Feb. 5, 2007 (2 sheets).
Dichoso et al., "The MADS-box factor CeMEF2 is not essential for caenorhabditis elegans myogenesis and development", Developmental Biology, 2000, vol. 223, pp. 431-440.
Doench et al, "siRNAs can function as miRNAs", Genes & Development, 2003, vol. 17, pp. 438-442.

(56) References Cited

OTHER PUBLICATIONS

Doi et al- "Short-Interfering-RNA-mediated gene silencing in mammalian cells requires dicer and d1F2C translation initiation nitiation factors", Current Biology, 2003, vol. 13, pp. 41-46.
Donze et al, "RNA interference in mammalian cells using siRNAs synthesized with T7 RNA polymerase", Nucleic Acids Research, 2002, vol. 30, No. 10, pp. 1-4.
Dostie, J. et al, "Numerous microRNPs in neuronal cells containing novel microRNAs," RNA, 2003, vol. 9, pp. 180-186.
Dunn, "Ribonuclease III", The Enzymes, 1982, Chapt. 15, vol. 15, pp. 485-499.
Dykxhoorn et al. "Killing the Messenger: Short RNAs that Silence Gene Expression". Nature Reviews Molecular Cell Biology (2003) p. 457-467.
Elbashir et al., "Analysis of gene function in somatic mammalian cells using small interfering RNAs", 2002, Methods 26, pp. 199-213.
Elbashir et al., "Duplexes of 21-nucleotide RNAs mediate RNA interferences in cultured mammalian cells", Nature, May 24, 2001, vol. 411, pp. 494-498.
Elbashir et al., "Functional anatomy of siRNAs for mediating efficient RNAi in *Drosophila melanogaster* embryo lysate", The Embo Journal, 2001, vol. 20, No. 23, pp. 6877-6888.
Elbashir et al., "RNA interference is mediated by 21- and 22-nucleotide RNAs", Genes & Development, 2001, vol. 15, pp. 188-200.
Weitzer et al., "The human RNA kinase hCIpI is active on 3' transfer RNA exons and short interfering", RNAs. Nature., May 10, 2007, vol. 447, No. 7141, pp. 222-226.
Wess et al., "Managing complexity: early days for RNAi", Compugen, retrieved online at http://www.cgen.com/news.articles/article031703.html, 2003.
Whalen et al., "DNA-mediated immunization to the hepatitis B surface antigen. Activation and entrainment of the immune response." Annals of the New York Academy of Science. Nov. 27, 1995. 772, pp. 64-76.
Wianny et al., "Specific interference with gene function by double-stranded RNA in early mouse development", Nature Cell Biol., Feb. 2000, vol. 2, pp. 70-75.
Williams et al., "The respective roles of the protein kinase and pppA2'p5'A2'p5' A-activated endonuclease in the inhibition of protein synthesis by double-stranded RNA in rabbit reticulocyte lysates", Nucleic Acids Research, Apr. 1979, vol. 6, No. 4, pp. 1335-1350.
Woo et al., "G/C-modified oligodeoxynucleotides with selective complementarity: synthesis and hybridization properties", Nucleic Acids Res., Jul. 1, 1996, vol. 24, No. 13, pp. 2470-2475.
Written Demand for Invalidation Trial against Japanese Patent No. 4095895, dated Jul. 8, 2011 (Complete English Translation).
Written Demand for Invalidation Trial against Japanese Patent No. 4095895, dated Jul. 8, 2011.
Wu et al., "Human RNase III is a 160 kDa protein involved in preribosomal RNA processing", J. Biol. Chem., 2000, vol. 275, No. 47, pp. 36957-36965.
Wu et al., "Identification and partial purification of human double strand RNase activity", The Journal of Biological Chemistry, Jan. 30, 1998, vol. 273, No. 5, pp. 2532-2542.
Wu et al., "Properties of cloned and expressed human RNase HI" J. Biol. Chem., Oct. 1, 1999, vol. 274, No. 40, pp. 28270-28278.
Wu-Scharf et al., "Transgene and transposon silencing in *Chlamydomonas reinhardtii* by a DEAH-Box RNA helicase", Science, 2000, vol. 290, pp. 1159-1162.
Xia et al., "siRNA-mediated gene silencing in vitro and in vivo", Nature Biotechnology, 2002, vol. 20, pp. 1006-1010.
Xinhua, "The mechanism of RNase III action: now dicer dices", Abstract, Macromolecular Crystallography Laboratory, National Cancer Institute, 2008, pp. 99.
Yang et al., "Evidence that processed small dsRNAs may mediate sequence-specific mRNA degradation during RNAi in *Drosophila embryos*", Curr. Biol., 2000, vol. 10, pp. 1191-1200.

Yang et al., "Short RNA duplexes produced by hydrolysis with *Escherichia coli* RNase III mediate effective RNA interference in mammalian cells", PNAS, 2002, vol. 99, No. 15, pp. 9942-9947.
Yang et al., "Specific double-stranded RNA interference in undifferentiated mouse embryonic stem cells", Molecular and Cellular Biology, Nov. 2001, vol. 21, No. 22, pp. 7807-7816.
Yu et al., "RNA interference by expression of short-interfering RNAs and hairpin RNAs in mammalian cells", PNAS, Apr. 30, 2002, vol. 99, No. 9, pp. 6047-6052.
Zamore et al., "Ribo-gnome: the big world of small RNAs", Science, Sep. 2, 2005, vol. 309, No. 5740, pp. 1519-1524.
Zamore et al., "RNA interference: listening to the sound of silence", Nat. Struct. Biol., Sep. 2001, vol. 8, No. 9, pp. 746-750.
Zamore et al., "RNAi: double-stranded RNA directs the ATP-dependent cleavage of mRNA at 21 to 23 nucleotide intervals", Cell, Mar. 31, 2000, vol. 101, pp. 25-33.
Zamore et al., "siRNAs knock down hepatitis", Nature Medicine, 2003, vol. 9, No. 3, pp. 266-267.
Zamore et al., "Target dependent accumulation of small RNAs during RNAi in *C. elegans*", International *C. elegans* Meeting 2001, pp. 307.
Zamore et al., "The PUMILIO-RNA interaction: a single NA-binding domain monomer recognizes a bipartite target sequence", Biochemistry, 1999, vol. 38, pp. 596-604.
Zamore, "Ancient pathways programmed by small RNAs", Science, May 17, 2000, vol. 296, pp. 1265-1269.
Zelphati et al., "Antisense oligonucleotides in solution or encapsulated in immunoliposomes inhibit replication of HIV-1 by several different mechanisms", Nucleic Acids Research, 1994, vol. 22, No. 20, pp. 4307-4314.
Zeng et al., "Both natural and designed micro RNAs can inhibit the expression of cognate mRNAs when expressed in human cells", Molecular Cell, 2002, vol. 9, pp. 1327-1333.
Zeng, Yan and B. R. Cullen: "RNA interference in human cells is restricted to the cytoplasm", RNA, 2002, vol. 8, pp. 855-860.
Zhang et al., "Engineering mucosal RNA interference in vivo", Molecular Therapy, 2006, vol. 14, No. 3, pp. 336-342.
Zhang et al., "Human dicer preferentially cleaves dsRNAs at their termini without a requirement for ATP", The EMBO Journal, 2002, vol. 21, No. 21, pp. 5875-5885.
Zhang et al., "Regulation of ribonuclease III processing by double-helical sequence antideterminants", Proc. Natl. Acad. Sci. USA, 1997, vol. 94, pp. 13437-13441.
Zhang et al., "Single processing center models for human dicer and bacterial RNase III", Cell, Jul. 9, 2004, vol. 118, pp. 57-68.
Zhang et al., "Targeted gene silencing by small interfering RNA-based knock-down technology", Current Pharmaceutical Biotechnology, 2004, vol. 5, pp. 1-7.
Zhao et al., "Double-stranded RNA injection produces nonspecific defects in zebrafish", Dev. Biol., 2001, vol. 229, pp. 215-223.
Zheng, X. and P. C. Bevilacqua: "Activation ofthe protein kinase PKR by short double-stranded RNAs with single-stranded tails", RNA (2004), vol. 10, pp. 1934-1945.
Zhou et al., "Expression cloning of 2-5A-dependent RnAase: a uniquely regulated mediator of interferon action", Cell, Mar. 12, 1993, vol. 72, pp. 753-765.
Zhou et al., "Interferon action in triply deficient mice reveals the existence of alternative antiviral pathways", Virology, 1999, vol. 258, pp. 435-440.
Zimmermann et al., "RNAi-mediated gene silencing in non-human primates", Nature, 2006, vol. 441, pp. 111-114.
Bass, "Double-stranded RNA as a template for gene silencing", Cell, 2000, vol. 101, No. 3, pp. 235-238.
International Search Report dated Oct. 18, 2002 for PCT/US01/10188.
Extended European Search Report dated Jul. 22, 2011 for application No. 10184520.4.
Extended European Search Report dated May 27, 2011 for application No. 10184711.9.
Opposition Paper Submitted by Sanofi-Aventis (Opponent 1) in Response to the Summons to Attend Oral Proceedings in EP 1309726 dated Jan. 25, 2012.

(56) References Cited

OTHER PUBLICATIONS

Opposition Paper Submitted by Silence Therapeutics (Opponent 2) in Response to the Summons to Attend Oral Proceedings in EP 1309726 dated Jan. 27, 2012.
Opposition Paper Submitted by BASF (Opponent 3) in Response to the Summons to Attend Oral Proceedings in EP 1309726, dated Jan. 27, 2012.
Patentee's Submission in Response to the Summons to Attend Oral Proceedings in EP 1309726 dated Jan. 27, 2012.
Applicant's EPO Letter Opposition to EP 1309726 dated Oct. 28, 2008.
English Translation of Written Reply to the Written Demand for Invalidation Trial against Japanese Patent No. 4095895 dated Dec. 22, 2011.
U.S. Appl. No. 60/130,377, filed Apr. 21, 1999.
Lipinski, C. A. et al.: "Experimental and computational approaches to estimate solubility and permeability in drug discovery and development settings", Adv. Drug Delivery Reviews 23, pp. 3-25, 1997.
Liu et al., "Essential roles for caenorhabditis elegans lamin gene in nuclear organization, cell cycle progression, and spatial organization of nuclear pore complexes", Molecular Biology of the Cell, Nov. 2000, vol. 11, pp. 3937-3947.
Liu et al., "Mapping the 5' and 3' ends of Tetrahymena thermophila mRNAs using RNA ligase mediated amplification of cDNA ends (RLM-RACE)", Nucleic Acids Research, 1993, vol. 21, No. 21, pp. 4954-4960.
Liu et al., "Overlapping roles of two Hox genes and the exd orthology ceh-20 in diversification of the *C. elegans* postembryonic mesoderm", Development, 2000, vol. 127, pp. 5179-5190.
Liu et al., "R2D2, a bridge between the initiation and effector steps of the *Drosophila* RNAi pathway", Science, Sep. 26, 2003, vol. 301, pp. 1921-1925.
Lohmann et al., "Silencing of developmental genes in hydra", Developmental Biology, 1999, vol. 214, pp. 211-214.
Lu et al. (2008) Methods in Molecular Biology, vol.437: Drug Delivery Systems—Chapter 3: Delivering Small Interfering RNA for Novel Therapeutics.
Lu et al., "Delivering siRNA in vivo for functional genomics and novel therapeutics", RNA Interference Technology, 2005, pp. 303-317.
Lu et al., "Delivering small interfering RNA for novel therapeutics", Drug Delivery Systems, Chapter 3, pp. 93-107.
Lucy et al., "Suppression of post-transcriptional gene silencing by a plant viral protein localized in the nucleus", EMBO J., 2000, vol. 19, pp. 1672-1680.
Lutz et al., "Differential discrimination of DNA polymerase for variants of the non-stranded nucleobase pair between xanthosine and 2,4-diaminopyrimidine, two components of an expanded genetic alphabet", Nucleic Acids Res., Apr. 1, 1996, vol. 24, No. 7, pp. 1308-1313.
Ma et al., "Structural basis for 5'-end-specific recognition of guide RNA by the *A. fulgidus* Piwi protein", Nature, Mar. 31, 2005, vol. 434, No. 7033, pp. 666-670.
Ma et al., "Structural basis for overhang-specific small interfering RNA recognition by the PAZ domain," Nature, May 20, 2004, vol. 429, pp. 318-322.
Ma, M. Y-X. et al.: "Design and Synthesis of RNA Miniduplexes via a Synthetic Linker Approach", Biochemistry, Feb. 23, 1993; vol. 32, No. 7, pp. 1751-1758.
Mahato et al., "Modulation of gene expression by antisense and antigene oligodeoxynucleotides and small interfering RNA", Expert Opinion on Drug Delivery, 2005, vol. 2, No. 1, pp. 3-28.
Main request for dismissal of appeals in the opposition proceeding against European Patent No. 1 407 044 (Application No. 01985833.1), submitted by patentee, dated Nov. 10, 2011, 61 pages.
Maine et al., "A conserved mechanism for post-transcriptional gene silencing", Genome Biology, 2000, vol. 1, No. 3, pp. 1018.1-1018.4.
Majlessi et al., "Advantages of 2'-0-methyl oligoribonucleotide probes for detecting RNA targets", Nucleic Acids Research, 1998, vol. 26, No. 9, pp. 2224-2229.
Majumdar, A. et al.: "Targeted gene knockout mediated by triple helix forming oligonucleotides", Nat Genet Oct. 1998; vol. 20, No. 2, pp. 212-214.
Mallory et al., "MicroRNAs: something important between the genes", Curr. Opin. Plant Biol., Apr. 2004, vol. 7, No. 2, pp. 120-125.
Manche et al., "Interactions between double-stranded RNA regulators and the protein kinase DAI", Molecular and Cellular Biology, Nov. 1992, vol. 12, No. 11, pp. 5238-5248.
Marcus et al., "Defective interfering particles with covalently linked [+/] RNA induce interferon", Nature, Apr. 28, 1977, vol. 266, No. 5606, pp. 815-819.
Marques et al., "Activation of the mammalian immune system by SiRNAs," Nature Biotechnology, Nov. 23, 2005, vol. 11, pp. 1399-1405.
Martinez et al., "Single-stranded antisense siRNAs guide target RNA cleaveage in RNAi", Cell, 2002, vol. 110, pp. 563-574.
Martinez et al., "Synthetic small inhibiting RNAs: efficient tools to inactivate oncogenic mutations and restrore p53 pathways", PNAS, 2002, vol. 99, No. 23, pp. 14849-14854.
Martinez, J. and T. Tuschl: "RISC is a 5' phosphomonoester-producing RNA endonuclease", Genes & Dev., vol. 18, No. 9, pp. 975-980, 2004.
Mathews et al., "Adenovirus virus-associated RNA and translation control", J. Virol., 1991, vol. 6, No. 11, pp. 5657-5662.
Matranga et al., "Passenger-stranded cleavage facilitates assembly of siRNA into Agog-containing RNAi enzyme complexes", Cell, Nov. 18, 2005, vol. 123, pp. 607-620.
Matsuda et al., "Molecular cloning and characterization of a novel human gene (HERNA) which encodes a putative RNA-helicase", Biochimica et Biophysica Acta, 2000, vol. 1490, pp. 163-169.
Matzke et al., "RNA-based silencing strategies in plants", Curr. Opin. Genet. Dev., Apr. 2001, vol. 11, No. 2, pp. 221-227.
Matzke et al., "RNAi extends its reach", Science, Aug. 22, 2003, vol. 301, No. 5636, pp. 1060-1061.
Matzke et al., "RNAi-mediated pathways in the nucleus", Nat. Rev. Genet., Jan. 2005, vol. 6, No. 1, pp. 24-35.
McCaffrey et al., "RNA interference in adult mice", Nature, Jul. 4, 2002, vol. 418, pp. 38-39.
McManus et al., "Gene silencing in mammals by small interfering RNAs", Reviews, pp. 737-747.
McManus et al., "Gene silencing using micro-RNA designed hairpins", RNA, 2002, vol. 8, pp. 842-850.
McManus et al., "Small interfering RNA-mediated gene silencing in T lymphocytes", The Journal of Immunology, 2002, vol. 169, pp. 5754-5760.
Meister et al., "Mechanisms of gene silencing by double-stranded RNA", Nature, Sep. 16, 2004, vol. 431, pp. 343-349.
Meister, G., "RNA Interference in the Nucleus," Science, vol. 321, Jul. 25, 2008, pp. 496-541.
Mello et al., "Revealing the world of Rna interference", Nature, Sep. 16, 2004, vol. 431, No. 7006, pp. 338-342.
Mello, "Return to the RNAi World: Rethinking Gene Expression and Evolution," Nobel Lecture, Dec. 8, 2006.
Memorandum in Support of Max Planck's and Alnylam's Motions for Temporary Restraining Order and Preliminary Injunction. Civil Action No. 09-2674. *Max-Planck-Gesellschaft zur Förderung der Wissenschaften e.V.* v. *Whitehead Institute for Biomedical Research, et al.* Dated Jun. 30, 2009.
Mercola et al., "Antisense approaches to cancer gene therapy", Cancer Gene Therapy, 1995, vol. 2, No. 1, pp. 47-59.
Milhaud, P. G. et al.: "Free and Liposome-Encapsulated Double-Stranded RNAs as Inducers of Interferon, Interleukin-6 and Cellular Toxicity", Journal of Interferon Research, 1991, vol. 11, pp. 261-265.
Milligan et al., "Synthesis of small RNAs using T7 RNA polymerase", Methods in Enzymology, 1989, vol. 180, pp. 51-62.
Minks, M. A.: "Structural Requirements of Double-stranded RNA for the Activation of 2',5'-Oligo(A) Polymerase and Protein Kinase of Interferon-treated HeLa Cells", The Journal of Biological Chemistry, vol. 254, No. 20, issue of Oct. 25, pp. 10180-10183, 1979.
Misquitta et al., "Targeted disruption of gene function in Drosophila by RNA interference (RNA-i): a role for nautilus in embryonic somatic muscle formation", Proc. Natl. Acad. Sci. USA, 1999, vol. 96, pp. 1451-1456.

(56) References Cited

OTHER PUBLICATIONS

Miyagishi et al., "U6 promoter-drive siRNAs with four uridine 3' overhangs efficiently suppress targeted gene expression in mammalian cells", Nature Biotechnology, 2002, vol. 19, pp. 497-500.
Molenaar et al., "Linear 2'0-methyl RNA probes for the visualization of RNA in living cells", Nucleic Acids Research, 2001, vol. 29, No. 17, pp. 1-9.
Monia et al., "Evaluation of 2'-modified oligonucleotides containing 2'-deoxy gaps as antisense inhibitors of gene expression", J. Biol. Chem., Jul. 5, 1993, vol. 268, No. 19, pp. 14514-14522.
Monia et al., "Selective inhibition of mutant Ha-ras mRNA expression by antisense oligonucleotides", J. Biol. Chem., Oct. 5, 1992, vol. 267, No. 28, pp. 19954-19962.
Case 1:09-cv-11116-PBS. Deposition Testimony of Anne Collins; Oct. 30, 2009.
Case 1:09-cv-11116-PBS. Deposition Testimony of Anne Collins; Oct. 30, 2009; associated Exhibits previously marked 2 through 4 and 530 through 545.
Case 1:09-cv-11116-PBS. Deposition Testimony of David Bartel; Nov. 23, 2009.
Case 1:09-cv-11116-PBS. Deposition Testimony of David Bartel; Nov. 23, 2009; associated Exhibits 771 through 775.
Case 1:09-cv-11116-PBS. Deposition Testimony of Helen Lockhart; day 1; Nov. 24, 2009.
Case 1:09-cv-11116-PBS. Deposition Testimony of Helen Lockhart; day 1; Nov. 24, 2009; associated Exhibits 850 through 877.
Case 1:09-cv-11116-PBS. Deposition Testimony of Helen Lockhart; day 2; Dec. 15, 2009.
Case 1:09-cv-11116-PBS. Deposition Testimony of Helen Lockhart; day 2; Dec. 15, 2009; associated Exhibits 902 through 914.
Case 1:09-cv-11116-PBS. Deposition Testimony of Monica Chin Kitts; Dec. 9, 2009.
Case 1:09-cv-11116-PBS. Deposition Testimony of Monica Chin Kitts; Dec. 9, 2009; associated Exhibits 231 through 248.
Case 1:09-cv-11116-PBS. Deposition Testimony of Patricia Granahan; Nov. 17, 2009.
Case 1:09-cv-11116-PBS. Deposition Testimony of Patricia Granahan; Dec. 9, 2009; associated Exhibits 637 through 645.
Case 1:09-cv-11116-PBS. Deposition Testimony of Phillip Sharp; Nov. 30, 2009.
Case 1:09-cv-11116-PBS. Deposition Testimony of Philip Sharp; Nov. 30, 2009; associated Exhibits 785 through 789.
Case 1:09-cv-11116-PBS. Deposition Testimony of Philip D. Zamore, PhD.; Nov. 25, 2009, associated Exhibits 781-784.
Case 1:09-cv-11116-PBS. Deposition Testimony of Phillip D. Zamore, PhD.; Nov. 24, 2009, associated Exhibits 776-780.
Case 1:09-cv-11116-PBS. Deposition Testimony of Robert Murray; Oct. 26, 2009.
Case 1:09-cv-11116-PBS. Deposition Testimony of Robert Murray; Oct. 26, 2009; associated Exhibits 18 through 26.
Case 1:09-cv-11116-PBS. Deposition Testimony of Sayda Elbashir; Nov. 20, 2009.
Case 1:09-cv-11116-PBS. Deposition Testimony of Sayda Elbashir; Nov. 20, 2009; associated Exhibits 163 through 168.
Case 1:09-cv-11116-PBS. Deposition Testimony of Thomas Tuschl; Day 1; Nov. 6, 2009.
Case 1:09-cv-11116-PBS. Deposition Testimony of Thomas Tuschl; Day 1; Nov. 6, 2009; associated Exhibits 27 through 58.
Case 1:09-cv-11116-PBS. Deposition Testimony of Thomas Tuschl; Day 2; Nov. 19, 2009.
Case 1:09-cv-11116-PBS. Deposition Testimony of Thomas Tuschl; Day 2; Nov. 19, 2009; associated Exhibits 150 through 162.
Case 1:09-cv-11116-PBS. Deposition Testimony of Winfried Lendeckel; Nov. 14, 2009.
Case 1:09-cv-11116-PBS. Deposition Testimony of Winfried Lendeckel; Nov. 14, 2009; associated Exhibits 108 through 114.
English translation of International Preliminary Examination Report for PCT/DE2000/00244 dated May 9, 2001.
PCT International Search Report for PCT/US01/10188, mailed Oct. 18, 2002.
Confidential Settlement Agreement and Mutual Release dated Mar. 15, 2011 as provided in Exhibit 10.2 of Alnylarn Pharmaceuticals Inc.'s 10-Q SEC Quarterly Report filed on May 5, 2011.
Interlocutory Decision Issued by Opposition Division in Opposition Proceedings to EP 1309726 dated Mar. 30, 2012.
Ho et al. "Mapping of RNA Accessible Sites for Antisense Experiments with Oligonucleotide Libraries". Nature Biotechnology, vol. 16, Jan. 1998, pp. 59-63.
Declaration of Wolfgang Weiss, Under 35 U.S.C. §1.132, dated Jan. 7, 2009.
Case 1:11-cv-10484-PBS. Document 60. Memorandum in Opposition to the Official Capacity Defendant's Motion to Dismiss University of Utah's Second Amended complaint. Filed Mar. 21, 2012.
Case 1:11-cv-10484-PBS. Document 61. Memorandum in Opposition to Defendant's Motion to Dismiss University of Utah's Second Amended Complaint. Filed Mar. 21, 2012.
Case 1:11-cv-10484-PBS. Document 62 and Associated Exhibits. Declaration of Steve W. Berman in Support of Memoranda in Opposition to All Defendant's Motions to Dismiss University of Utah's Second Amended Complaint. Filed Mar. 21, 2012.
Case 1:11-cv-10484-PBS. Document 64. Reply in Support of Defendant's Motion to Dismiss University of Utah's Second Amended Complaint. Filed Apr. 18, 2012.
Case 1:11-cv-10484-PBS. Document 65. Reply in Support of Official Capacity Defendant's Motion to Dismiss University of Utah's Second Amended Complaint. Filed Apr. 18, 2012.
Case 1:11-cv-10484-PBS. Document 66. Surreply in Opposition to Defendants' Motion to Dismiss University of Utah's Second Amended Complaint. Filed May 9, 2012.
Case 1:11-cv-10484-PBS. Document 67. Surreply in Opposition to the Official Capacity Defendants' Motion to Dismiss University of Utah's Second Amended Complaint. Filed May 9, 2012.
Case 1:11-cv-10484-PBS. Document 68. Notice of Voluntary Dismissal of Counts VI (Conversion) and VII (Replevin) and Request to Strike Certain Matter from Paragaphs G and H of Prayer for Relief (Assignment) of the Second Amended Complaint. Filed May 21, 2012.
Case 1:11-cv-10484-PBS. Document 69. Defendant's Response to Plaintiffs Notice of Voluntary Dismissal of Counts VI (Conversion) and VII (Replevin) and Request to Strike Certain Matter from Paragraphs G and H of Prayer for Relief (Assignment) of the Second Amended Complaint. Filed May 25, 2012.
Case 1:11-cv-10484-PBS. Document 70. Memorandum and Order Denying Motions to Dismiss. Filed Jun. 11, 2012.
Dykxhoorn, D.M. and Lieberman, J., "The Silent Revolution: RNA Interference as Basic Biology, Research Tool, and Therapeutic," Annu. Rev. Med., 56:401-423 (2005).
Zhou, M-Yi, et al., "In Vivo Expression of Neutorphil Inhibitory Factor via Gene Transfer Prevents Lipopolysaccaride-Induced Lung Neutrophil Infiltration and Injury by a Beta2 Integrin-Dependent Mechanism," J. Clin. Invest., 101 (11):2427-2437 (1998).
Nogawa, M., et al., "Intravesical Administration of Small Interfering RNA Targeting PLK-1 Successfully Prevents the Growth of Bladder Cancer," The Journal of Clinical Investigation, 115(4):978 (2005).
Sato, A. et al., "Small Interfering RNA Delivery to the Liver by Intravenous Administration of Galactosylated Cationic Liposomes in Mice," Biomaterials, 28:1434-1442 (2007).
U.S. Appl. No. 60/279,661, filed Mar. 30, 2001.
U.S. Appl. No. 09/889,802, filed Sep. 17, 2001.
U.S. Appl. No. 60/117,635, filed Jan. 28, 1999.
Appeal Brief submitted by Sanofi-Aventis dated Aug. 9, 2012 against the Interlocutory Decision dated Mar. 30, 2012 in the opposition proceedings in EP 1309726.
Appeal Brief submitted by Silence Therapeutics dated Aug. 9, 2012 against the Interlocutory Decision dated Mar. 30, 2012 in the opposition proceedings in EP 1309726.
Case 1:11-cv-10484-PBS. Document 71. Transcript of Motion Hearing on May 30, 2012. Release of Transcript Restriction Set for Sep. 10, 2012.

(56) References Cited

OTHER PUBLICATIONS

Case 1:11-cv-10484-PBS. Document 73. Defendent's Answer to the University of Utah's Second Amended Complaint filed Jun. 25, 2012.

Decision from the U.S. Court of Appeals, District Court of Massachusetts, No. 11-CV-10484, *University of Utah* vs. *Max-Planck-Gesellschaft, et al.*, Decision dated Aug. 19, 2013.

English translation of the Decision in the Patent Invalidation Trial of Japanese Patent No. 4095895, mailed Sep. 28, 2012.

GenBank, NCBI Reference Sequence: NM_002234.3, *Homo sapiens* potassium voltage-gated channel, shaker-related subfamily, member 5 (KCNA5) mRNA, dated Jun. 7, 2013.

GenBank, NCBI Reference Sequence: NM_022904.1, *Homo sapiens* RAS protein activator like 3 (RASAL3) mRNA, dated Jun. 7, 2013.

Proprietor's Response to the Grounds of Appeal, Including the Main and Auxiliary Requests, filed Jan. 7, 2013, in the Opposition Proceedings in EP 1309726.

Wikipedia Entry for "RNaseH" Current as of Jan. 3, 2013, Cited in the Opposition Proceedings in EP 1309726 on Jan. 7, 2013.

7mG*pppGAAUACAAGCUUGGGCCUAGCCACCAUGACUUCGAAAGUUUAUGAUCC
AGAACAAAGGAAACGGAǗGAUAACUGGUCCGCAGUGGUGGGCCAGAUG
UAAACAAAUGAAUGUUCUUGAUUCAUUUAUUAAUUAUUAUGAUUCAGAAA
AACAUGCAGAAAAUGCUGUUAUUUUUUUACAUGGUAACGCGGCCUCUU
CUUAUUUAUGGCGACAUGUUGUGCCACAUAUUGAGCCAGUAGCGCGGU
GUAUUAUACCAGACCUUAUUGGUAU... (SEQ ID NO: 1)

Fig. 10

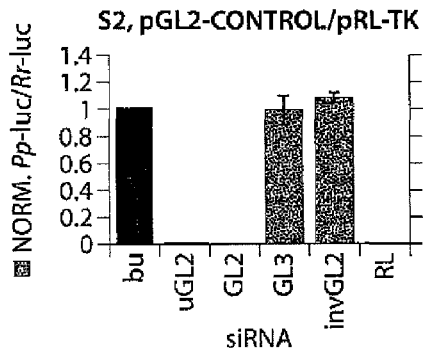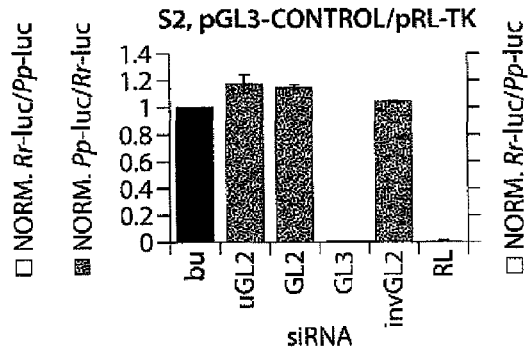
Fig. 15A  Fig. 15B
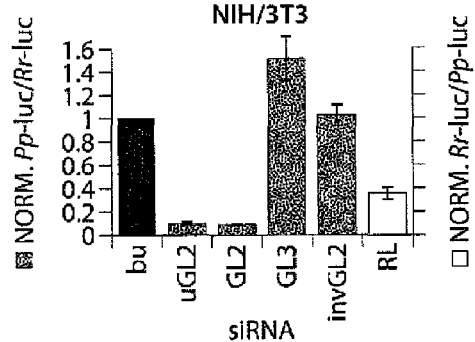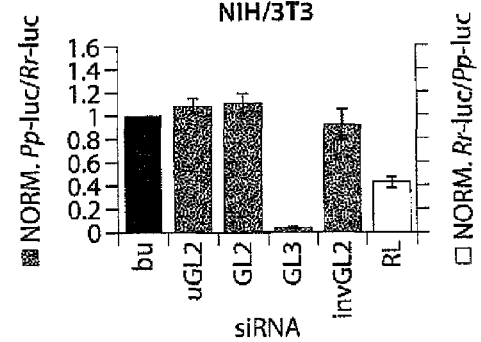
Fig. 15C  Fig. 15D
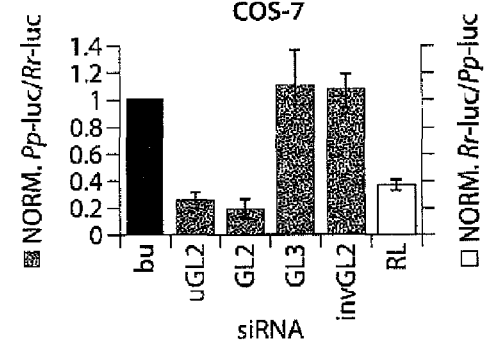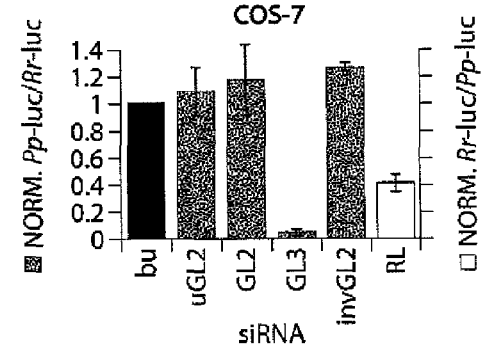
Fig. 15E  Fig. 15F

RNA SEQUENCE-SPECIFIC MEDIATORS OF RNA INTERFERENCE

This application is a continuation of U.S. application Ser. No. 11/474,930, entitled "RNA SEQUENCE-SPECIFIC MEDIATORS OF RNA INTERFERENCE" filed on Jun. 26, 2006 now abandoned, which is herein incorporated by reference in its entirety. Application Ser. No. 11/474,930 is a divisional of U.S. application Ser. No. 09/821,832, entitled "RNA SEQUENCE-SPECIFIC MEDIATORS OF RNA INTERFERENCE" filed on Mar. 30, 2001 now abandoned, which is herein incorporated by reference in its entirety. Application Ser. No. 09/821,832 claims priority under 35 U.S.C. §119(e) to U.S. Provisional Application Ser. No. 60/193,594, entitled "RNA SEQUENCE-SPECIFIC MEDIATORS OF RNA INTERFERENCE" filed on Mar. 30, 2000, which is herein incorporated by reference in its entirety. Application Ser. No. 09/821,832 claims priority under 35 U.S.C. §119(e) to U.S. Provisional Application Ser. No. 60/265,232, entitled "RNA SEQUENCE-SPECIFIC MEDIATORS OF RNA INTERFERENCE" filed on Jan. 31, 2001, which is herein incorporated by reference in its entirety. Application Ser. No. 09/821,832 claims priority under 35 U.S.C. §119 to European Application No. 00 126 325.0 filed on Dec. 1, 2000, which is herein incorporated by reference in its entirety.

GOVERNMENT SUPPORT

This invention was made with government support under Grant No. GM034277 awarded by the National Institutes of Health. The government has certain rights in the invention.

BACKGROUND OF THE INVENTION

RNA interference or "RNAi" is a term initially coined by Fire and co-workers to describe the observation that double-stranded RNA (dsRNA) can block gene expression when it is introduced into worms (Fire et al. (1998) Nature 391, 806-811). dsRNA directs gene-specific, post-transcriptional silencing in many organisms, including vertebrates, and has provided a new tool for studying gene function. RNAi involves mRNA degradation, but many of the biochemical mechanisms underlying this interference are unknown. The recapitulation of the essential features of RNAi in vitro is needed for a biochemical analysis of the phenomenon.

SUMMARY OF THE INVENTION

Described herein is gene-specific, dsRNA-mediated interference in a cell-free system derived from syncytial blastoderm Drosophila embryos. The in vitro system complements genetic approaches to dissecting the molecular basis of RNAi. As described herein, the molecular mechanisms underlying RNAi were examined using the Drosophila in vitro system. Results showed that RNAi is ATP-dependent yet uncoupled from mRNA translation. That is, protein synthesis is not required for RNAi in vitro. In the RNAi reaction, both strands (sense and antisense) of the dsRNA are processed to small RNA fragments or segments of from about 21 to about 23 nucleotides (nt) in length (RNAs with mobility in sequencing gels that correspond to markers that are 21-23 nt in length, optionally referred to as 21-23 nt RNA). Processing of the dsRNA to the small RNA fragments does not require the targeted mRNA, which demonstrates that the small RNA species is generated by processing of the dsRNA and not as a product of dsRNA-targeted mRNA degradation. The mRNA is cleaved only within the region of identity with the dsRNA. Cleavage occurs at sites 21-23 nucleotides apart, the same interval observed for the dsRNA itself, suggesting that the 21-23 nucleotide fragments from the dsRNA are guiding mRNA cleavage. That purified 21-23 nt RNAs mediate RNAi confirms that these fragments are guiding mRNA cleavage.

Accordingly, the present invention relates to isolated RNA molecules (double-stranded; single-stranded) of from about 21 to about 23 nucleotides which mediate RNAi. That is, the isolated RNAs of the present invention mediate degradation of mRNA of a gene to which the mRNA corresponds (mediate degradation of mRNA that is the transcriptional product of the gene, which is also referred to as a target gene). For convenience, such mRNA is also referred to herein as mRNA to be degraded. As used herein, the terms RNA, RNA molecule(s), RNA segment(s) and RNA fragment(s) are used interchangeably to refer to RNA that mediates RNA interference. These terms include double-stranded RNA, single-stranded RNA, isolated RNA (partially purified RNA, essentially pure RNA, synthetic RNA, recombinantly produced RNA), as well as altered RNA that differs from naturally occurring RNA by the addition, deletion, substitution and/or alteration of one or more nucleotides. Such alterations can include addition of non-nucleotide material, such as to the end(s) of the 21-23 nt RNA or internally (at one or more nucleotides of the RNA). Nucleotides in the RNA molecules of the present invention can also comprise non-standard nucleotides, including non-naturally occurring nucleotides or deoxyribonucleotides. Collectively, all such altered RNAs are referred to as analogs or analogs of naturally-occurring RNA. RNA of 21-23 nucleotides of the present invention need only be sufficiently similar to natural RNA that it has the ability to mediate (mediates) RNAi. As used herein the phrase "mediates RNAi" refers to (indicates) the ability to distinguish which RNAs are to be degraded by the RNAi machinery or process. RNA that mediates RNAi interacts with the RNAi machinery such that it directs the machinery to degrade particular mRNAs. In one embodiment, the present invention relates to RNA molecules of about 21 to about 23 nucleotides that direct cleavage of specific mRNA to which their sequence corresponds. It is not necessary that there be perfect correspondence of the sequences, but the correspondence must be sufficient to enable the RNA to direct RNAi cleavage of the target mRNA. In a particular embodiment, the 21-23 nt RNA molecules of the present invention comprise a 3' hydroxyl group.

The present invention also relates to methods of producing RNA molecules of about 21 to about 23 nucleotides with the ability to mediate RNAi cleavage. In one embodiment, the Drosophila in vitro system is used. In this embodiment, dsRNA is combined with a soluble extract derived from Drosophila embryo, thereby producing a combination. The combination is maintained under conditions in which the dsRNA is processed to RNA molecules of about 21 to about 23 nucleotides. In another embodiment, the Drosophila in vitro system is used to obtain RNA sequences of about 21 to about 23 nucleotides which mediate RNA interference of the mRNA of a particular gene (e.g., oncogene, viral gene). In this embodiment, double-stranded RNA that corresponds to a sequence of the gene to be targeted is combined with a soluble extract derived from Drosophila embryo, thereby producing a combination. The combination is maintained under conditions in which the double-stranded RNA is processed to RNA of about 21 to about 23 nucleotides in length. As shown herein, 21-23 nt RNA mediates RNAi of the mRNA of the targeted gene (the gene whose mRNA is to be degraded). The method of obtaining 21-23 nt RNAs using the Drosophila in vitro system can further comprise isolating the RNA sequence from the combination.

The present invention also relates to 21-23 nt RNA produced by the methods of the present invention, as well as to 21-23 nt RNAs, produced by other methods, such as chemical synthesis or recombinant DNA techniques, that have the same or substantially the same sequences as naturally-occurring RNAs that mediate RNAi, such as those produced by the methods of the present invention. All of these are referred to as 21-23 nt RNAs that mediate RNA interference. As used herein, the term isolated RNA includes RNA obtained by any means, including processing or cleavage of dsRNA as described herein; production by chemical synthetic methods; and production by recombinant DNA techniques. The invention further relates to uses of the 21-23 nt RNAs, such as for therapeutic or prophylactic treatment and compositions comprising 21-23 nt RNAs that mediate RNAi, such as pharmaceutical compositions comprising 21-23 nt RNAs and an appropriate carrier (e.g., a buffer or water).

The present invention also relates to a method of mediating RNA interference of mRNA of a gene in a cell or organism (e.g., mammal such as a mouse or a human). In one embodiment, RNA of about 21 to about 23 nt which targets the mRNA to be degraded is introduced into the cell or organism. The cell or organism is maintained under conditions under which degradation of the mRNA occurs, thereby mediating RNA interference of the mRNA of the gene in the cell or organism. The cell or organism can be one in which RNAi occurs as the cell or organism is obtained or a cell or organism can be one that has been modified so that RNAi occurs (e.g., by addition of components obtained from a cell or cell extract that mediate RNAi or activation of endogenous components). As used herein, the term "cell or organism in which RNAi occurs" includes both a cell or organism in which RNAi occurs as the cell or organism is obtained, or a cell or organism that has been modified so that RNAi occurs. In another embodiment, the method of mediating RNA interference of a gene in a cell comprises combining double-stranded RNA that corresponds to a sequence of the gene with a soluble extract derived from *Drosophila* embryo, thereby producing a combination. The combination is maintained under conditions in which the double-stranded RNA is processed to RNAs of about 21 to about 23 nucleotides. 21 to 23 nt RNA is then isolated and introduced into the cell or organism. The cell or organism is maintained under conditions in which degradation of mRNA of the gene occurs, thereby mediating RNA interference of the gene in the cell or organism. As described for the previous embodiment, the cell or organism is one in which RNAi occurs naturally (in the cell or organism as obtained) or has been modified in such a manner that RNAi occurs. 21 to 23 nt RNAs can also be produced by other methods, such as chemical synthetic methods or recombinant DNA techniques.

The present invention also relates to biochemical components of a cell, such as a *Drosophila* cell, that process dsRNA to RNA of about 21 to about 23 nucleotides. In addition, biochemical components of a cell that are involved in targeting of mRNA by RNA of about 21 to about 23 nucleotides are the subject of the present invention. In both embodiments, the biochemical components can be obtained from a cell in which they occur or can be produced by other methods, such as chemical synthesis or recombinant DNA methods. As used herein, the term "isolated" includes materials (e.g., biochemical components, RNA) obtained from a source in which they occur and materials produced by methods such as chemical synthesis or recombinant nucleic acid (DNA, RNA) methods.

The present invention also relates to a method for knocking down (partially or completely) the targeted gene, thus providing an alternative to presently available methods of knocking down (or out) a gene or genes. This method of knocking down gene expression can be used therapeutically or for research (e.g., to generate models of disease states, to examine the function of a gene, to assess whether an agent acts on a gene, to validate targets for drug discovery). In those instances in which gene function is eliminated, the resulting cell or organism can also be referred to as a knockout. One embodiment of the method of producing knockdown cells and organisms comprises introducing into a cell or organism in which a gene (referred to as a targeted gene) is to be knocked down, RNA of about 21 to about 23 nt that targets the gene and maintaining the resulting cell or organism under conditions under which RNAi occurs, resulting in degradation of the mRNA of the targeted gene, thereby producing knockdown cells or organisms. Knockdown cells and organisms produced by the present method are also the subject of this invention.

The present invention also relates to a method of examining or assessing the function of a gene in a cell or organism. In one embodiment, RNA of about 21 to about 23 nt which targets mRNA of the gene for degradation is introduced into a cell or organism in which RNAi occurs. The cell or organism is referred to as a test cell or organism. The test cell or organism is maintained under conditions under which degradation of mRNA of the gene occurs. The phenotype of the test cell or organism is then observed and compared to that of an appropriate control cell or organism, such as a corresponding cell or organism that is treated in the same manner except that the targeted (specific) gene is not targeted. A 21 to 23 nt RNA that does not target the mRNA for degradation can be introduced into the control cell or organism in place of the RNA introduced into the test cell or organism, although it is not necessary to do so. A difference between the phenotypes of the test and control cells or organisms provides information about the function of the degraded mRNA. In another embodiment, double-stranded RNA that corresponds to a sequence of the gene is combined with a soluble extract that mediates RNAi, such as the soluble extract derived from *Drosophila* embryo described herein, under conditions in which the double-stranded RNA is processed to generate RNA of about 21 to about 23 nucleotides. The RNA of about 21 to about 23 nucleotides is isolated and then introduced into a cell or organism in which RNAi occurs (test cell or test organism). The test cell or test organism is maintained under conditions under which degradation of the mRNA occurs. The phenotype of the test cell or organism is then observed and compared to that of an appropriate control, such as a corresponding cell or organism that is treated in the same manner as the test cell or organism except that the targeted gene is not targeted. A difference between the phenotypes of the test and control cells or organisms provides information about the function of the targeted gene. The information provided may be sufficient to identify (define) the function of the gene or may be used in conjunction with information obtained from other assays or analyses to do so.

Also the subject of the present invention is a method of validating whether an agent acts on a gene. In this method, RNA of from about 21 to about 23 nucleotides that targets the mRNA to be degraded is introduced into a cell or organism in which RNAi occurs. The cell or organism (which contains the introduced RNA) is maintained under conditions under which degradation of mRNA occurs, and the agent is introduced into the cell or organism. Whether the agent has an effect on the cell or organism is determined; if the agent has no effect on the cell or organism, then the agent acts on the gene.

The present invention also relates to a method of validating whether a gene product is a target for drug discovery or development. RNA of from about 21 to about 23 nucleotides that targets the mRNA that corresponds to the gene for degradation is introduced into a cell or organism. The cell or organism is maintained under conditions in which degradation of the mRNA occurs, resulting in decreased expression of the gene. Whether decreased expression of the gene has an effect on the cell or organism is determined, wherein if decreased expression of the gene has an effect, then the gene product is a target for drug discovery or development.

The present invention also encompasses a method of treating a disease or condition associated with the presence of a protein in an individual comprising administering to the individual RNA of from about 21 to about 23 nucleotides which targets the mRNA of the protein (the mRNA that encodes the protein) for degradation. As a result, the protein is not produced or is not produced to the extent it would be in the absence of the treatment.

Also encompassed by the present invention is a gene identified by the sequencing of endogenous 21 to 23 nucleotide RNA molecules that mediate RNA interference.

Also encompassed by the present invention is a method of identifying target sites within an mRNA that are particularly suitable for RNAi as well as a method of assessing the ability of 21-23 nt RNAs to mediate RNAi.

BRIEF DESCRIPTION OF DRAWINGS

The file of this patent contains at least one drawing executed in color. Copies of this patent with color drawing(s) will be provided by the Patent and Trademark Office upon request and payment of the necessary fee.

FIG. 1 discloses "$A_{25}$" as SEQ ID NO: 20.

FIG. 9 discloses "$A_{25}$" as SEQ ID NO: 20.

FIG. 10 indicates the cleavage sites mapped onto the first 267 nt of the Rr-luc mRNA (SEQ ID NO: 1). The blue bar below the sequence indicates the position of dsRNA 'C,' and blue circles indicate the position of cleavage sites caused by this dsRNA. The green bar denotes the position of dsRNA 'B,' and green circles, the cleavage sites. The magenta bar indicates the position of dsRNA 'A,' and magenta circles, the cleavages. An exceptional cleavage within a run of 7 uracils is marked with a red arrowhead.

FIG. 14A illustrates the firefly (Pp-luc) and sea pansy (Rr-luc) luciferase reporter gene regions from plasmids pGL2-Control, pGL3-Control, and pRL-TK (Promega). SV40 regulatory elements, the HSV thymidine kinase promoter, and two introns (lines) are indicated. The sequence of GL3 luciferase is 95% identical to GL2, but RL is completely unrelated to both. Luciferase expression from pGL2 is approximately to 10-fold lower than from pGL3 in transfected mammalian cells. The region targeted by the siRNA duplexes is indicated as black bar below the coding region of the luciferase genes. FIG. 14B shows the sense (top) and antisense (bottom) sequences of the siRNA duplexes targeting GL2 (SEQ ID Nos: 10 and 11), GL3 (SEQ ID Nos: 12 and 13), and RL (SEQ ID Nos: 14 and 15) luciferase are shown. The GL2 and GL3 siRNA duplexes differ by only 3 single nucleotide substitutions (boxed in gray). As unspecific control, a duplex with the inverted GL2 sequence, invGL2 (SEQ ID Nos: 16 and 17), was synthesized. The 2 nt 3' overhang of 2'-deoxythymidine is indicated as TT; uGL2 (SEQ ID Nos: 18 and 19) is similar to GL2 siRNA but contains ribo-uridine 3' overhangs.

FIGS. 15A-15J are graphs showing RNA interference by siRNA duplexes. Ratios of target to control luciferase were normalized to a buffer control (bu, black bars); gray bars indicate ratios of *Photinus pyralis* (Pp-luc) GL2 or GL3 luciferase to *Renilla reniformis* (Rr-luc) RL luciferase (left axis), white bars indicate RL to GL2 or GL3 ratios (right axis). FIGS. 15A, 15C, 15E, 15G, and 15I show results of experiments performed with the combination of pGL2-Control and pRL-TK reporter plasmids, FIGS. 15B, 15D, 15F, 15H, and 15J with pGL3-Control and pRL-TK reporter plasmids. The cell line used for the interference experiment is indicated at the top of each plot. The ratios of Pp-luc/Rr-luc for the buffer control (bu) varied between 0.5 and 10 for pGL2/pRL, and between 0.03 and 1 for pGL3/pRL, respectively, before normalization and between the various cell lines tested. The plotted data were averaged from three independent experiments±S.D. FIGS. 16A, 16C, and 16E describe experiments performed with pGL2-Control and pRL-TK reporter plasmids, FIGS. 16B, 16D, and 16F with pGL3-Control and pRL-TK reporter plasmids. The data were averaged from two independent experiments±S.D. FIGS. 16A, 16B, Absolute Pp-luc expression, plotted in arbitrary luminescence units. FIG. 16C, 16D, Rr-luc expression, plotted in arbitrary luminescence units. FIGS. 16E, 16F, Ratios of normalized target to control luciferase. The ratios of luciferase activity for siRNA duplexes were normalized to a buffer control (bu, black bars); the luminescence ratios for 50 or 500 bp dsRNAs were normalized to the respective ratios observed for 50 and 500 bp dsRNA from humanized GFP (hG, black bars). It should be noted, that the overall differences in sequence between the 49 and 484 bp dsRNAs targeting GL2 and GL3 are not sufficient to confer specificity between GL2 and GL3 targets (43 nt uninterrupted identity in 49 bp segment, 239 nt longest uninterrupted identity in 484 bp segment) (Parrish, S., et al., Mol. Cell, 6:1077-1087 (2000)).

DETAILED DESCRIPTION OF THE INVENTION

Figure 1:
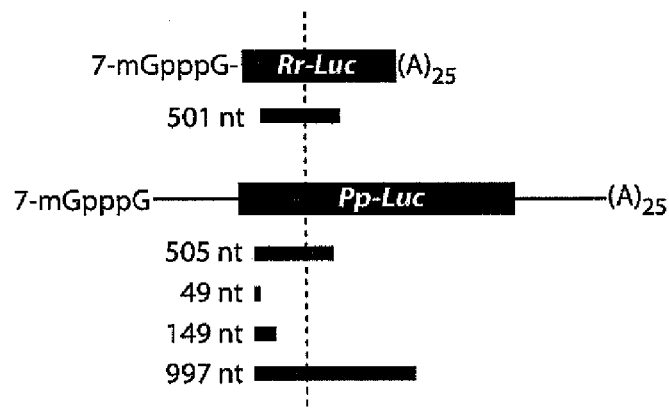
FIG. 1 is a schematic representation of reporter mRNAs and dsRNAs Rr-Luc and Pp-Luc. Lengths and positions of the ssRNA, asRNA, and dsRNAs are shown as black bars relative to the Rr-Luc and Pp-Luc reporter mRNA sequences. Black rectangles indicate the two unrelated luciferase coding sequences, lines correspond to the 5' and 3' untranslated regions of the mRNAs.

Double-stranded (dsRNA) directs the sequence-specific degradation of mRNA through a process known as RNA interference (RNAi). The process is known to occur in a wide variety of organisms, including embryos of mammals and other vertebrates. Using the *Drosophila* in vitro system described herein, it has been demonstrated that dsRNA is processed to RNA segments 21-23 nucleotides (nt) in length, and furthermore, that when these 21-23 nt fragments are purified and added back to *Drosophila* extracts, they mediate RNA interference in the absence of longer dsRNA. Thus, these 21-23 nt fragments are sequence-specific mediators of RNA degradation. A molecular signal, which may be the specific length of the fragments, must be present in these 21-23 nt fragments to recruit cellular factors involved in RNAi. This present invention encompasses these 21-23 nt fragments and their use for specifically inactivating gene function. The use of these fragments (or recombinantly produced or chemically synthesized oligonucleotides of the same or similar nature) enables the targeting of specific mRNAs for degradation in mammalian cells. Use of long dsRNAs in mammalian cells to elicit RNAi is usually not practical, presumably because of the deleterious effects of the interferon response. Specific targeting of a particular gene function, which is possible with 21-23 nt fragments of the present invention, is useful in functional genomic and therapeutic applications.

In particular, the present invention relates to RNA molecules of about 21 to about 23 nucleotides that mediate RNAi. In one embodiment, the present invention relates to RNA molecules of about 21 to about 23 nucleotides that direct cleavage of specific mRNA to which they correspond. The 21-23 nt RNA molecules of the present invention can also comprise a 3' hydroxyl group. The 21-23 nt RNA molecules can be single-stranded or double stranded (as two 21-23 nt RNAs); such molecules can be blunt ended or comprise overhanging ends (e.g., 5', 3'). In specific embodiments, the RNA molecule is double stranded and either blunt ended or comprises overhanging ends (as two 21-23 nt RNAs).

In one embodiment, at least one strand of the RNA molecule has a 3' overhang from about 1 to about 6 nucleotides (e.g., pyrimidine nucleotides, purine nucleotides) in length. In other embodiments, the 3' overhang is from about 1 to about 5 nucleotides, from about 1 to about 3 nucleotides and from about 2 to about 4 nucleotides in length. In one embodiment the RNA molecule is double stranded, one strand has a 3' overhang and the other strand can be blunt-ended or have an overhang. In the embodiment in which the RNA molecule is double stranded and both strands comprise an overhang, the length of the overhangs may be the same or different for each strand. In a particular embodiment, the RNA of the present invention comprises 21 nucleotide strands which are paired and which have overhangs of from about 1 to about 3, particularly about 2, nucleotides on both 3' ends of the RNA. In order to further enhance the stability of the RNA of the present invention, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

The 21-23 nt RNA molecules of the present invention can be obtained using a number of techniques known to those of skill in the art. For example, the RNA can be chemically synthesized or recombinantly produced using methods known in the art. The 21-23 nt RNAs can also be obtained using the Drosophila in vitro system described herein. Use of the Drosophila in vitro system entails combining dsRNA with a soluble extract derived from Drosophila embryo, thereby producing a combination. The combination is maintained under conditions in which the dsRNA is processed to RNA of about 21 to about 23 nucleotides. The Drosophila in vitro system can also be used to obtain RNA of about 21 to about 23 nucleotides in length which mediates RNA interference of the mRNA of a particular gene (e.g., oncogene, viral gene). In this embodiment, double-stranded RNA that corresponds to a sequence of the gene is combined with a soluble extract derived from Drosophila embryo, thereby producing a combination. The combination is maintained under conditions in which the double-stranded RNA is processed to the RNA of about 21 to about 23 nucleotides. As shown herein, 21-23 nt RNA mediates RNAi of the mRNA to be degraded. The present invention also relates to the 21-23 nt RNA molecules produced by the methods described herein.

In one embodiment, the methods described herein are used to identify or obtain 21-23 nt RNA molecules that are useful as sequence-specific mediators of RNA degradation and, thus, for inhibiting mRNAs, such as human mRNAs, that encode products associated with or causative of a disease or an undesirable condition. For example, production of an oncoprotein or viral protein can be inhibited in humans in order to prevent the disease or condition from occurring, limit the extent to which it occurs or reverse it. If the sequence of the gene to be targeted in humans is known, 21-23 nt RNAs can be produced and tested for their ability to mediate RNAi in a cell, such as a human or other primate cell. Those 21-23 nt human RNA molecules shown to mediate RNAi can be tested, if desired, in an appropriate animal model to further assess their in vivo effectiveness. Additional copies of 21-23 nt RNAs shown to mediate RNAi can be produced by the methods described herein.

The method of obtaining the 21-23 nt RNA sequence using the Drosophila in vitro system can further comprise isolating the RNA sequence from the combination. The 21-23 nt RNA molecules can be isolated using a number of techniques known to those of skill in the art. For example, gel electrophoresis can be used to separate 21-23 nt RNAs from the combination, gel slices comprising the RNA sequences removed and RNAs eluted from the gel slices. Alternatively, non-denaturing methods, such as non-denaturing column chromatography, can be used to isolate the RNA produced. In addition, chromatography (e.g., size exclusion chromatography), glycerol gradient centrifugation, affinity purification with antibody can be used to isolate 21-23 nt RNAs. The RNA-protein complex isolated from the Drosophila in vitro system can also be used directly in the methods described herein (e.g., method of mediating RNAi of mRNA of a gene). Soluble extracts derived from Drosophila embryo that mediate or RNAi are encompassed by the invention. The soluble Drosophila extract can be obtained in a variety of ways. For example, the soluble extract can be obtained from syncytial blastoderm Drosophila embryos as described in Examples 1, 2, and 3. Soluble extracts can be derived from other cells in which RNAi occurs. Alternatively, soluble extracts can be obtained from a cell that does not carry out RNAi. In this instance, the factors needed to mediate RNAi can be introduced into such a cell and the soluble extract is then obtained. The components of the extract can also be chemically synthesized and/or combined using methods known in the art.

Any dsRNA can be used in the methods of the present invention, provided that it has sufficient homology to the targeted gene to mediate RNAi. The sequence of the dsRNA for use in the methods of the present invention need not be known. Alternatively, the dsRNA for use in the present invention can correspond to a known sequence, such as that of an entire gene (one or more) or portion thereof. There is no upper limit on the length of the dsRNA that can be used. For example, the dsRNA can range from about 21 base pairs (bp) of the gene to the full length of the gene or more. In one embodiment, the dsRNA used in the methods of the present invention is about 1000 bp in length. In another embodiment, the dsRNA is about 500 bp in length. In yet another embodiment, the dsRNA is about 22 bp in length.

The 21 to 23 nt RNAs described herein can be used in a variety of ways. For example, the 21 to 23 nt RNA molecules can be used to mediate RNA interference of mRNA of a gene in a cell or organism. In a specific embodiment, the 21 to 23 nt RNA is introduced into human cells or a human in order to mediate RNA interference in the cells or in cells in the individual, such as to prevent or treat a disease or undesirable condition. In this method, a gene (or genes) that cause or contribute to the disease or undesirable condition is targeted and the corresponding mRNA (the transcriptional product of the targeted gene) is degraded by RNAi. In this embodiment, an RNA of about 21 to about 23 nucleotides that targets the corresponding mRNA (the mRNA of the targeted gene) for degradation is introduced into the cell or organism. The cell or organism is maintained under conditions under which degradation of the corresponding mRNA occurs, thereby mediating RNA interference of the mRNA of the gene in the cell or organism. In a particular embodiment, the method of mediating RNA interference of a gene in a cell comprises combining double-stranded RNA that corresponds to a sequence of the gene with a soluble extract derived from *Drosophila* embryo, thereby producing a combination. The combination is maintained under conditions in which the double-stranded RNA is processed to RNA of about 21 to about 23 nucleotides. The 21 to 23 nt RNA is then isolated and introduced into the cell or organism. The cell or organism is maintained under conditions in which degradation of mRNA of the gene occurs, thereby mediating RNA interference of the gene in the cell or organism. In the event that the 21-23 nt RNA is introduced into a cell in which RNAi, does not normally occur, the factors needed to mediate RNAi are introduced into such a cell or the expression of the needed factors is induced in such a cell. Alternatively, 21 to 23 nt RNA produced by other methods (e.g., chemical synthesis, recombinant DNA production) to have a composition the same as or sufficiently similar to a 21 to 23 nt RNA known to mediate RNAi can be similarly used to mediate RNAi. Such 21 to 23 nt RNAs can be altered by addition, deletion, substitution or modification of one or more nucleotides and/or can comprise non-nucleotide materials. A further embodiment of this invention is an ex vivo method of treating cells from an individual to degrade a gene(s) that causes or is associated with a disease or undesirable condition, such as leukemia or AIDS. In this embodiment, cells to be treated are obtained from the individual using known methods (e.g., phlebotomy or collection of bone marrow) and 21-23 nt RNAs that mediate degradation of the corresponding mRNA(s) are introduced into the cells, which are then re-introduced into the individual. If necessary, biochemical components needed for RNAi to occur can also be introduced into the cells.

The mRNA of any gene can be targeted for degradation using the methods of mediating interference of mRNA described herein. For example, any cellular or viral mRNA, can be targeted, and, as a result, the encoded protein (e.g., an oncoprotein, a viral protein), expression will be diminished. In addition, the mRNA of any protein associated with/causative of a disease or undesirable condition can be targeted for degradation using the methods described herein.

The present invention also relates to a method of examining the function of a gene in a cell or organism. In one embodiment, an RNA sequence of about 21 to about 23 nucleotides that targets mRNA of the gene for degradation is introduced into the cell or organism. The cell or organism is maintained under conditions under which degradation of mRNA of the gene occurs. The phenotype of the cell or organism is then observed and compared to an appropriate control, thereby providing information about the function of the gene. In another embodiment, double-stranded RNA that corresponds to a sequence of the gene is combined with a soluble extract derived from *Drosophila* embryo under conditions in which the double-stranded RNA is processed to generate RNA of about 21 to about 23 nucleotides. The RNA of about 21 to about 23 nucleotides is isolated and then introduced into the cell or organism. The cell or organism is maintained under conditions in which degradation of the mRNA of the gene occurs. The phenotype of the cell or organism is then observed and compared to an appropriate control, thereby identifying the function of the gene.

A further aspect of this invention is a method of assessing the ability of 21-23 nt RNAs to mediate RNAi and, particularly, determining which 21-23 nt RNA(s) most efficiently mediate RNAi. In one embodiment of the method, dsRNA corresponding to a sequence of an mRNA to be degraded is combined with detectably labeled (e.g., end-labeled, such as radiolabeled) mRNA and the soluble extract of this invention, thereby producing a combination. The combination is maintained under conditions under which the double-stranded RNA is processed and the mRNA is degraded. The sites of the most effective cleavage are mapped by comparing the migration of the labeled mRNA cleavage products to markers of known length. 21 mers spanning these sites are then designed and tested for their efficiency in mediating RNAi.

Alternatively, the extract of the present invention can be used to determine whether there is a particular segment or particular segments of the mRNA corresponding to a gene which are more efficiently targeted by RNAi than other regions and, thus, can be especially useful target sites. In one embodiment, dsRNA corresponding to a sequence of a gene to be degraded, labeled mRNA of the gene is combined with a soluble extract that mediates RNAi, thereby producing a combination. The resulting combination is maintained under conditions under which the dsRNA is degraded and the sites on the mRNA that are most efficiently cleaved are identified, using known methods, such as comparison to known size standards on a sequencing gel.

OVERVIEW OF EXAMPLES

Biochemical analysis of RNAi has become possible with the development of the in vitro *Drosophila* embryo lysate that recapitulates dsRNA-dependent silencing of gene expression described in Example 1 (Tuschl et al., Genes Dev., 13:3191-7 (1999)). In the in vitro system, dsRNA, but not sense or asRNA, targets a corresponding mRNA for degradation, yet does not affect the stability of an unrelated control mRNA. Furthermore, pre-incubation of the dsRNA in the lysate potentiates its activity for target mRNA degradation, suggesting that the dsRNA must be converted to an active form by binding proteins in the extract or by covalent modification (Tuschl et al., Genes Dev., 13:3191-7 (1999)).

The development of a cell-free system from syncytial blastoderm *Drosophila* embryos that recapitulates many of the features of RNAi is described herein. The interference observed in this reaction is sequence-specific, is promoted by dsRNA, but not by single-stranded RNA, functions by specific mRNA degradation, requires a minimum length of dsRNA and is most efficient with long dsRNA. Furthermore, preincubation of dsRNA potentiates its activity. These results demonstrate that RNAi is mediated by sequence specific processes in soluble reactions.

As described in Example 2, the in vitro system was used to analyze the requirements of RNAi and to determine the fate of the dsRNA and the mRNA. RNAi in vitro requires ATP, but does not require either mRNA translation or recognition of the 7-methyl-guanosine cap of the targeted mRNA. The dsRNA, but not single-stranded RNA, is processed in vitro to a population of 21-23 nt species. Deamination of adenosines within the dsRNA does not appear to be required for formation of the 21-23 nt RNAs. As described herein, the mRNA is cleaved only in the region corresponding to the sequence of the dsRNA and that the mRNA is cleaved at 21-23 nt intervals, strongly indicating that the 21-23 nt fragments from the dsRNA are targeting the cleavage of the mRNA. Furthermore, as described in Examples 3 and 4, when the 21-23 nt fragments are purified and added back to the soluble extract, they mediate RNA.

The present invention is illustrated by the following examples, which are not intended to be limiting in any way.

Example 1

Targeted mRNA Degradation by Double-Stranded RNA In Vitro Materials and Methods

RNAs

Rr-Luc mRNA consisted of the 926 nt Rr luciferase coding sequence flanked by 25 nt of 5' untranslated sequence from the pSP64 plasmid polylinker and 25 nt of 3' untranslated sequence consisting of 19 nt of pSP64 plasmid polylinker sequence followed by a 6 nt Sac I site. Pp-Luc mRNA contained the 1653 nt Pp luciferase coding sequence with a Kpn I site introduced immediately before the Pp luciferase stop codon. The Pp coding sequence was flanked by 5' untranslated sequences consisting of 21 nt of pSP64 plasmid polylinker followed by the 512 nt of the 5' untranslated region (UTR) from the *Drosophila* hunchback mRNA and 3' untranslated sequences consisting of the 562 nt hunchback 3' UTR followed by a 6 nt Sac I site. The hunchback 3' UTR sequences used contained six G-to-U mutations that disrupt function of the Nanos Response Elements in vivo and in vitro. Both reporter mRNAs terminated in a 25 nt poly(A) tail (SEQ ID NO: 20) encoded in the transcribed plasmid. For both Rr-Luc and Pp-Luc mRNAs, the transcripts were generated by run-off transcription from plasmid templates cleaved at an Nsi I site that immediately followed the 25 nt encoded poly (A) tail (SEQ ID NO: 20). To ensure that the transcripts ended with a poly(A) tail, the Nsi I-cleaved transcription templates were resected with T4 DNA Polymerase in the presence of dNTPs. The SP6 mMessage mMachine kit (Ambion) was used for in vitro transcription. Using this kit, about 80% of the resulting transcripts are 7-methyl guanosine capped. $^{32}$P-radiolabeling was accomplished by including $\alpha$-$^{32}$P-UTP in the transcription reaction.

For Pp-Luc, ss, as, and dsRNA corresponded to positions 93 to 597 relative to the start of translation, yielding a 505 bp dsRNA. For Rr-Luc, ss, as, and dsRNA corresponded to positions 118 to 618 relative to the start of translation, yielding a 501 bp dsRNA. The *Drosophila* nanos competitor dsRNA corresponded to positions 122 to 629 relative to the start of translation, yielding a 508 bp dsRNA. ssRNA, asRNA, and dsRNA (diagrammed in FIG. 1) were transcribed in vitro with T7 RNA polymerase from templates generated by the polymerase chain reaction. After gel purification of the T7 RNA transcripts, residual DNA template was removed by treatment with RQ1 DNase (Promega). The RNA was then extracted with phenol and chloroform, and then precipitated and dissolved in water.

RNA Annealing and Native Gel Electrophoresis.

ssRNA and asRNA (0.5 µM) in 10 mM Tris-HCl (pH 7.5) with 20 mM NaCl were heated to 95° C. for 1 min then cooled and annealed at room temperature for 12 to 16 h. The RNAs were precipitated and resuspended in lysis buffer (below). To monitor annealing, RNAs were electrophoresed in a 2% agarose gel in TBE buffer and stained with ethidium bromide (Sambrook et al., Molecular Cloning. Cold Spring Harbor Laboratory Press, Plainview, N.Y. (1989)).

Lysate Preparation

Zero- to two-hour old embryos from Oregon R flies were collected on yeasted molasses agar at 25° C. Embryos were dechorionated for 4 to 5 min in 50% (v/v) bleach, washed with water, blotted dry, and transferred to a chilled Potter-Elvehjem tissue grinder (Kontes). Embryos were lysed at 4° C. in one ml of lysis buffer (100 mM potassium acetate, 30 mM HEPES-KOH, pH 7.4, 2 mM magnesium acetate) containing 5 mM dithiothreitol (DTT) and 1 mg/ml Pefabloc SC (Boehringer-Mannheim) per gram of damp embryos. The lysate was centrifuged for 25 min at 14,500×g at 4° C., and the supernatant flash frozen in aliquots in liquid nitrogen and stored at −80° C.

Reaction Conditions

Lysate preparation and reaction conditions were derived from those described by Hussain and Leibowitz (Hussain and Leibowitz, Gene 46:13-23 (1986)). Reactions contained 50% (v/v) lysate, mRNAs (10 to 50 pM final concentration), and 10% (v/v) lysis buffer containing the ssRNA, asRNA, or dsRNA (10 nM final concentration). Each reaction also contained 10 mM creatine phosphate, 10 µg/ml creatine phosphokinase, 100 µM GTP, 100 µM UTP, 100 µM CTP, 500 µM ATP, 5 µM DTT, 0.1 U/mL RNasin (Promega), and 100 µM of each amino acid. The final concentration of potassium acetate was adjusted to 100 mM. For standard conditions, the reactions were assembled on ice and then pre-incubated at 25° C. for 10 min before adding mRNA. After adding mRNAs, the incubation was continued for an additional 60 min. The 10 min preincubation step was omitted for the experiments in FIGS. 3A-3C and 5A-5C. Reactions were quenched with four volumes of 1.25× Passive Lysis Buffer (Promega). Pp and Rr luciferase activity was detected in a Monolight 2010 Luminometer (Analytical Luminescence Laboratory) using the Dual-Luciferase Reporter Assay System (Promega).

RNA Stability

Reactions with $^{32}$P-radiolabeled mRNA were quenched by the addition of 40 volumes of 2×PK buffer (200 mM Tris-HCl, pH 7.5, 25 mM EDTA, 300 mM NaCl, 2% w/v sodium dodecyl sulfate). Proteinase K (E.M. Merck; dissolved in water) was added to a final concentration of 465 µg/ml. The reactions were then incubated for 15 min at 65° C., extracted with phenol/chloroform/isoamyl alcohol (25:24:1), and precipitated with an equal volume of isopropanol. Reactions were analyzed by electrophoresis in a formaldehyde/agarose (0.8% w/v) gel (Sambrook et al., Molecular Cloning. Cold Spring Harbor Laboratory Press, Plainview, N.Y. (1989)). Radioactivity was detected by exposing the agarose gel [dried under vacuum onto Nytran Plus membrane (Amersham)] to an image plate (Fujix) and quantified using a Fujix Bas 2000 and Image Gauge 3.0 (Fujix) software.

Commercial Lysates

Untreated rabbit reticulocyte lysate (Ambion) and wheat germ extract (Ambion) reactions were assembled according to the manufacturer's directions. dsRNA was incubated in the lysate at 27° C. (wheat germ) or 30° C. (reticulocyte lysate) for 10 min prior to the addition of mRNAs.

Results and Discussion

To evaluate if dsRNA could specifically block gene expression in vitro, reporter mRNAs derived from two different luciferase genes that are unrelated both in sequence and in luciferin substrate specificity were used: *Renilla reniformis* (sea pansy) luciferase (Rr-Luc) and *Photuris pennsylvanica* (firefly) luciferase (Pp-Luc). dsRNA generated from one gene was used to target that luciferase mRNA whereas the other luciferase mRNA was an internal control co-translated in the same reaction. dsRNAs of approximately 500 bp were prepared by transcription of polymerase-chain reaction products from the Rr-Luc and Pp-Luc genes. Each dsRNA began ~100 bp downstream of the start of translation (FIG. 1). Sense (ss) and anti-sense (as) RNA were transcribed in vitro and annealed to each other to produce the dsRNA. Native gel electrophoresis of the individual Rr 501 and Pp 505 nt as RNA and ssRNA used to form the Rr and Pp dsRNAs was preformed. The ssRNA, asRNA, and dsRNAs were each tested for their ability to block specifically expression of their cognate mRNA but not the expression of the unrelated internal control mRNA.

The ssRNA, asRNA, or dsRNA was incubated for 10 min in a reaction containing *Drosophila* embryo lysate, then both Pp-Luc and Rr-Luc mRNAs were added and the incubation continued for an additional 60 min. The *Drosophila* embryo lysate efficiently translates exogenously transcribed mRNA under the conditions used. The amounts of Pp-Luc and Rr-Luc enzyme activities were measured and were used to calculate ratios of either Pp-Luc/Rr-Luc (FIG. 2A) or Rr-Luc/Pp-Luc (FIG. 2B). To facilitate comparison of different experiments, the ratios from each experiment were normalized to the ratio observed for a control in which buffer was added to the reaction in place of ssRNA, asRNA, or dsRNA.

Figure 2A:
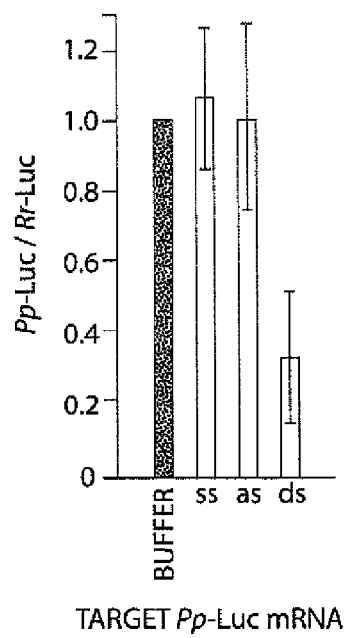
FIG. 2A is a graph of the ratio of luciferase activities after targeting 50 pM Pp-Luc mRNA with 10 nM ssRNA, asRNA, or dsRNA from the 505 bp segment of the Pp-Luc gene showing gene-specific interference by dsRNA in vitro. The data are the average values of seven trials±standard deviation. Four independently prepared lysates were used. Luciferase activity was normalized to the buffer control; a ratio equal to one indicates no gene-specific interference.
Figure 2B:
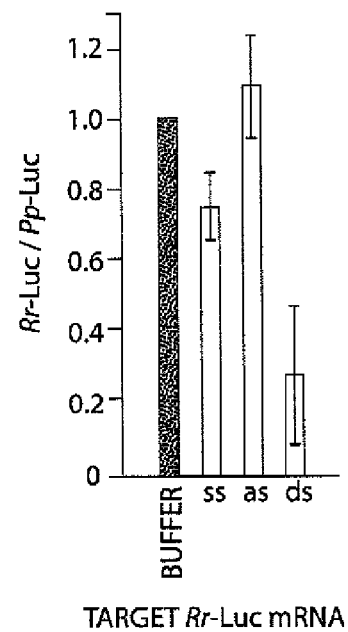
FIG. 2B is a graph of the ratio of luciferase activities after targeting 50 pM Rr-Luc mRNA with 10 nM ssRNA, asRNA, or dsRNA from the 501 bp segment of the Rr-Luc gene showing gene-specific interference by dsRNA in vitro. The data are the average values of six trials±standard deviation. A Rr-Luc/Pp-Luc ratio equal to one indicates no gene-specific interference.

FIG. 2A shows that a 10 nM concentration of the 505 bp dsRNA identical to a portion of the sequence of the Pp-Luc gene specifically inhibited expression of the Pp-Luc mRNA but did not affect expression of the Rr-Luc internal control. Neither ssRNA nor asRNA affected expression of Pp-Luc or the Rr-Luc internal control. Thus, Pp-Luc expression was specifically inhibited by its cognate dsRNA. Conversely, a 10 nM concentration of the 501 bp dsRNA directed against the Rr-Luc mRNA specifically inhibited Rr-Luc expression but not that of the Pp-Luc internal control (FIG. 2B). Again, comparable levels of ssRNA or asRNA had little or no effect on expression of either reporter mRNA. On average, dsRNA reduced specific luciferase expression by 70% in these experiments, in which luciferase activity was measured after 1 h incubation. In other experiments in which the translational capacity of the reaction was replenished by the addition of fresh lysate and reaction components, a further reduction in targeted luciferase activity relative to the internal control was observed.

The ability of dsRNA but not asRNA to inhibit gene expression in these lysates is not merely a consequence of the greater stability of the dsRNA (half-life about 2 h) relative to the single-stranded RNAs (half-life ~10 min). ssRNA and asRNA transcribed with a 7-methyl guanosine cap were as stable in the lysate as uncapped dsRNA, but do not inhibit gene expression. In contrast, dsRNA formed from the capped ssRNA and asRNA specifically blocks expression of the targeted mRNA.

Figure 3A:
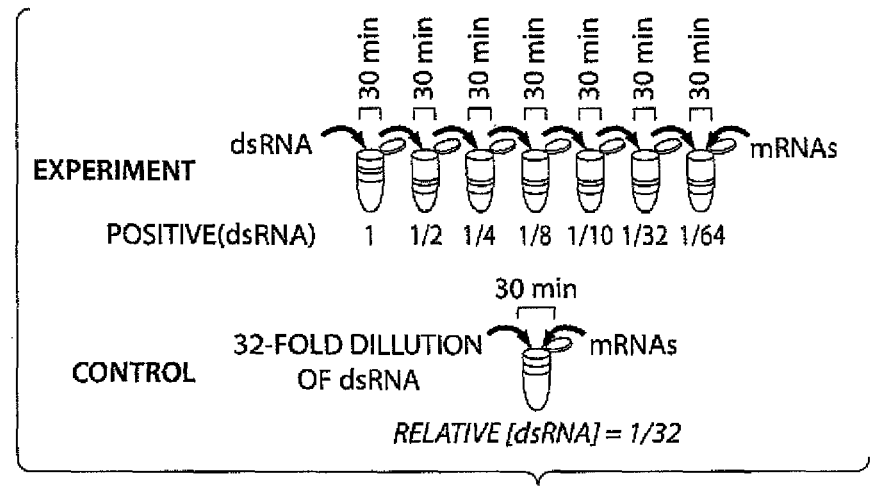
FIG. 3A is a schematic representation of the experimental strategy used to show that incubation in the *Drosophila* embryo lysate potentiates dsRNA for gene-specific interference. The same dsRNAs used in FIG. 2 (or buffer) was serially preincubated using two-fold dilutions in six successive reactions with *Drosophila* embryo lysate, then tested for its capacity to block mRNA expression. As a control, the same amount of dsRNA (10 nM) or buffer was diluted directly in buffer and incubated with Pp-Luc and Rr-Luc mRNAs and lysate.
Figure 3B:
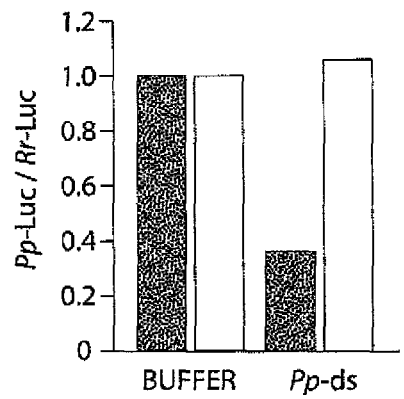
FIG. 3B is a graph of potentiation when targeting Pp-Luc mRNA. Black columns indicate the dsRNA or the buffer was serially preincubated; white columns correspond to a direct 32-fold dilution of the dsRNA. Values were normalized to those of the buffer controls.

Effective RNAi in *Drosophila* requires the injection of about 0.2 fmol of dsRNA into a syncytial blastoderm embryo (Kennerdell and Carthew, Cell 95:1017-1026 (1998); Carthew, www1.pitted.edu/~carthew/manual/RN-Ai_Protocol.html (1999)). Since the average volume of a *Drosophila* embryo is approximately 7.3 nl, this corresponds to an intracellular concentration of about 25 nM (Mazur et al., Cryobiology 25:543-544 (1988)). Gene expression in the *Drosophila* lysate was inhibited by a comparable concentration of dsRNA (10 nM), but lowering the dsRNA concentration ten-fold decreased the amount of specific interference. Ten nanomolar dsRNA corresponds to a 200-fold excess of dsRNA over target mRNA added to the lysate. To test if this excess of dsRNA might reflect a time- and/or concentration-dependent step in which the input dsRNA was converted to a form active for gene-specific interference, the effect of preincubation of the dsRNA on its ability to inhibit expression of its cognate mRNA was examined. Because the translational capacity of the lysates is significantly reduced after 30 min of incubation at 25° C. (unpublished observations), it was desired to ensure that all factors necessary for RNAi remained active throughout the pre-incubation period. Therefore, every 30 min, a reaction containing dsRNA and lysate was mixed with a fresh reaction containing unincubated lysate (FIG. 3A). After six successive serial transfers spanning 3 hours of preincubation, the dsRNA, now diluted 64-fold relative to its original concentration, was incubated with lysate and 50 pM of target mRNA for 60 min. Finally, the Pp-Luc and Rr-Luc enzyme levels were measured. For comparison, the input amount of dsRNA (10 nM) was diluted 32-fold in buffer, and its capacity to generate gene-specific dsRNA interference in the absence of any preincubation step was assessed.

Figure 3C:
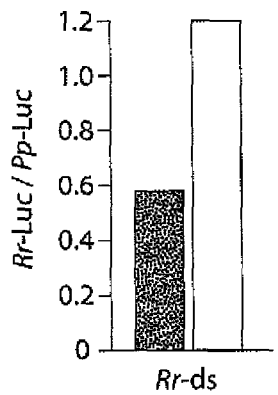
FIG. 3C is a graph of potentiation when targeting Rr-Luc mRNA. The corresponding buffer control is shown in FIG. 3B.

The preincubation of the dsRNA in lysate significantly potentiated its capacity to inhibit specific gene expression. Whereas the dsRNA diluted 32-fold showed no effect, the preincubated dsRNA was, within experimental error, as potent as undiluted dsRNA, despite having undergone a 64-fold dilution. Potentiation of the dsRNA by preincubation was observed for dsRNAs targeting both the Pp-Luc mRNA (FIG. 3B) and the Rr-Luc mRNA (FIG. 3C). Taking into account the 64-fold dilution, the activation conferred by pre-incubation allowed a 156 pM concentration of dsRNA to inhibit 50 pM target mRNA. Further, dilution of the "activated" dsRNA may be effective but has not been tested. We note that although both dsRNAs tested were activated by the preincubation procedure, each fully retained its specificity to interfere with expression only of the mRNA to which it is homologous. Further study of the reactions may provide a route to identifying the mechanism of dsRNA potentiation.

Figure 4:
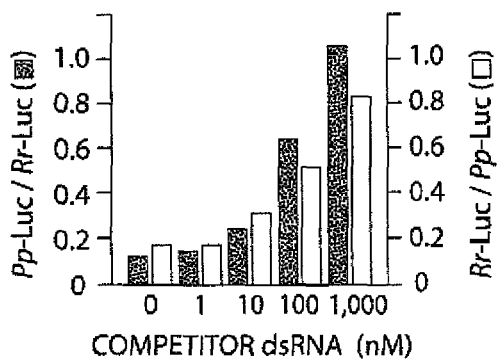
FIG. 4 is a graph showing effect of competitor dsRNA on gene-specific interference. Increasing concentrations of nanos dsRNA (508 bp) were added to reactions containing 5 nM dsRNA (the same dsRNAs used in FIGS. 2A and 2B) targeting Pp-Luc mRNA (black columns, left axis) or Rr-Luc mRNA (white columns, right axis). Each reaction contained both a target mRNA (Pp-Luc for the black columns, Rr-Luc for the white) and an unrelated control mRNA (Rr-Luc for the black columns, Pp-Luc for the white). Values were normalized to the buffer control (not shown). The reactions were incubated under standard conditions (see Methods).

One possible explanation for the observation that preincubation of the dsRNA enhances its capacity to inhibit gene expression in these lysates is that specific factors either modify and/or associate with the dsRNA. Accordingly, the addition of increasing amounts of dsRNA to the reaction might titrate such factors and decrease the amount of gene-specific interference caused by a second dsRNA of unrelated sequence. For both Pp-Luc mRNA and Rr-Luc mRNA, addition of increasing concentrations of the unrelated *Drosophila* nanos dsRNA to the reaction decreased the amount of gene-specific interference caused by dsRNA targeting the reporter mRNA (FIG. 4). None of the tested concentrations of nanos dsRNA affected the levels of translation of the untargeted mRNA, demonstrating that the nanos dsRNA specifically titrated factors involved in gene-specific interference and not components of the translational machinery. The limiting factor(s) was titrated by addition of approximately 1000 nM dsRNA, a 200-fold excess over the 5 nM of dsRNA used to produce specific interference.

Figure 5A:
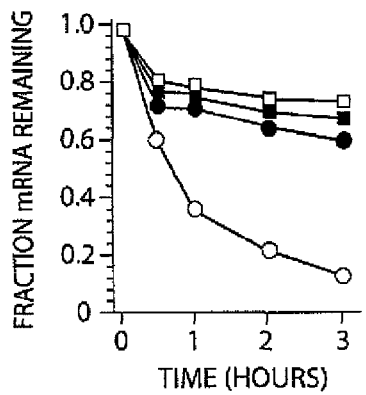
FIG. 5A is a graph showing the effect of dsRNA on mRNA stability. Circles, Pp-Luc mRNA; squares, Rr-Luc mRNA; filled symbols, buffer incubation; open symbols, incubation with Pp-dsRNA.
Figure 5B:
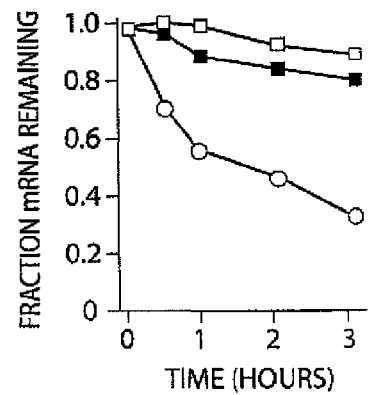
FIG. 5B is a graph showing the stability of Rr-Luc mRNA incubated with Rr-dsRNA or Pp-dsRNA. Filled squares, buffer; open squares, Pp-dsRNA (10 nM); open circles, Rr-dsRNA (10 nM).
Figure 5C:
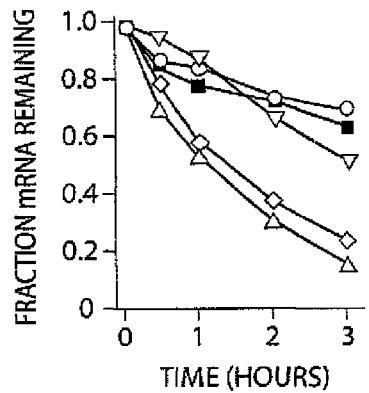
FIG. 5C is a graph showing the dependence on dsRNA length. The stability of the Pp-Luc mRNA was assessed after incubation in lysate in the presence of buffer or dsRNAs of different lengths. Filled squares, buffer; open circles, 49 bp dsRNA (10 nM); open inverted triangles, 149 bp dsRNA (10 nM); open triangles, 505 bp dsRNA (10 nM); open diamonds, 997 bp dsRNA (10 nM). Reactions were incubated under standard conditions (see Methods).

Interference in vitro might reflect either a specific inhibition of mRNA translation or the targeted destruction of the specific mRNA. To distinguish these two possibilities, the fates of the Pp-Luc and Rr-Luc mRNAs were examined directly using $^{32}$P-radiolabeled substrates. Stability of 10 nM Pp-Luc mRNA or Rr-Luc mRNA incubated in lysate with either buffer or 505 bp Pp-dsRNA (10 nM). Samples were deproteinized after the indicated times and the $^{32}$P-radiolabeled mRNAs were then resolved by denaturing gel electrophoresis. In the absence of dsRNA, both the Pp-Luc and Rr-Luc mRNAs were stable in the lysates, with ~75% of the input mRNA remaining after 3 h of incubation. (About 25% of the input mRNA is rapidly degraded in the reaction and likely represents uncapped mRNA generated by the in vitro transcription process.) In the presence of dsRNA (10 nM, 505 bp) targeting the Pp-Luc mRNA, less than 15% of the Pp-Luc mRNA remained after 3 h (FIG. 5A). As expected, the Rr-Luc mRNA remained stable in the presence of the dsRNA targeting Pp-Luc mRNA. Conversely, dsRNA (10 nM, 501 bp) targeting the Rr-Luc mRNA caused the destruction of the Rr-Luc mRNA but had no effect on the stability of Pp-Luc mRNA (FIG. 5B). Thus, the dsRNA specifically caused accelerated decay of the mRNA to which it is homologous with no effect on the stability of the unrelated control mRNA. This finding indicates that in vivo, at least in *Drosophila*, the effect of dsRNA is to directly destabilize the target mRNA, not to change the subcellular localization of the mRNA, for example, by causing it to be specifically retained in the nucleus, resulting in non-specific degradation.

These results are consistent with the observation that RNAi leads to reduced cytoplasmic mRNA levels in vivo, as measured by in situ hybridization (Montgomery et al., Proc. Natl. Acad. Sci. USA 95:15502-15507 (1998)) and Northern blotting (Ngo et al., Proc. Natl. Acad. Sci. USA 95:14687-14692 (1998)). Northern blot analyses in trypanosomes and hydra suggest that dsRNA typically decreases mRNA levels by less than 90% (Ngo et al., Proc. Natl. Acad. Sci. USA 95:14687-14692 (1998); Lohmann et al., Dev. Biol. 214:211-214 (1999)). The data presented here show that in vitro mRNA levels are reduced 65 to 85% after three hours incubation, an effect comparable with observations in vivo. They also agree with the finding that RNAi in *C. elegans* is post-transcriptional (Montgomery et al., Proc. Natl. Acad. Sci. USA 95:15502-15507 (1998)). The simplest explanation for the specific effects on protein synthesis is that it reflects the accelerated rate of RNA decay. However, the results do not exclude independent but specific effects on translation as well as stability.

In vivo, RNAi appears to require a minimum length of dsRNA (Ngo et al., Proc. Natl. Acad. Sci., USA, 95:14687-14692 (1998)). The ability of RNA duplexes of lengths 49 bp, 149 bp, 505 bp, and 997 bp (diagrammed in FIG. 1) to target the degradation of the Pp-Luc mRNA in vitro was assessed. In good agreement with in vivo observations, the 49 bp dsRNA was ineffective in vitro, while the 149 bp dsRNA enhanced mRNA decay only slightly, and both the 505 and 997 bp dsRNAs caused robust mRNA degradation (FIG. 5C). 50 bp dsRNA targeting other portions of the mRNA cause detectable mRNA degradation, though not as robust as that seen for 500 bp dsRNA. Thus, although some short dsRNA do not mediate RNAi, others of approximately the same length, but different composition, will be able to do so.

Whether the gene-specific interference observed in *Drosophila* lysates was a general property of cell-free translation systems was examined. The effects of dsRNAs on expression of Pp-Luc and Rr-Luc mRNA were examined in commercially available wheat germ extracts and rabbit reticulocyte lysates. There was no effect of addition of 10 nM of either ssRNA, asRNA, or dsRNA on the expression of either mRNA reporter in wheat germ extracts. In contrast, the addition of 10 nM of dsRNA to the rabbit reticulocyte lysate caused a profound and rapid, non-specific decrease in mRNA stability. For example, addition of Rr-Luc dsRNA caused degradation of both Rr-Luc and Pp-Luc mRNAs within 15 min. The same non-specific effect was observed upon addition of Pp-Luc dsRNA. The non-specific destruction of mRNA induced by the addition of dsRNA to the rabbit reticulocyte lysate presumably reflects the previously observed activation of RNase L by dsRNA (Clemens and Williams, Cell 13:565-572 (1978); Williams et al., Nucleic Acids Res. 6:1335-1350 (1979); Zhou et al., Cell 72:753-765 (1993); Matthews, Interactions between Viruses and the Cellular Machinery for Protein Synthesis. In Translational Control (eds. J. Hershey, M. Mathews and N. Sonenberg), pp. 505-548. Cold Spring Harbor Laboratory Press, Plainview, N.Y. (1996)). Mouse cell lines lacking dsRNA-induced anti-viral pathways have recently been described (Zhou et al., Virology 258:435-440 (1999)) and may be useful in the search for mammalian RNAi. Although RNAi is known to exist in some mammalian cells (Wianny and Zernicka-Goetz Nat. Cell Biol. 2: 70-75 (2000)), in many mammalian cell types its presence is likely obscured by the rapid induction by dsRNA of non-specific anti-viral responses.

dsRNA-targeted destruction of specific mRNA is characteristic of RNAi, which has been observed in vivo in many organisms, including *Drosophila*. The system described above recapitulates in a reaction in vitro many aspects of RNAi. The targeted mRNA is specifically degraded whereas unrelated control mRNAs present in the same solution are not affected. The process is most efficient with dsRNAs greater than 150 bp in length. The dsRNA-specific degradation reaction in vitro is probably general to many, if not all, mRNAs since it was observed using two unrelated genes.

The magnitude of the effects on mRNA stability in vitro described herein are comparable with those reported in vivo (Ngo et al., Proc. Natl. Acad. Sci., USA, 95:14687-14692 (1998); Lohmann et al., Dev. Biol., 214:211-214 (1999). However, the reaction in vitro requires an excess of dsRNA relative to mRNA. In contrast, a few molecules of dsRNA per cell can inhibit gene expression in vivo (Fire et al., Nature, 391: 806-811 (1998); Kennerdell and Carthew, Cell, 95:1017-1026 (1998)). The difference between the stoichiometry of dsRNA to target mRNA in vivo and in vitro should not be surprising in that most in vitro reactions are less efficient than their corresponding in vivo processes. Interestingly, incubation of the dsRNA in the lysate greatly potentiated its activity for RNAi, indicating that it is either modified or becomes associated with other factors or both. Perhaps a small number of molecules is effective in inhibiting the targeted mRNA in vivo because the injected dsRNA has been activated by a process similar to that reported here for RNAi in *Drosophila* lysates.

Example 2

Double-Stranded RNA Directs the ATP-Dependent Cleavage of mRNA at 21 to 23

Nucleotide Intervals
Methods and Material
In vitro RNAi

In vitro RNAi reactions and lysate preparation were as described in Example 1 (Tuschl et al., Genes Dev., 13:3191-7 (1999)) except that the reaction contained 0.03 g/ml creatine kinase, 25 µM creatine phosphate (Fluka), and 1 mM ATP. Creatine phosphate was freshly dissolved at 500 mM in water for each experiment. GTP was omitted from the reactions, except in FIGS. 2 and 3.

RNA Synthesis.

Pp-luc and Rr-luc mRNAs and Pp- and Rr-dsRNAs (including dsRNA 'B' in FIG. 6) were synthesized by in vitro transcription as described previously (Tuschl et al., Genes Dev., 13:3191-7 (1999)). To generate transcription templates for dsRNA 'C' the 5' sense RNA primer was gcgtaatacgactcactataGAACAAAGGAAACGGATGAT (SEQ ID NO: 2) and the 3' sense RNA primer was GAAGAAGTTATTCTCCAAAA (SEQ ID NO: 3); the 5' asRNA primer was gcgtaatacgactcactataGAAGAAGTTATTCTCCAAAA (SEQ ID NO: 4) and the 3' asRNA primer was GAACAAAGGAAACGGATGAT (SEQ ID NO: 5). For dsRNA 'A' the 5' sense RNA primer was gcgtaatacgactcactataGTAGCGCGGTGTATTATACC (SEQ ID NO: 6) and the 3' sense RNA primer was GTACAACGTCAGGTTTACCA (SEQ ID NO: 7); the 5' asRNA primer was gcgtaatacgactcactataGTACAACGTCAGGTTTACCA (SEQ ID NO: 8) and the 3' asRNA primer was GTAGCGCGGTGTATTATACC (SEQ ID NO: 9) (lowercase, T7 promoter sequence).

mRNAs were 5'-end-labeled using guanylyl transferase (Gibco/BRL), S-adenosyl methionine (Sigma), and $\alpha$-$^{32}$P-GTP (3000 Ci/mmol; New England Nuclear) according to the manufacturer's directions. Radiolabeled RNAs were purified by poly(A) selection using the Poly(A) Tract III kit (Promega). Nonradioactive 7-methyl-guanosine- and adenosine-capped RNAs were synthesized in in vitro transcription reactions with a 5-fold excess of 7-methyl-G(5')ppp (5')G or A(5')ppp(5')G relative to GTP. Cap analogs were purchased from New England Biolabs.

ATP Depletion and Protein Synthesis Inhibition

ATP was depleted by incubating the lysate for 10 minutes at 25° C. with 2 mM glucose and 0.1 U/ml hexokinase (Sigma). Protein synthesis inhibitors were purchased from Sigma and dissolved in absolute ethanol as 250-fold concentrated stocks. The final concentrations of inhibitors in the reaction were: anisomycin, 53 mg/ml; cycloheximide, 100 mg/ml; chloramphenicol, 100 mg/ml. Relative protein synthesis was determined by measuring the activity of Rr luciferase protein produced by translation of the Rr-luc mRNA in the RNAi reaction after 1 hour as described previously (Tuschl et al., Genes Dev., 13:3191-7 (1999)).

Analysis of dsRNA Processing

Internally $\alpha$-$^{32}$P-ATP-labeled dsRNAs (505 bp Pp-luc or 501 Rr-luc) or 7-methyl-guanosine-capped Rr-luc antisense RNA (501 nt) were incubated at 5 nM final concentration in the presence or absence of unlabeled mRNAs in Drosophila lysate for 2 hours in standard conditions. Reactions were stopped by the addition of 2× proteinase K buffer and deproteinized as described previously (Tuschl et al., Genes Dev., 13:3191-3197 (1999)). Products were analyzed by electrophoresis in 15% or 18% polyacrylamide sequencing gels. Length standards were generated by complete RNase Ti digestion of $\alpha$-$^{32}$P-ATP-labeled 501 nt Rr-luc sense RNA and asRNA.

For analysis of mRNA cleavage, 5'-$^{32}$P-radiolabeled mRNA (described above) was incubated with dsRNA as described previously (Tuschl et al., Genes Dev., 13:3191-3197 (1999)) and analyzed by electrophoresis in 5% (FIG. 5B) and 6% (FIG. 6C) polyacrylamide sequencing gels. Length standards included commercially available RNA size standards (FMC Bioproducts) radiolabeled with guanylyl transferase as described above and partial base hydrolysis and RNase Ti ladders generated from the 5'-radiolabeled mRNA.

Deamination Assay

Internally $\alpha$-$^{32}$P-ATP-labeled dsRNAs (5 nM) were incubated in Drosophila lysate for 2 hours at standard conditions. After deproteinization, samples were run on 12% sequencing gels to separate full-length dsRNAs from the 21-23 nt products. RNAs were eluted from the gel slices in 0.3 M NaCl overnight, ethanol-precipitated, collected by centrifugation, and redissolved in 20 µA water. The RNA was hydrolyzed into nucleoside 5-phosphates with nuclease P1 (10 µl reaction containing 8 µl RNA in water, 30 mM KOAc pH 5.3, 10 mM $ZnSO_4$, 10 µg or 3 units nuclease P1, 3 hours, 50° C.). Samples (1 ml) were co-spotted with non-radioactive 5-mononucleotides [0.05 O.D. units ($A_{260}$) of pA, pC, pG, pI, and pU] on cellulose HPTLC plates (EM Merck) and separated in the first dimension in isobutyric acid/25% ammonia/water (66/1/33, v/v/v) and in the second dimension in 0.1M sodium phosphate, pH 6.8/ammonium sulfate/1-propanol (100/60/2, v/w/v; Silberklang et al., 1979). Migration of the non-radioactive internal standards was determined by UV-shadowing.

Results and Discussion

RNAi Requires ATP

Figure 6:
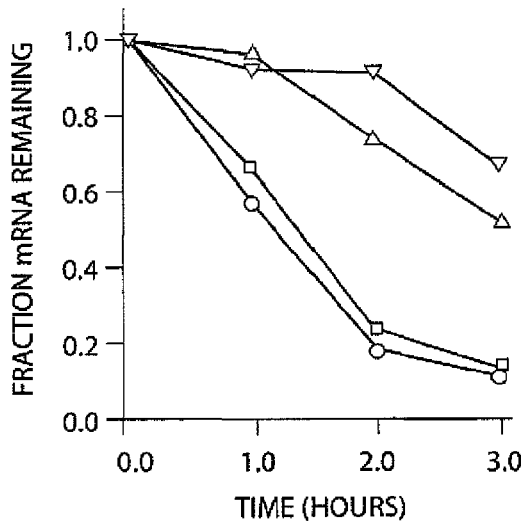
FIG. 6 is a graph showing that RNAi Requires ATP. Creatine kinase (CK) uses creatine phosphate (CP) to regenerate ATP. Circles, +ATP, +CP, +CK; squares, −ATP, +CP, +CK; triangles, −ATP, −CP, +CK; inverted triangles, −ATP, +CP, −CK.

As described in Example 1, Drosophila embryo lysates faithfully recapitulate RNAi (Tuschl et al., Genes Dev., 13:3191-7 (1999)). Previously, dsRNA-mediated gene silencing was monitored by measuring the synthesis of luciferase protein from the targeted mRNA. Thus, these RNAi reactions contained an ATP-regenerating system, needed for the efficient translation of the mRNA. To test if ATP was, in fact, required for RNAi, the lysates were depleted for ATP by treatment with hexokinase and glucose, which converts ATP to ADP, and RNAi was monitored directly by following the fate of $^{32}$P-radiolabeled Renilla reniformis luciferase (Rr-luc) mRNA (FIG. 6). Treatment with hexokinase and glucose reduced the endogenous ATP level in the lysate from 250 µM to below 10 µM. ATP regeneration required both exogenous creatine phosphate and creatine kinase, which acts to transfer a high-energy phosphate from creatine phosphate to ADP. When ATP-depleted extracts were supplemented with either creatine phosphate or creatine kinase separately, no RNAi was observed. Therefore, RNAi requires ATP in vitro. When ATP, creatine phosphate, and creatine kinase were all added together to reactions containing the ATP-depleted lysate, dsRNA-dependent degradation of the Rr-luc mRNA was restored (FIG. 6). The addition of exogenous ATP was not required for efficient RNAi in the depleted lysate, provided that both creatine phosphate and creatine kinase were present, demonstrating that the endogenous concentration (250 mM) of adenosine nucleotide is sufficient to support RNAi. RNAi with a Photinus pyralis luciferase (Pp-luc) mRNA was also ATP-dependent.

The stability of the Rr-luc mRNA in the absence of Rr-dsRNA was reduced in ATP-depleted lysates relative to that observed when the energy regenerating system was included, but decay of the mRNA under these conditions did not display the rapid decay kinetics characteristic of RNAi in vitro, nor did it generate the stable mRNA cleavage products characteristic of dsRNA-directed RNAi. These experiments do not establish if the ATP requirement for RNAi is direct, implicating ATP in one or more steps in the RNAi mechanism, or indirect, reflecting a role for ATP in maintaining high concentrations of another nucleoside triphosphate in the lysate.

Translation is not Required for RNAi In Vitro

Figure 7A:
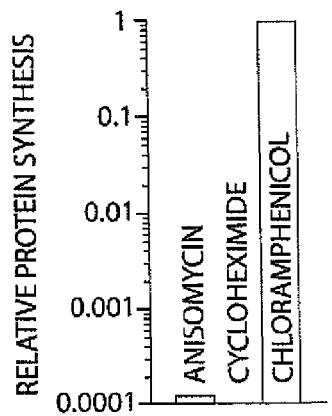
FIG. 7A is a graph of protein synthesis, as reflected by luciferase activity produced after incubation of Rr-luc mRNA in the in vitro RNAi reaction for 1 hour, in the presence of the protein synthesis inhibitors anisomycin, cycloheximide, or chloramphenicol, relative to a reaction without any inhibitor showing that RNAi does not require mRNA translation.

The requirement for ATP suggested that RNAi might be coupled to mRNA translation, a highly energy-dependent process. To test this possibility, various inhibitors of protein synthesis were added to the reaction by preparing a denaturing agarose-gel analysis of 5'-32P-radiolabeled Pp-luc mRNA after incubation for indicated times in a standard RNAi reaction with and without protein synthesis inhibitors. The eukaryotic translation inhibitors anisomycin, an inhibitor of initial peptide bond formation, cycloheximide, an inhibitor of peptide chain elongation, and puromycin, a tRNA mimic which causes premature termination of translation (Cundliffe, Antibiotic Inhibitors of Ribosome Function. In The Molecular Basis of Antibiotic Action, E. Gale, E. Cundliffe, P. Reynolds, M. Richmond and M. Warning, eds. (New York: Wiley), pp. 402-547. (1981)) were tested. Each of these inhibitors reduced protein synthesis in the *Drosophila* lysate by more than 1,900-fold (FIG. 7A). In contrast, chloramphenicol, an inhibitor of *Drosophila* mitochondrial protein synthesis (Page and Orr-Weaver, Dev. Biol., 183:195-207 (1997)), had no effect on translation in the lysates (FIG. 7A). Despite the presence of anisomycin, cycloheximide, or chloramphenicol, RNAi proceeded at normal efficiency. Puromycin also did not perturb efficient RNAi. Thus, protein synthesis is not required for RNAi in vitro.

Figure 7B:
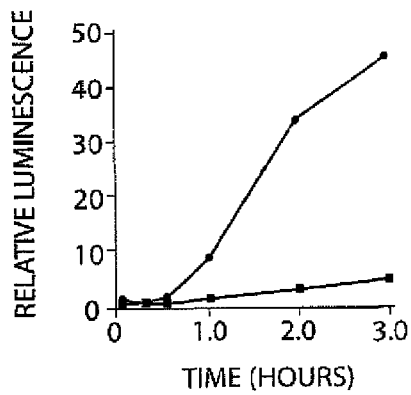
FIG. 7B is a graph showing translation of 7-methyl-guanosine- and adenosine-capped Pp-luc mRNAs (circles and squares, respectively) in the RNAi reaction in the absence of dsRNA, as measured by luciferase activity produced in a one-hour incubation.
Figure 7C:
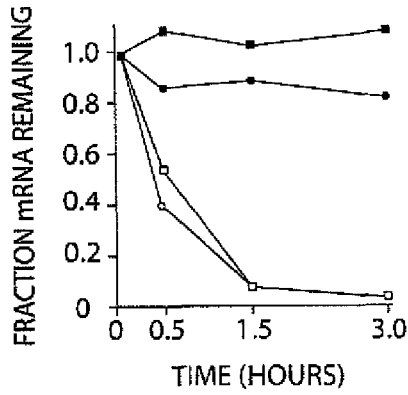
FIG. 7C is a graph showing incubation in an RNAi reaction of uniformly $^{32}$P-radiolabeled 7-methyl-guanosine-capped Pp-luc mRNA (circles) and adenosine-capped Pp-luc mRNA (squares), in the presence (open symbols) and absence (filled symbols) of 505 bp Pp-luc dsRNA.

Translational initiation is an ATP-dependent process that involves recognition of the 7-methyl guanosine cap of the mRNA (Kozak, Gene, 234:187-208 (1999); Merrick and Hershey, The Pathway and Mechanism of Eukaryotic Protein Synthesis. In Translational Control, J. Hershey, M. Mathews and N. Sonenberg, eds. (Cold Spring Harbor, N.Y.: Cold Spring Harbor Laboratory Press), pp. 31-69 (1996)). The *Drosophila* lysate used to support RNAi in vitro also recapitulates the cap-dependence of translation; Pp-luc mRNA with a 7-methyl-guanosine cap was translated greater than ten-fold more efficiently than was the same mRNA with an A(5')ppp(5')G cap (FIG. 7B). Both RNAs were equally stable in the *Drosophila* lysate, showing that this difference in efficiency cannot be merely explained by more rapid decay of the mRNA with an adenosine cap (see also Gebauer et al., EMBO J., 18:6146-54 (1999)). Although the translational machinery can discriminate between Pp-luc mRNAs with 7-methyl-guanosine and adenosine caps, the two mRNAs were equally susceptible to RNAi in the presence of Pp-dsRNA (FIG. 7C). These results suggest that steps in cap recognition are not involved in RNAi.

dsRNA is Processed to 21-23 nt Species

RNAs 25 nt in length are generated from both the sense and anti-sense strands of genes undergoing post-transcriptional gene silencing in plants (Hamilton and Baulcombe, Science, 286:950-2 (1999)). Denaturing acrylamide-gel analysis of the products formed in a two-hour incubation of uniformly $^{32}$P-radiolabeled dsRNAs and capped asRNA in lysate under standard RNAi conditions, in the presence or absence of target mRNAs. It was found that dsRNA is also processed to small RNA fragments. When incubated in lysate, approximately 15% of the input radioactivity of both the 501 bp Rr-dsRNA and the 505 bp Pp-dsRNA appeared in 21 to 23 nt RNA fragments. Because the dsRNAs are more than 500 bp in length, the 15% yield of fragments implies that multiple 21-23 nt RNAs are produced from each full-length dsRNA molecule. No other stable products were detected. The small RNA species were produced from dsRNAs in which both strands were uniformly $^{32}$P-radiolabeled. Formation of the 21-23 nt RNAs from the dsRNA did not require the presence of the corresponding mRNA, demonstrating that the small RNA species is generated by processing of the dsRNA, rather than as a product of dsRNA-targeted mRNA degradation. It was noted that 22 nucleotides corresponds to two turns of an A-form RNA-RNA helix.

When dsRNAs radiolabeled within either the sense or the anti-sense strand were incubated with lysate in a standard RNAi reaction, 21-23 nt RNAs were generated with comparable efficiency. These data support the idea that the 21-23 nt RNAs are generated by symmetric processing of the dsRNA. A variety of data support the idea that the 21-23 nt RNA is efficiently generated only from dsRNA and is not the consequence of an interaction between single-stranded RNA and the dsRNA. First, a $^{32}$P-radiolabeled 505 nt Pp-luc sense RNA or asRNA was not efficiently converted to the 21-23 nt product when it was incubated with 5 nM nonradioactive 505 bp Pp-dsRNA. Second, in the absence of mRNA, a 501 nt 7-methyl-guanosine-capped Rr-asRNA produced only a barely detectable amount of 21-23 nt RNA (capped single-stranded RNAs are as stable in the lysate as dsRNA, Tuschl et al., Genes Dev., 13:3191-7(1999)), probably due to a small amount of dsRNA contaminating the anti-sense preparation. However, when Rr-luc mRNA was included in the reaction with the $^{32}$P-radiolabeled, capped Rr-asRNA, a small amount of 21-23 nt product was generated, corresponding to 4% of the amount of 21-23 nt RNA produced from an equimolar amount of Rr-dsRNA. This result is unlikely to reflect the presence of contaminating dsRNA in the Rr-asRNA preparation, since significantly more product was generated from the asRNA in the presence of the Rr-luc mRNA than in the absence. Instead, the data suggest that asRNA can interact with the complementary mRNA sequences to form dsRNA in the reaction and that the resulting dsRNA is subsequently processed to the small RNA species. Rr-asRNA can support a low level of bona fide RNAi in vitro (see below), consistent with this explanation.

It was next asked if production of the 21-23 nt RNAs from dsRNA required ATP. When the 505 bp Pp-dsRNA was incubated in a lysate depleted for ATP by treatment with hexokinase and glucose, 21-23 nt RNA was produced, albeit 6 times slower than when ATP was regenerated in the depleted lysate by the inclusion of creatine kinase and creatine phosphate. Therefore, ATP may not be required for production of the 21-23 nt RNA species, but may instead simply enhance its formation. Alternatively, ATP may be required for processing of the dsRNA, but at a concentration less than that remaining after hexokinase treatment. The molecular basis for the slower mobility of the small RNA fragments generated in the ATP-depleted lysate is not understood.

Wagner and Sun (Wagner and Sun, Nature, 391:744-745 (1998)) and Sharp (Sharp, Genes Dev., 13:139-41 (1999)) have speculated that the requirement for dsRNA in gene silencing by RNAi reflects the involvement of a dsRNA-specific adenosine deaminase in the process. dsRNA adenosine deaminases unwind dsRNA by converting adenosine to inosine, which does not base-pair with uracil. dsRNA adenosine deaminases function in the post-transcriptional editing of mRNA (for review see Bass, Trends Biochem. Sci., 22:157-62 (1997)). To test for the involvement of dsRNA adenosine deaminase in RNAi, the degree of conversion of adenosine to inosine in the 501 bp Rr-luc and 505 bp Pp-luc dsRNAs after incubation with *Drosophila* embryo lysate in a standard in vitro RNAi reaction was examined. Adenosine deamination in full-length dsRNA and the 21-23 nt RNA species was assessed by two-dimensional thin-layer chromatography. Inorganic phosphate ($P_i$,) was produced by the degradation of mononucleotides by phosphatases that contaminate commercially available nuclease P1 (Auxilien et al., J. Mol. Biol., 262:437-458 (1996)). The degree of adenosine deamination in the 21-23 nt species was also determined. The full-length dsRNA radiolabeled with [$^{32}$P]-adenosine was incubated in the lysate, and both the full-length dsRNA and the 21-23 nt RNA products were purified from a denaturing acrylamide gel, cleaved to mononucleotides with nuclease P1, and analyzed by two-dimensional thin-layer chromatography.

Figure 8A:
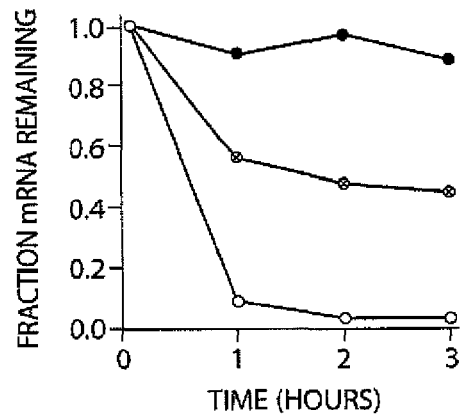
FIG. 8A is a graph of the of the denaturing agarose-gel analysis of Pp-luc mRNA incubated in a standard RNAi reaction with buffer, 505 nt Pp-asRNA, or 505 bp Pp-dsRNA for the times indicated showing that asRNA causes a small amount of RNAi in vitro.
Figure 8B:
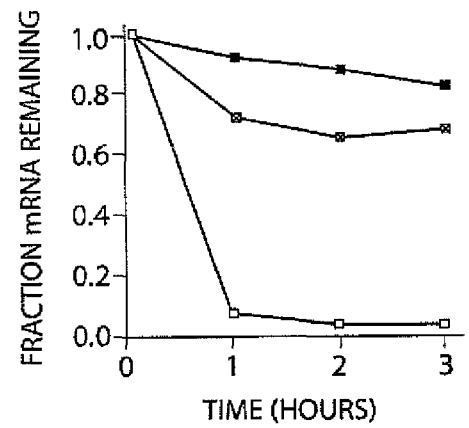
FIG. 8B is a graph of the of the denaturing agarose-gel analysis of Rr-luc mRNA incubated in a standard RNAi reaction with buffer, 505 nt Pp-asRNA, or 505 bp Pp-dsRNA for the times indicated showing that asRNA causes a small amount of RNAi in vitro.

A significant fraction of the adenosines in the full-length dsRNA were converted to inosine after 2 hours (3.1% and 5.6% conversion for Pp-luc and Rr-luc dsRNAs, respectively). In contrast, only 0.4% (Pp-dsRNA) or 0.7% (Rr-dsRNA) of the adenosines in the 21-23 nt species were deaminated. These data imply that fewer than 1 in 27 molecules of the 21-23 nt RNA species contain an inosine. Therefore, it is unlikely that dsRNA-dependent adenosine deamination within the 21-23 nt species is required for its production.

asRNA Generates a Small Amount of RNAi in vitro When mRNA was $^{32}$P-radiolabeled within the 5'-7-methyl-guanosine cap, stable 5' decay products accumulated during the RNAi reaction. Such stable 5' decay products were observed for both the Pp-luc and Rr-luc mRNAs when they were incubated with their cognate dsRNAs. Previously, it was reported that efficient RNAi does not occur when asRNA is used in place of dsRNA (Tuschl et al., Genes Dev., 13:3191-7 (1999)). Nevertheless, mRNA was measurably less stable when incubated with asRNA than with buffer (FIGS. 8A and 8B). This was particularly evident for the Rr-luc mRNA: approximately 90% of the RNA remained intact after a 3-hour incubation in lysate, but only 50% when asRNA was added. Less than 5% remained when dsRNA was added. Interestingly, the decrease in mRNA stability caused by asRNA was accompanied by the formation of a small amount of the stable 5'-decay products characteristic of the RNAi reaction with dsRNA. This finding parallels the observation that a small amount of 21-23 nt product formed from the asRNA when it was incubated with the mRNA (see above) and lends strength to the idea that asRNA can enter the RNAi pathway, albeit inefficiently.

mRNA Cleavage Sites are Determined by the Sequence of the dsRNA

Figure 9:
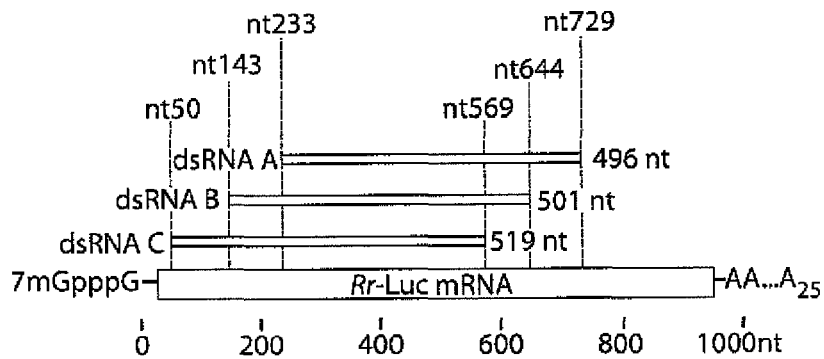
FIG. 9 is a schematic of the positions of the three dsRNAs, 'A,' 'B,' and 'C,' relative to the Rr-luc mRNA.

The sites of mRNA cleavage were examined using three different dsRNAs, 'A,' 'B,' and 'C,' displaced along the Rr-luc sequence by approximately 100 nts. Denaturing acrylamide-gel analysis of the stable, 5'-cleavage products produced after incubation of the Rr-luc mRNA for the indicated times with each of the three dsRNAs, 'A,' 'B,' and 'C,' or with buffer (.O slashed.) was performed. The positions of these relative to the Rr-luc mRNA sequence are shown in FIG. 9. Each of the three dsRNAs was incubated in a standard RNAi reaction with Rr-luc mRNA $^{32}$P-radiolabeled within the 5'-cap. In the absence of dsRNA, no stable 5'-cleavage products were detected for the mRNA, even after 3 hours of incubation in lysate. In contrast, after a 20-minute incubation, each of the three dsRNAs produced a ladder of bands corresponding to a set of mRNA cleavage products characteristic for that particular dsRNA. For each dsRNA, the stable, 5' mRNA cleavage products were restricted to the region of the Rr-luc mRNA that corresponded to the dsRNA (FIGS. 9 and 10). For dsRNA 'A,' the lengths of the 5' cleavage products ranged from 236 to just under ~750 nt; dsRNA 'A' spans nucleotides 233 to 729 of the Rr-luc mRNA. Incubation of the mRNA with dsRNA 'B' produced mRNA 5'-cleavage products ranging in length from 150 to ~600 nt; dsRNA 'B' spans nucleotides 143 to 644 of the mRNA. Finally, dsRNA 'C' produced mRNA cleavage products from 66 to ~500 nt in length. This dsRNA spans nucleotides 50 to 569 of the Rr-luc mRNA. Therefore, the dsRNA not only provides specificity for the RNAi reaction, selecting which mRNA from the total cellular mRNA pool will be degraded, but also determines the precise positions of cleavage along the mRNA sequence.

The mRNA is Cleaved at 21-23 Nucleotide Intervals

To gain further insight into the mechanism of RNAi, the positions of several mRNA cleavage sites for each of the three dsRNAs were mapped (FIG. 10). High resolution denaturing acrylamide-gel analysis of a subset of the 5'-cleavage products described above was performed. Remarkably, most of the cleavages occurred at 21-23 nt intervals (FIG. 10). This spacing is especially striking in light of our observation that the dsRNA is processed to a 21-23 nt RNA species and the finding of Hamilton and Baulcombe that a 25 nt RNA correlates with post-transcriptional gene silencing in plants (Hamilton and Baulcombe, Science, 286:950-2 (1999)). Of the 16 cleavage sites we mapped (2 for dsRNA 'A,' 5 for dsRNA 'B,' and 9 for dsRNA 'C'), all but two reflect the 21-23 nt interval. One of the two exceptional cleavages was a weak cleavage site produced by dsRNA 'C' (indicated by an open blue circle in FIG. 10). This cleavage occurred 32 nt 5' to the next cleavage site. The other exception is particularly intriguing. After four cleavages spaced 21-23 nt apart, dsRNA 'C' caused cleavage of the mRNA just nine nt 3' to the previous cleavage site (red arrowhead in FIG. 10). This cleavage occurred in a run of seven uracil residues and appears to "reset" the ruler for cleavage; the next cleavage site was 21-23 nt 3' to the exceptional site. The three subsequent cleavage sites that we mapped were also spaced 21-23 nt apart. Curiously, of the sixteen cleavage sites caused by the three different dsRNAs, fourteen occur at uracil residues. The significance of this finding is not understood, but it suggests that mRNA cleavage is determined by a process which measures 21-23 nt intervals and which has a sequence preference for cleavage at uracil. Results show that the 21-23 nt RNA species produced by incubation of 500 bp dsRNA in the lysate caused sequence-specific interference in vitro when isolated from an acrylamide gel and added to a new RNAi reaction in place of the full-length dsRNA.

A Model for dsRNA-Directed mRNA Cleavage

Figure 11:
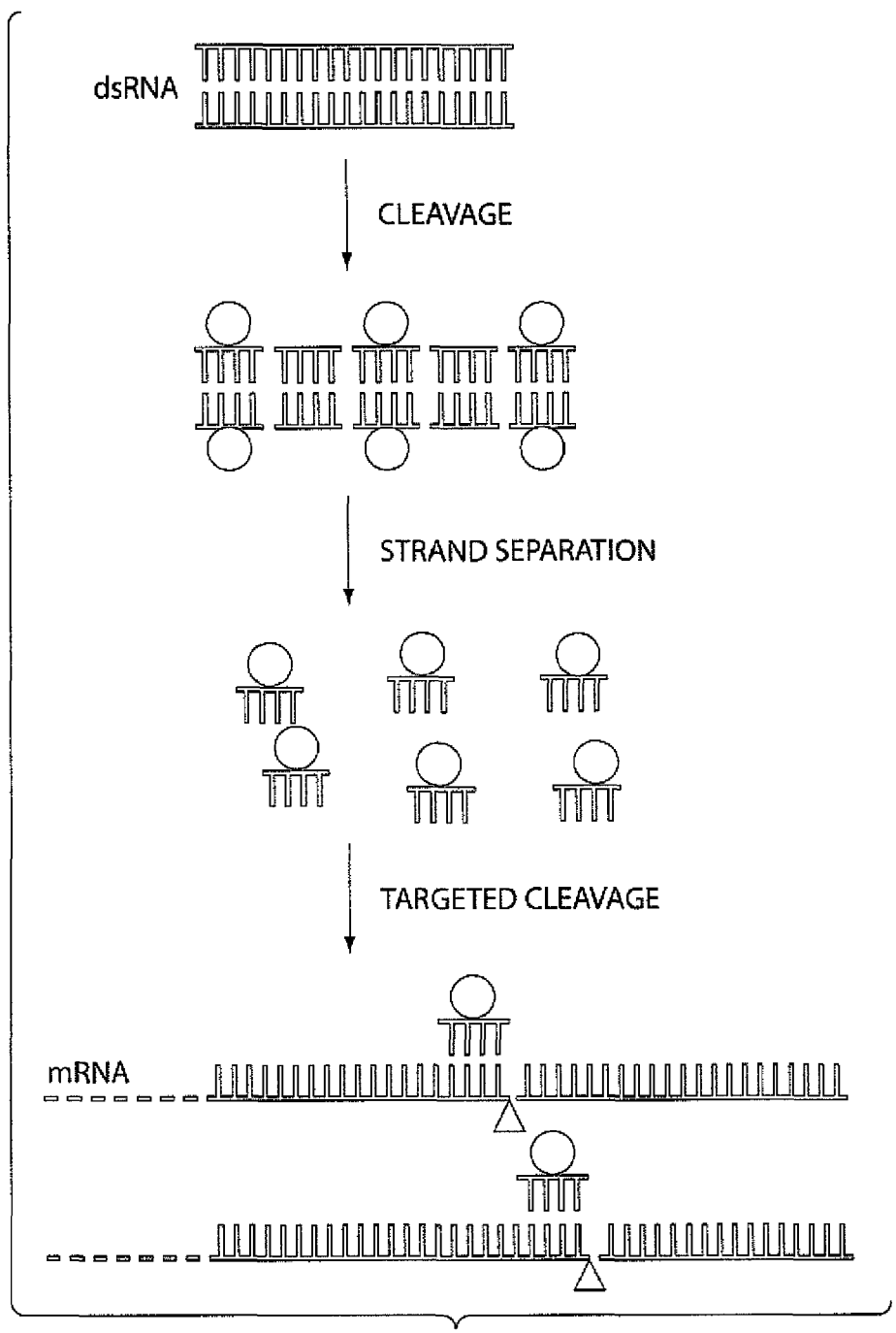
FIG. 11 is a proposed model for RNAi. RNAi is envisioned to begin with cleavage of the dsRNA to 21-23 nt products by a dsRNA-specific nuclease, perhaps in a multiprotein complex. These short dsRNAs might then be dissociated by an ATP-dependent helicase, possibly a component of the initial complex, to 21-23 nt asRNAs that could then target the mRNA for cleavage. The short asRNAs are imagined to remain associated with the RNAi-specific proteins (circles) that were originally bound by the full-length dsRNA, thus explaining the inefficiency of asRNA to trigger RNAi in vivo and in vitro. Finally, a nuclease (triangles) would cleave the mRNA.
Figure 12:
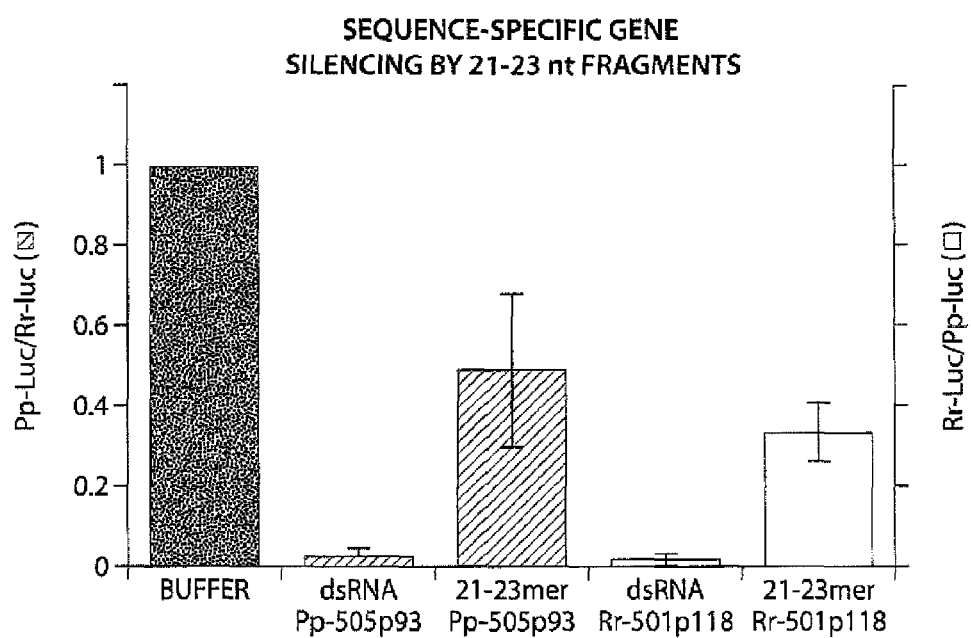
FIG. 12 is a bar graph showing sequence-specific gene silencing by 21-23 nt fragments. Ratio of luciferase activity after targeting of Pp-Luc and Rr-Luc mRNA by 5 nM Pp-Luc or Rr-Luc dsRNA (500 bp) or 21-23 nt fragments isolated from a previous incubation of the respective dsRNA in *Drosophila* lysate. The amount of isolated 21-23 mers present in the incubation reaction correspond to approximately the same amount of 21-23 mers generated during an incubation reaction with 5 nM 500 bp dsRNA. The data are average values of 3 trials and the standard deviation is given by error bars. Luciferase activity was normalized to the buffer control.

Without wishing to be bound by theory, the biochemical data described herein, together with recent genetic experiments in *C. elegans* and *Neurospora* (Cogoni and Macino, Nature, 399:166-9 (1999); Grishok et al., Science, 287:2494-7 (2000); Ketting et al., Cell, 99:133-41 (1999); Tabara et al., Cell, 99:123-32 (1999)), suggest a model for how dsRNA targets mRNA for destruction (FIG. 11). In this model, the dsRNA is first cleaved to 21-23 nt long fragments in a process likely to involve genes such as the *C. elegans* loci rde-1 and rde-4. The resulting fragments, probably as short asRNAs bound by RNAi-specific proteins, would then pair with the mRNA and recruit a nuclease that cleaves the mRNA. Alternatively, strand exchange could occur in a protein-RNA complex that transiently holds a 21-23 nt dsRNA fragment close to the mRNA. Separation of the two strands of the dsRNA following fragmentation might be assisted by an ATP-dependent RNA helicase, explaining the observed ATP enhancement of 21-23 nt RNA production.

It is likely that each small RNA fragment produces one, or at most two, cleavages in the mRNA, perhaps at the 5' or 3' ends of the 21-23 nt fragment. The small RNAs may be amplified by an RNA-directed RNA polymerase such as that encoded by the ego-1 gene in *C. elegans* (Smardon et al., Current Biology, 10:169-178 (2000)) or the qde-1 gene in *Neurospora* (Cogoni and Macino, Nature, 399:166-9 (1999)), producing long-lasting post-transcriptional gene silencing in the absence of the dsRNA that initiated the RNAi effect. Heritable RNAi in *C. elegans* requires the rde-1 and rde-4 genes to initiate, but not to persist in subsequent generations. The rde-2, rde-3, and mut-7 genes in *C. elegans* are required in the tissue where RNAi occurs, but are not required for initiation of heritable RNAi (Grishok et al., Science, in press 2000). These 'effector' genes (Grishok et al., Science, in press 2000) are likely to encode proteins functioning in the actual selection of mRNA targets and in their subsequent cleavage. ATP may be required at any of a number of steps during RNAi, including complex formation on the dsRNA, strand dissociation during or after dsRNA cleavage, pairing of the 21-23 nt RNAs with the target mRNA, mRNA cleavage, and recycling of the targeting complex. Testing these ideas with the in vitro RNAi system will be an important challenge for the future. Some genes involved in RNAi are also important for transposon silencing and co-suppresion. Co-suppression is a broad biological phenomenon spanning plants, insects and perhaps humans. The most likely mechanism in *Drosophila* melanogaster is transcriptional silencing (Pal-Bhanra et al, Cell 99: 35-36. Thus, 21-23 nt fragments are likely to be involved in transcriptional control, as well as in post-transcriptional cotrol Example 3

Isolated 21-23 Mers Caused Sequence-Specific Interference when Added to a New RNAi Reaction Isolation of 21-23 Nt Fragments from Incubation Reaction of 500 Bp dsRNA in Lysate.

Double-stranded RNA (500 bp from) was incubated at 10 nM concentration in *Drosophila* embryo lysate for 3 h at 25° C. under standard conditions as described herein. After deproteinization of the sample, the 21-23 nt reaction products were separated from to unprocessed dsRNA by denaturing polyacrylamide (15%) gel electrophoresis. For detection of the non-radiolabeled 21-23 nt fragments, an incubation reaction with radiolabeled dsRNA was loaded in a separate lane of the same gel. Gel slices containing the non-radioactive 21-23 nt fragments were cut out and the 21-23 nt fragments were eluted from the gel slices at 4° C. overnight in 0.4 ml 0.3 M NaCl. The RNA was recovered from the supernatant by ethanol precipitation and centrifugation. The RNA pellet was dissolved in 10 µl of lysis buffer. As control, gel slices slightly above and below the 21-23 nt band were also cut out and subjected to the same elution and precipitation procedures. Also, a non-incubated dsRNA loaded on the 15% gel and a gel slice corresponding to 21-23 nt fragments was cut out and eluted. All pellets from the control experiments were dissolved in 10 µl lysis buffer. The losses of RNA during recovery from gel slices by elution are approx. 50%.

Incubation of Purified 21-23 Nt Fragments in a Translation-Based RNAi Assay

1 µl of the eluted 21-23 mer or control RNA solution was used for a standard 10 µl RNAi incubation reaction (see above). The 21-23 mers were preincubated in the lysate containing reaction mixture for 10 or 30 min before the addition of the target and control mRNA. During pre-incubation, proteins involved in RNA interference may re-associate with the 21-23 mers due to a specific signal present on these RNAs. The incubation was continued for another hour to allow translation of the target and control mRNAs. The reaction was quenched by the addition of passive lysis buffer (Promega), and luciferase activity was measured. The RNA interference is the expressed as the ratio of target to control luciferase activity normalized by an RNA-free buffer control. Specific suppression of the target gene was observed with either 10 or 30 minutes preincubation. The suppression was reproducible and reduced the relative ratio of target to control by 2-3 fold. None of the RNA fragments isolated as controls showed specific interference. For comparison, incubation of 5 nM 500 bp dsRNA (10 min pre-incubation) affects the relative ratio of control to target gene approx. 30-fold.

Stability of Isolated 21-23 Nt Fragments in a New Lysate Incubation Reaction.

Consistent with the observation of RNAi mediated by purified 21-23 nt RNA fragment, it was found that 35% of the input 21-23 nt RNA persists for more than 3 h in such an incubation reaction. This suggests that cellular factors associate with the deproteinized 21-23 nt fragments and reconstitute a functional mRNA-degrading particle. Signals connected with these 21-23 nt fragments, or their possible double stranded nature or specific lengths are likely responsible for this observation. The 21-23 nt fragments have a terminal 3' hydroxyl group, as evidenced by altered mobility on a sequencing gel following periodate treatment and beta-elimination.

Example 4

Figure 13A:
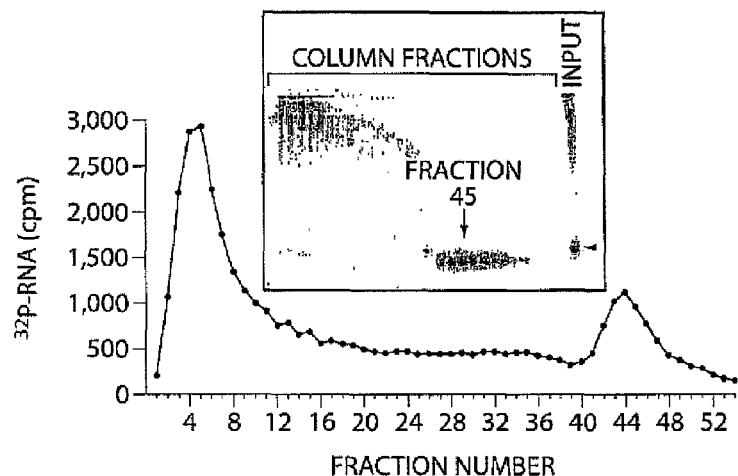
FIG. 13A illustrates the purification of RNA fragments on a Superdex HR 200 10/30 gel filtration column (Pharmacia) using the method described in Example 4. dsRNA was 32P-labeled, and the radioactivity recovered in each column fraction is graphed. The fractions were also analyzed by denaturing gel electrophoresis (inset).

21-23-Mers Purified by Non-Denaturing Methods Caused Sequence-Specific Interference when Added to a New RNAi Reaction Fifty nanomolar double-stranded RNA (501 bp Rr-luc dsRNA, as described in example 1) was incubated in a 1 ml in vitro reaction with lysate at 25° C. (see example 1). The reaction was then stopped by the addition of an equal volume of 2×PK buffer (see example 1) and proteinase K was added to a final concentration of 1.8 µg/µl. The reaction was incubated for an additional 1 h at 25° C., phenol extracted, and then the RNAs were precipitated with 3 volumes of ethanol. The ethanol precipitate was collected by centrifugation, and the pellet was resuspended in 100 µl of lysis buffer and applied to a Superdex HR 200 10/30 gel filtration column (Pharmacia) run in lysis buffer at 0.75 ml/min. 200 µl fractions were collected from the column. Twenty µl of 3 M sodium acetate and 20 µg glycogen was added to each fraction, and the RNA was recovered by precipitation with 3 volumes of ethanol. The precipitates were resuspended in 30 µl of lysis buffer. Column profiles following the fractionation of 32P-labeled input RNA are shown in FIG. 13A.

One microliter of each resuspended fraction was tested in a 10 µl standard in vitro RNAi reaction (see example 1). This procedure yields a concentration of RNA in the in vitro RNAi reaction that is approximately equal to the concentration of that RNA species in the original reaction prior to loading on the column. The fractions were preincubated in the lysate containing reaction mixture for 30 min before the addition of 10 nM Rr-luc mRNA target and 10 nM Pp-luc control mRNA. During pre-incubation, proteins involved in RNA interference may re-associate with the 21-23-mers due to a specific signal present on these RNAs. The incubation was continued for another three hours to allow translation of the target and control mRNAs. The reaction was quenched by the addition of passive lysis buffer (Promega), and luciferase activity was measured. The suppression of Rr-luc mRNA target expression by the purified 21-23 nt fragments was reproducible and reduced the relative ratio of target to control by >30-fold, an amount comparable to a 50 nM 500 bp dsRNA control. Suppression of target mRNA expression was specific: little or no effect on the expression of the Pp-luc mRNA control was observed.

Figure 13B:
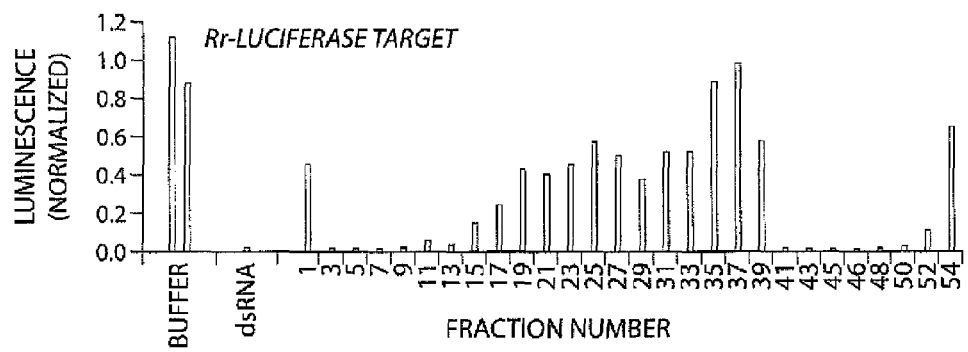
FIG. 13B demonstrates the ability of the Rr-luciferase RNA, after incubation in the *Drosophila* lysate and fractionation as in FIG. 13A, to mediate sequence-specific interference with the expression of a Rr-luciferase target mRNA. One microliter of each resuspended fraction was tested in a 10 microliter in vitro RNAi reaction (see Example 1). This procedure yields a concentration of RNA in the standard in vitro RNAi reaction that is approximately equal to the concentration of that RNA species in the original reaction prior to loading on the column. Relative luminescence per second has been normalized to the average value of the two buffer controls.
Figure 13C:
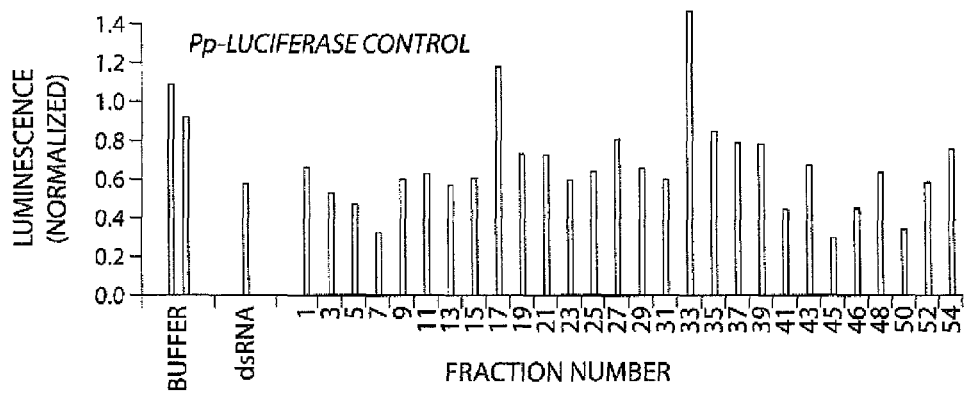
FIG. 13C is the specificity control for FIG. 13B. It demonstrates that the fractionated RNA of FIG. 13B does not efficiently mediate sequence-specific interference with the expression of a Pp-luciferase mRNA. Assays are as in FIG. 13B.

The data show that the both the fractions containing uncleaved dsRNA (fractions 3-5) or long, partially cleaved dsRNA (fractions 7-13) and the fractions containing the fully processed 21-23 nt siRNAs (fractions 41-50) mediate effective RNA interference in vitro (FIG. 13B). Suppression of target mRNA expression was specific: little or no effect on the expression of the Pp-luc mRNA control was observed (FIG. 13C). These data, together with those in the earlier examples, demonstrate that the 21-23 nt siRNAs are (1) true intermediates in the RNAi pathway and (2) effective mediators of RNA interference in vitro.

Example 5

21-Nucleotide siRNA Duplexes Mediate RNA Interference in Human Tissue Cultures Methods
RNA Preparation 21 nt RNAs were chemically synthesized using Expedite RNA phosphoramidites and thymidine phosphoramidite (Proligo, Germany). Synthetic oligonucleotides were deprotected and gel-purified (Elbashir, S. M., Lendeckel, W. & Tuschl, T., Genes & Dev. 15, 188-200 (2001)), followed by Sep-Pak C18 cartridge (Waters, Milford, Mass., USA) purification (Tuschl, t., et al., Biochemistry, 32:11658-11668 (1993)). The siRNA sequences targeting GL2 (Acc. X65324) and GL3 luciferase (Acc. U47296) corresponded to the coding regions 153-173 relative to the first nucleotide of the start codon, siRNAs targeting RL (Acc. AF025846) corresponded to region 119-129 after the start codon. Longer RNAs were transcribed with T7 RNA polymerase from PCR products, followed by gel and Sep-Pak purification. The 49 and 484 bp GL2 or GL3 dsRNAs corresponded to position 113-161 and 113-596, respectively, relative to the start of translation; the 50 and 501 bp RL dsRNAs corresponded to position 118-167 and 118-618, respectively. PCR templates for dsRNA synthesis targeting humanized GFP (hG) were amplified from pAD3 (Kehlenbach, R. H., et al., J. Cell Biol., 141:863-874 (1998)), whereby 50 and 501 bp hG dsRNA corresponded to position 118-167 and 118-618, respectively, to the start codon.

For annealing of siRNAs, 20 µM single strands were incubated in annealing buffer (100 mM potassium acetate, 30 mM HEPES-KOH at pH 7.4, 2 mM magnesium acetate) for 1 min at 90° C. followed by 1 h at 37° C. The 37° C. incubation step was extended overnight for the 50 and 500 bp dsRNAs, and these annealing reactions were performed at 8.4 µM and 0.84 µM strand concentrations, respectively.

Cell Culture

S2 cells were propagated in Schneider's *Drosophila* medium (Life Technologies) supplemented with 10% FBS, 100 units/ml penicillin, and 100 µg/ml streptomycin at 25° C. 293, NIH/3T3, HeLa S3, COS-7 cells were grown at 37° C. in Dulbecco's modified Eagle's medium supplemented with 10% FBS, 100 units/ml penicillin, and 100 µg/ml streptomycin. Cells were regularly passaged to maintain exponential growth. 24 h before transfection at approx. 80% confluency, mammalian cells were trypsinized and diluted 1:5 with fresh medium without antibiotics (1-3×10⁵ cells/ml) and transferred to 24-well plates (500 µl/well). S2 cells were not trypsinized before splitting. Transfection was carried out with Lipofectamine 2000 reagent (Life Technologies) as described by the manufacturer for adherent cell lines. Per well, 1.0 µg pGL2-Control (Promega) or pGL3-Control (Promega), 0.1 µg pRL-TK (Promega) and 0.28 µg siRNA duplex or dsRNA, formulated into liposomes, were applied; the final volume was 600 µl per well. Cells were incubated 20 h after transfection and appeared healthy thereafter. Luciferase expression was subsequently monitored with the Dual luciferase assay (Promega). Transfection efficiencies were determined by fluorescence microscopy for mammalian cell lines after co-transfection of 1.1 µg hGFP-encoding pAD3[22] and 0.28 µg invGL2 siRNA, and were 70-90%. Reporter plasmids were amplified in XL-1 Blue (Strategene) and purified using the Qiagen EndoFree Maxi Plasmid Kit.

Results

RNA interference (RNAi) is the process of sequence-specific, post-transcriptional gene silencing in animals and plants, initiated by double-stranded RNA (dsRNA) homologous in sequence to the silenced gene (Fire, A., Trends Genet., 15:358-363 (1999); Sharp, P. A. & Zamore, P. D., Science, 287:2431-2433 (2000); Sijen, T. & Kooter, J. M., Bioessays, 22:520-531 (2000); Bass, B. L., Cell, 101:235-238 (2000); Hammond, S. M., et al., Nat. Rev. Genet., 2:110-119 (2001)). The mediators of sequence-specific mRNA degradation are 21 and 22 nt small interfering RNAs (siRNAs) generated by RNase III cleavage from longer dsRNAs[6-10] (Hamilton, A. J. & Baulcombe, D. C, Science, 286:950-952 (1999); Hammond, S. M., et al., Nature, 404:293-296 (2000); Zamore, P. D., et al., Cell, 101:25-33 (2000); Bernstein, E., et al, Naature, 409:363-366 (2001); Elbashir, S. M., et al., Genes & Dev., 15:188-200 (2001)). As shown herein, 21 nt siRNA duplexes are able to specifically suppress reporter gene expression in multiple mammalian tissue cultures, including human embryonic kidney (293) and HeLa cells. In contrast to 50 or 500 bp dsRNAs, siRNAs do not activate the interferon response. These results indicate that siRNA duplexes are a general tool for sequence-specific inactivation of gene function in mammalian cells.

Figures 14A, 14B:
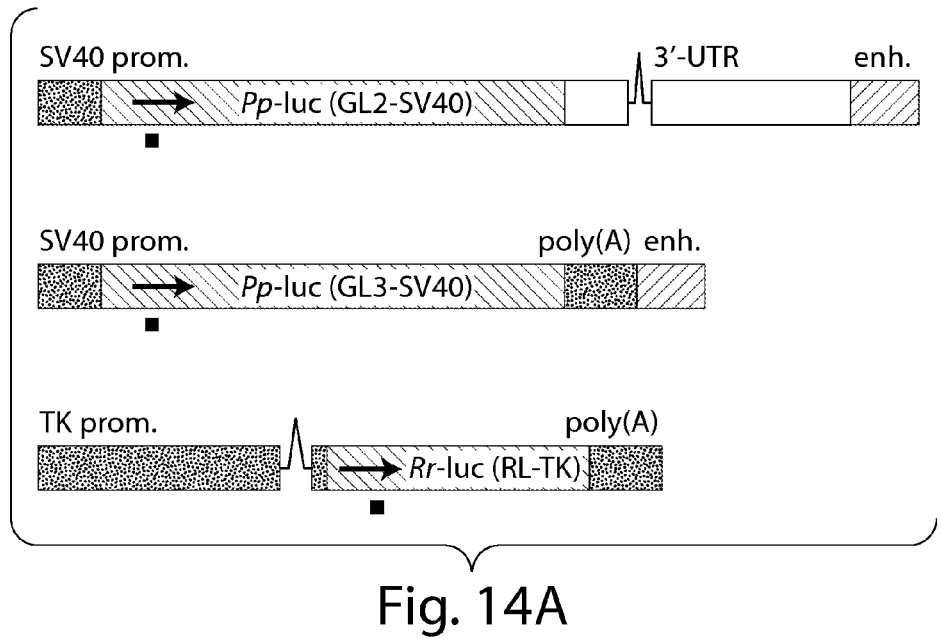
FIGS. 14A and 14B are schematic representations of reporter constructs and siRNA duplexes.
Figure 15G:
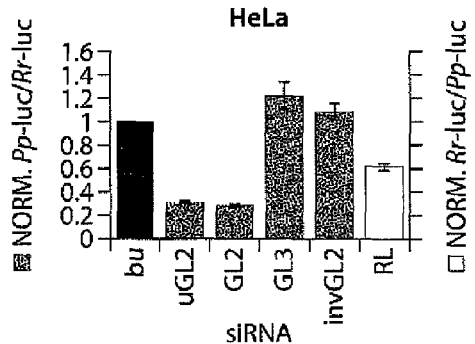
Figure 15H:
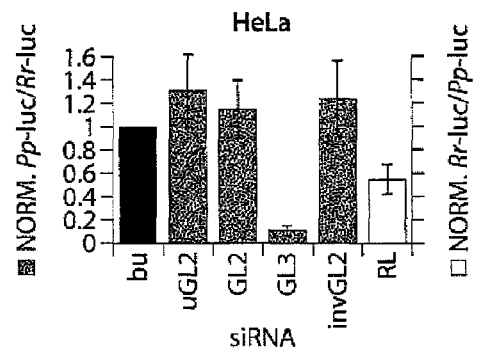
Figure 15I:
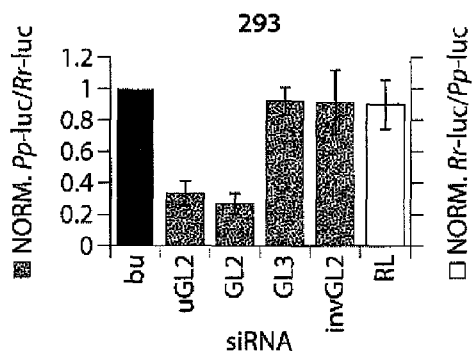
Figure 15J:
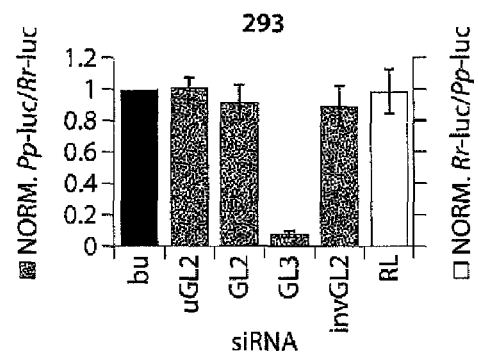

Base-paired 21 and 22 nt siRNAs with overhanging 3' ends mediate efficient sequence-specific mRNA degradation in lysates prepared from *D. melanogaster* embryos (Elbashir, S. M., et al., Genes & Dev., 15:188-200 (2001)). To test whether siRNAs are also capable of mediating RNAi in tissue culture, 21 nt siRNA duplexes with symmetric 2 nt 3' overhangs directed against reporter genes coding for sea pansy (*Renilla reniformis*) and two sequence variants of firefly (*Photinus pyralis*, GL2 and GL3) luciferases (FIGS. 14A, 14B) were constructed. The siRNA duplexes were co-transfected with the reporter plasmid combinations pGL2/pRL or pGL3/pRL, into *D. melanogaster* Schneider S2 cells or mammalian cells using cationic liposomes. Luciferase activities were determined 20 h after transfection. In all cell lines tested, specific reduction of the expression of the reporter genes in the presence of cognate siRNA duplexes was observed (FIGS. 15A-15J). Remarkably, the absolute luciferase expression levels were unaffected by non-cognate siRNAs, indicating the absence of harmful side effects by 21 nt RNA duplexes (e.g. FIGS. 16A-16D, for HeLa cells). In *D. melanogaster* S2 cells (FIGS. 15A, 15B), the specific inhibition of luciferases was complete, and similar to results previously obtained for longer dsRNAs (Hammond, S. M., et al., Nature, 404:293-296 (2000); Caplen, N. J., et al., sGene, 252:95-105 (2000); Clemens, M & Williams, B., Cell, 13:565-572 (1978); Ui-Tei, K., et al., FEBS Letters, 479:79-82 (2000)). In mammalian cells, where the reporter genes were 50- to 100-fold stronger expressed, the specific suppression was less complete (FIGS. 15C-15J). GL2 expression was reduced 3- to 12-fold, GL3 expression 9- to 25-fold, and RL expression 1- to 3-fold, in response to the cognate siRNAs. For 293 cells, targeting of RL luciferase by RL siRNAs was ineffective, although GL2 and GL3 targets responded specifically (FIGS. 15I, 15J). It is likely that the lack of reduction of RL expression in 293 cells is due to its 5- to 20-fold higher expression compared to any other mammalian cell line tested and/or to limited accessibility of the target sequence due to RNA secondary structure or associated proteins. Nevertheless, specific targeting of GL2 and GL3 luciferase by the cognate siRNA duplexes indicated that RNAi is also functioning in 293 cells.

The 2 nt 3' overhang in all siRNA duplexes, except for uGL2, was composed of (2'-deoxy) thymidine. Substitution of uridine by thymidine in the 3' overhang was well tolerated in the *D. melanogaster* in vitro system, and the sequence of the overhang was uncritical for target recognition (Elbashir, S. M., et al., Genes & Dev., 15:188-200 (2001)). The thymidine overhang was chosen, because it is supposed to enhance nuclease resistance of siRNAs in the tissue culture medium and within transfected cells. Indeed, the thymidine-modified GL2 siRNA was slightly more potent than the unmodified uGL2 siRNA in all cell lines tested (FIGS. 15A, 15C, 15E, 15G, 15I). It is conceivable that further modifications of the 3' overhanging nucleotides will provide additional benefits to the delivery and stability of siRNA duplexes.

In co-transfection experiments, 25 nM siRNA duplexes with respect to the final volume of tissue culture medium were used (FIGS. 15A-15J, 16A-16F). Increasing the siRNA concentration to 100 nM did not enhance the specific silencing effects, but started to affect transfection efficiencies due to competition for liposome encapsulation between plasmid DNA and siRNA. Decreasing the siRNA concentration to 1.5 nM did not reduce the specific silencing effect, even though the siRNAs were now only 2- to 20-fold more concentrated than the DNA plasmids. This indicates that siRNAs are extraordinarily powerful reagents for mediating gene silencing, and that siRNAs are effective at concentrations that are several orders of magnitude below the concentrations applied in conventional antisense or ribozyme gene targeting experiments.

Figure 16A:
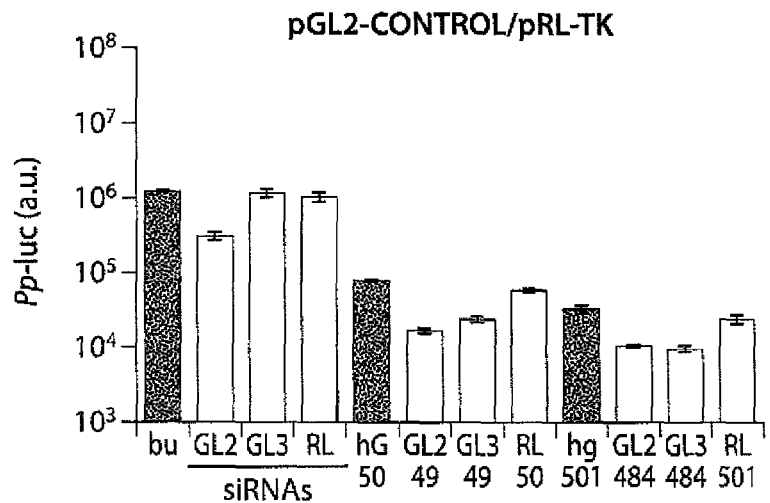
FIGS. 16A-16F are graphs showing the effects of 21 nt siRNAs, 50 bp, and 500 bp dsRNAs on luciferase expression in HeLa cells. The exact length of the long dsRNAs is indicated below the bars.
Figure 16B:
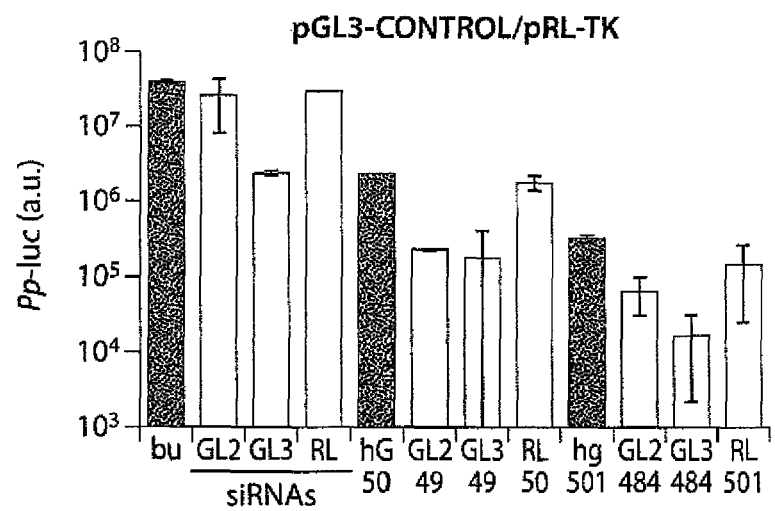
Figure 16C:
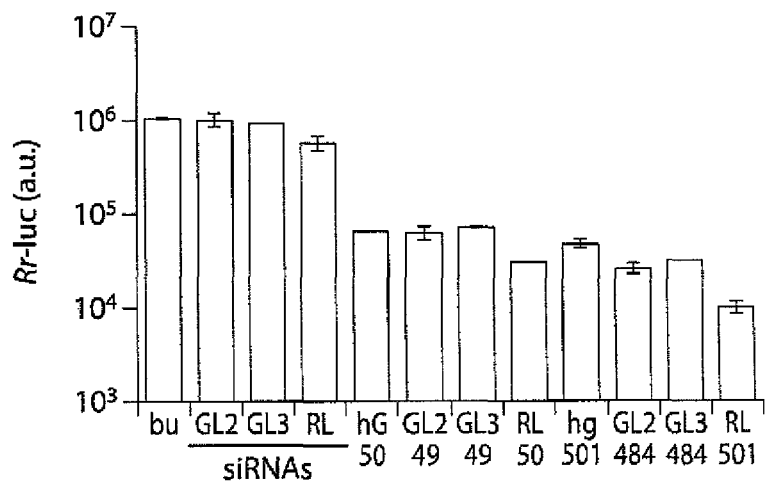
Figure 16D:
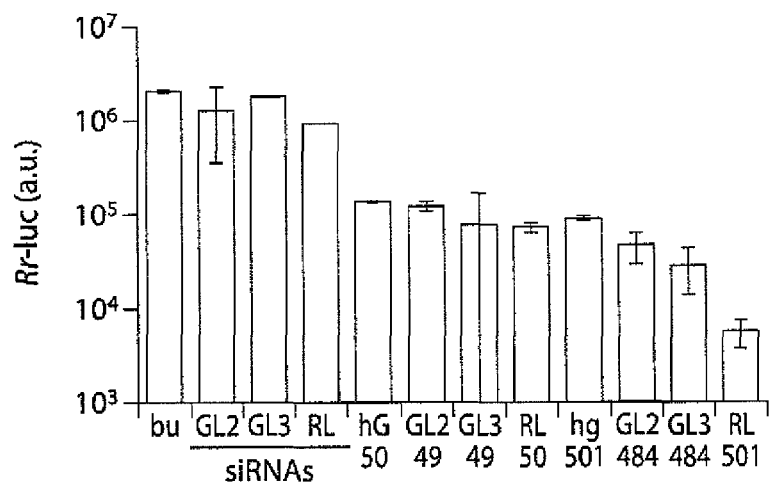
Figure 16E:
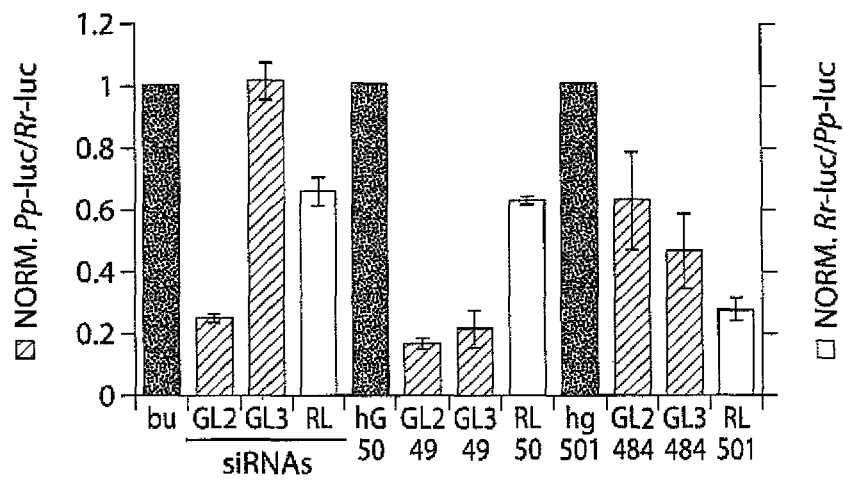
Figure 16F:
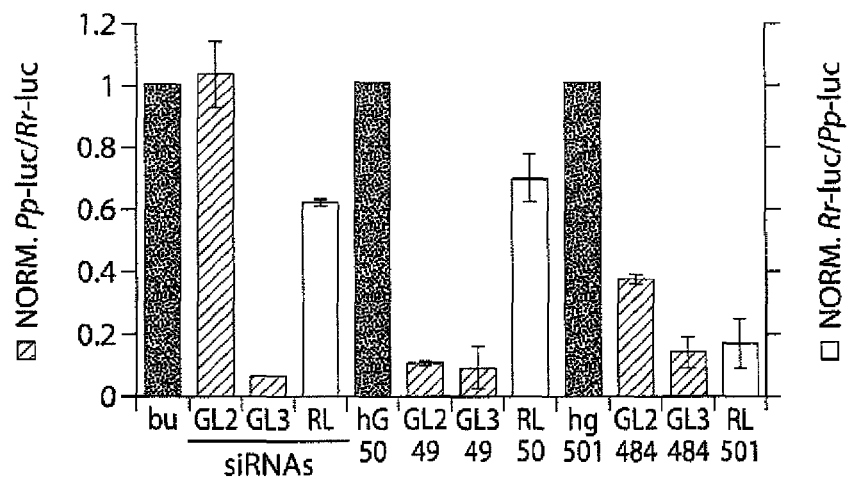

In order to monitor the effect of longer dsRNAs on mammalian cells, 50 and 500 bp dsRNAs cognate to the reporter genes were prepared. As non-specific control, dsRNAs from humanized GFP (hG) (Kehlenbach, R. H., et al., J. Cell Biol., 141:863874 (1998)) was used. When dsRNAs were co-transfected, in identical amounts (not concentrations) to the siRNA duplexes, the reporter gene expression was strongly and unspecifically reduced. This effect is illustrated for HeLa cells as a representative example (FIGS. 16A-16D). The absolute luciferase activities were decreased unspecifically 10- to 20-fold by 50 bp dsRNA, and 20- to 200-fold by 500 bp dsRNA co-transfection, respectively. Similar unspecific effects were observed for COS-7 and NIH/3T3 cells. For 293 cells, a 10- to 20-fold unspecific reduction was observed only for 500 bp dsRNAs. Unspecific reduction in reporter gene expression by dsRNA >30 bp was expected as part of the interferon response (Matthews, M., Interactions between viruses and the cellular machinery for protein synthesis in Translational Control (eds., Hershey, J., Matthews, M. & Sonenberg, N.) 505-548 (Cold Spring Harbor Laboratory Press, Plainview, N. Y.; 1996); Kumar, M. & Carmichael, G. G., Microbiol. Mol. Biol. Rev., 62:1415-1434 (1998); Stark, G. R., et al., Annu. Rev. Biochem., 67:227-264 (1998)). Surprisingly, despite the strong unspecific decrease in reporter gene expression, additional sequence-specific, dsRNA-mediated silencing were reproducibly detected. The specific silencing effects, however, were only apparent when the relative reporter gene activities were normalized to the hG dsRNA controls (FIGS. 16E, 16F). A 2- to 10-fold specific reduction in response to cognate dsRNA was observed, also in the other three mammalian cell lines tested. Specific silencing effects with dsRNAs (356-1662 bp) were previously reported in CHO-K1 cells, but the amounts of dsRNA required to detect a 2- to 4-fold specific reduction were about 20-fold higher than in our experiments (Ui-Tei, K., et al., FEBS Letters, 479:79-82 (2000)). Also, CHO-K1 cells appear to be deficient in the interferon response. In another report, 293, NIH/3T3, and BHK-21 cells were tested for RNAi using luciferase/lacZ reporter combinations and 829 bp specific lacZ or 717 bp unspecific GFP dsRNA (Caplen, N. J., et al., Gene, 252:95105 (2000)). The failure of detecting RNAi in this case is likely due to the less sensitive luciferase/lacZ reporter assay and the length differences of target and control dsRNA. Taken together, the results described herein indicate that RNAi is active in mammalian cells, but that the silencing effect is difficult to detect if the interferon system is activated by dsRNA >30 bp.

The mechanism of the 21 nt siRNA-mediated interference process in mammalian cells remains to be uncovered, and silencing may occur post-transcriptional and/or transcriptional. In D. melanogaster lysate, siRNA duplexes mediate post-transcriptional gene silencing by reconstitution of a siRNA-protein complexes (siRNPs), which are guiding mRNA recognition and targeted cleavage (Hammond, S. M., et al., Nature, 404:293-296 (2000); Zamore, P. D., et al., Cell, 101:25-33 (2000); Elbashir, S. M., et al., Genes & Dev., 15:188-200 (2001)). In plants, dsRNA-mediated post-transcriptional silencing has also been linked to RNA-directed DNA methylation, which may also be directed by 21 nt siRNAs (Wassenegger, M., Plant Mol. Biol, 43:203-220 (2000); Finnegan, E. J., et al., Curr. Biol, 11:R99-R102 (2000)). Methylation of promoter regions can lead to transcriptional silencing (Metter, M. F., et al., EMBO J., 19:5194-5201 (2000)), but methylation in coding sequences must not (Wang, M.-B., RNA, 7:16-28 (2001)). DNA methylation and transcriptional silencing in mammals are well-documented processes (Kass, S. U., et al., Trends Genet., 13:444-449 (1997); Razin, A., EMBO J, 17:4905-4908 (1998)), yet they have not been linked to post-transcriptional silencing. Methylation in mammals is predominantly directed towards CpG residues. Because there is no CpG in the RL siRNA, but RL siRNA mediates specific silencing in mammalian tissue culture, it is unlikely that DNA methylation is critical for our observed silencing process. In summary, described herein, is siRNA-mediated gene silencing in mammalian cells. The use of 21 nt siRNAs holds great promise for inactivation of gene function in human tissue culture and the development of gene-specific therapeutics.

While this invention has been particularly shown and described with reference to preferred embodiments thereof, it will be understood by those skilled in the art that various changes in form and details may be made therein without departing from the scope of the invention encompassed by the appended claims

What is claimed is:

1. A method of producing a double-stranded RNA molecule of from 21 to 23 nucleotides in length that mediates RNA interference of an mRNA, comprising:
    (a) chemically synthesizing the double-stranded RNA molecule in the form of two separate complementary RNA strands which are not covalently linked and each RNA strand has a length of from 21 to 23 nucleotides, wherein the sequence of one strand has sufficient sequence correspondence to the mRNA to mediate RNA interference by directing cleavage of the mRNA within the region of sequence correspondence, and
    (b) combining the strands of (a) under conditions under which the double-stranded RNA molecule is produced, thereby producing the double-stranded RNA molecule of from 21 to 23 nucleotides that mediates RNA interference of the mRNA.

2. The method according to claim 1, wherein the RNA strands are recombinantly produced.

3. The method of claim 1, wherein the mRNA is a mammalian cellular mRNA.

4. The method of claim 1, wherein the RNA molecule comprises a terminal 3' hydroxyl group.

5. The method of claim 1, wherein one or more nucleotides of the double-stranded RNA molecule are a non-naturally occurring nucleotide.

6. The method of claim 1, wherein one or more nucleotides of the double-stranded RNA molecule are a deoxyribonucleotide.

7. The method of claim 1, wherein one or more nucleotides of the double-stranded RNA molecule are a non-standard nucleotide.

8. The method of claim 1, wherein the mRNA is a human mRNA.

9. The method of claim 1, wherein the mRNA is a viral mRNA.

10. The method of claim 1, wherein the double-stranded RNA molecule is perfectly complementary to the mRNA.

11. The method of claim 1, wherein the double-stranded RNA molecule is 21 nucleotides in length.

12. The method of claim 1, wherein the double-stranded RNA molecule is 22 nucleotides in length.

13. The method of claim 1, wherein the double-stranded RNA molecule is 23 nucleotides in length.

14. A method of producing a double-stranded RNA molecule of from 21 to 23 nucleotides in length that mediates RNA interference of an mRNA, comprising:
    chemically synthesizing the double-stranded RNA molecule such that the RNA is in the form of two separate complementary RNA strands which are not covalently linked and each RNA strand has a length of from 21 to 23 nucleotides, wherein the sequence of one strand has sufficient sequence correspondence to the mRNA to mediate RNA interference of the mRNA, and
    thereby producing the double-stranded RNA molecule of from 21 to 23 nucleotides that mediates RNA interference of the mRNA.

15. The method of claim 1, wherein the mRNA encodes a protein whose presence in a human is associated with a disease or undesirable condition.

16. The method of claim 1, wherein the double-stranded RNA molecule is effective to reduce expression of the mRNA.

17. The method of claim 1, further comprising testing the double-stranded RNA molecule to determine the level of RNA interference effected by the double-stranded RNA.

18. The method of claim 1, wherein each RNA strand of the double-stranded RNA molecule comprises a terminal 3' hydroxyl group.

19. The method of claim 1, wherein the double-stranded RNA molecule comprises one or more naturally occurring nucleotides.

20. The method of claim 1, wherein the double-stranded RNA molecule comprises one or more naturally occurring nucleotides and one or more non-naturally occurring nucleotides.

21. The method of claim 14, wherein the double-stranded RNA molecule comprises a terminal 3' hydroxyl group.

22. The method of claim 14, wherein each RNA strand of the double-stranded RNA molecule comprises a terminal 3' hydroxyl group.

23. The method of claim 14, wherein the double-stranded RNA molecule comprises one or more non-naturally occurring nucleotides.

24. The method of claim 14, wherein the double-stranded RNA molecule comprises one or more non-standard nucleotides.

25. The method of claim 14, wherein the double-stranded RNA molecule comprises one or more deoxyribonucleotides.

26. The method of claim 14, wherein the double-stranded RNA molecule comprises one or more naturally occurring nucleotides.

27. The method of claim 14, wherein the double-stranded RNA molecule comprises one or more naturally occurring nucleotides and one or more non-naturally occurring nucleotides.

28. The method of claim 14, wherein the mRNA is a mammalian cellular mRNA.

29. The method of claim 14, wherein the mRNA is a human mRNA.

30. The method of claim 14, wherein the mRNA encodes a protein whose presence in a human is associated with a disease or undesirable condition.

31. The method of claim 14, wherein the mRNA is a viral mRNA.

32. The method of claim 14, wherein the double-stranded RNA molecule is perfectly complementary to the mRNA.

33. The method of claim 14, wherein a strand of the double-stranded RNA molecule is 21 nucleotides in length.

34. The method of claim 14, wherein a strand of the double-stranded RNA molecule is 22 nucleotides in length.

35. The method of claim 14, wherein a strand of the double-stranded RNA molecule is 23 nucleotides in length.

36. A method of producing a double-stranded RNA molecule of 21 to 23 nucleotides in length that mediates RNA interference, comprising:
synthesizing the double-stranded RNA molecule such that the RNA is in the form of two separate complementary RNA strands which are not covalently linked and each RNA strand has a length of from 21 to 23 nucleotides, wherein the sequence of one strand has sufficient sequence complementarity to a target mRNA to mediate RNA interference of the target mRNA, and wherein the double-stranded RNA molecule comprises one or more of: a non-naturally occurring nucleotide, a non-standard nucleotide, or a deoxyribonucleotide, thereby producing the double-stranded RNA molecule.

37. The method of claim 36, wherein a strand of the double-stranded RNA molecule is 21 nucleotides in length.

38. The method of claim 36, wherein a strand of the double-stranded RNA molecule is 22 nucleotides in length.

39. The method of claim 36, wherein a strand of the double-stranded RNA molecule is 23 nucleotides in length.

40. The method of claim 16, wherein the expression of the mRNA is determined using an in vitro RNA interference assay.

41. A method of producing a double-stranded RNA molecule of 21 to 23 nucleotides in length that mediates RNA interference, comprising:
synthesizing the double-stranded RNA molecule such that the RNA is in the form of two separate complementary RNA strands which are not covalently linked and each RNA strand has a length of from 21 to 23 nucleotides, wherein one strand of the double-stranded RNA molecule is perfectly complementary to a target mRNA to mediate RNA interference of the target mRNA, thereby producing the double-stranded RNA molecule.

42. The method of claim 41, wherein a strand of the double-stranded RNA molecule is 21 nucleotides in length.

43. The method of claim 41, wherein a strand of the double-stranded RNA molecule is 22 nucleotides in length.

44. The method of claim 41, wherein a strand of the double-stranded RNA molecule is 23 nucleotides in length.

45. The method of claim 41, wherein the expression of the mRNA is determined using an in vitro RNA interference assay.

46. The method of claim 41, wherein both strands of the double-stranded RNA molecule are 21 nucleotides in length.

47. The method of claim 41, wherein both strands of the double-stranded RNA molecule are 22 nucleotides in length.

48. The method of claim 41, wherein both strands of the double-stranded RNA molecule are 23 nucleotides in length.

49. The method of claim 41, wherein the double-stranded RNA molecule comprises one or more non-naturally occurring nucleotides.

50. The method of claim 41, wherein the double-stranded RNA molecule comprises one or more non-standard nucleotides.

51. The method of claim 41, wherein the double-stranded RNA molecule comprises one or more deoxyribonucleotides.

52. The method of claim 41, wherein the mRNA is a cellular mRNA.

53. The method of claim 41, wherein the mRNA is an oncogene mRNA.

54. The method of claim 41, wherein the mRNA encodes a viral protein.

55. The method of claim 1, wherein the mRNA is a cellular mRNA.

56. The method of claim 1, wherein the mRNA is an oncogene mRNA.

57. The method of claim 1, wherein the mRNA encodes a viral protein.

58. The method of claim 14, wherein the mRNA is a cellular mRNA.

59. The method of claim 14, wherein the mRNA is an oncogene mRNA.

60. The method of claim 14, wherein the mRNA encodes a viral protein.

61. The method of claim 36, wherein the mRNA is a cellular mRNA.

62. The method of claim 36, wherein the mRNA is an oncogene mRNA.

63. The method of claim 36, wherein the mRNA encodes a viral protein.

\* \* \* \* \*

UNITED STATES PATENT AND TRADEMARK OFFICE
CERTIFICATE OF CORRECTION

| | | |
|---|---|---|
| PATENT NO. | : 8,632,997 B2 | Page 1 of 1 |
| APPLICATION NO. | : 12/897749 | |
| DATED | : January 21, 2014 | |
| INVENTOR(S) | : Tuschl et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 22 days.

Signed and Sealed this
First Day of September, 2015

Michelle K. Lee
*Director of the United States Patent and Trademark Office*

SEQUENCE LISTING

<160> NUMBER OF SEQ ID NOS: 20

<210> SEQ ID NO 1
<211> LENGTH: 267
<212> TYPE: RNA
<213> ORGANISM: Artificial Sequence
<220> FEATURE:
<223> OTHER INFORMATION: Description of Artificial Sequence: Synthetic
      first 267 nt of Rr-luc

<400> SEQUENCE: 1
gaauacaagc uugggccuag ccaccaugac uucgaaaguu uaugauccag aacaaaggaa    60
acggaugaua acugguccgc aguggugggc cagauguaaa caaaugaaug uucuugauuc   120
auuuauuaau uauuaugauu cagaaaaaca ugcagaaaau gcuguauuu uuuuacaugg    180 uaacgcggcc ucuucuuauu uauggcgaca uguugugcca cauauugagc caguagcgcg   240
guguauuaua ccagaccuua uugguau                                      267

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Synthetic
      5' sense RNA primer for dsRNA 'C'

<400> SEQUENCE: 2
gcgtaatacg actcactata gaacaaagga aacggatgat                         40

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      3' sense RNA primer for dsRNA 'C'

<400> SEQUENCE: 3
gaagaagtta ttctccaaaa                                               20

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      5' asRNA primer for dsRNA 'C'

<400> SEQUENCE: 4
gcgtaatacg actcactata gaagaagtta ttctccaaaa                         40

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      3' asRNA primer for dsRNA 'C'

<400> SEQUENCE: 5
gaacaaagga aacggatgat                                               20

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Synthetic
      5' sense RNA primer for dsRNA 'A'

<400> SEQUENCE: 6
gcgtaatacg actcactata gtagcgcggt gtattatacc                         40

<210> SEQ ID NO 7

```
<211> LENGTH: 20
<212> TYPE: DNA
<213> ORGANISM: Artificial Sequence
<220> FEATURE:
<223> OTHER INFORMATION: Description of Artificial Sequence: Synthetic
      3' sense RNA primer for dsRNA 'A'

<400> SEQUENCE: 7
gtacaacgtc aggtttacca                                                    20

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      5' as RNA primer for dsRNA 'A'

<400> SEQUENCE: 8
gcgtaatacg actcactata gtacaacgtc aggtttacca                              40

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      3' asRNA primer for dsRNA 'A'

<400> SEQUENCE: 9
gtagcgcggt gtattatacc                                                    20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      sense sequence of siRNA targeting GL2
<220> FEATURE:
<223> OTHER INFORMATION: Description of Combined DNA/RNA Molecule:
      Synthetic sense sequence of siRNA targeting GL2

<400> SEQUENCE: 10
cguacgcgga auacuucgat t                                                  21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      antisense sequence of siRNA targeting GL2
<220> FEATURE:
<223> OTHER INFORMATION: Description of Combined DNA/RNA Molecule:
      Synthetic antisense sequence of siRNA targeting GL2

<400> SEQUENCE: 11
ucgaaguauu ccgcguacgt t                                                  21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      sense sequence of siRNA targeting GL3
<220> FEATURE:
<223> OTHER INFORMATION: Description of Combined DNA/RNA Molecule:
      Synthetic sense sequence of siRNA targeting GL3
```

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic antisense sequence of siRNA targeting GL3
<220> FEATURE:
<223> OTHER INFORMATION: Description of Combined DNA/RNA Molecule: Synthetic antisense sequence of siRNA targeting GL3

<400> SEQUENCE: 13
ucgaaguacu cagcguaagt t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic sense sequence of siRNA targeting RL
<220> FEATURE:
<223> OTHER INFORMATION: Description of Combined DNA/RNA Molecule: Synthetic sense sequence of siRNA targeting RL

<400> SEQUENCE: 14
aaacaugcag aaaaugcugt t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic antisense sequence of siRNA targeting RL
<220> FEATURE:
<223> OTHER INFORMATION: Description of Combined DNA/RNA Molecule: Synthetic antisense sequence of siRNA targeting RL

<400> SEQUENCE: 15
cagcauuuuc ugcauguuut t                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic sense sequence of siRNA targeting invGL2
<220> FEATURE:
<223> OTHER INFORMATION: Description of Combined DNA/RNA Molecule: Synthetic sense sequence of siRNA targeting invGL2

<400> SEQUENCE: 16
agcuucauaa ggcgcaugct t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic antisense sequence of siRNA targeting invGL2
<220> FEATURE:
<223> OTHER INFORMATION: Description of Combined DNA/RNA Molecule: Synthetic antisense sequence of siRNA targeting invGL2

```
<400> SEQUENCE: 17
gcaugcgccu uaugaagcut t                                              21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      sense sequence of siRNA targeting uGL2

<400> SEQUENCE: 18
cguacgcgga auacuucgau u                                              21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      antisense sequence of siRNA targeting uGL2

<400> SEQUENCE: 19
ucgaaguauu ccgcguacgu u                                              21

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aaaaaaaaaa aaaaaaaaaa aaaaa                                          25
```